United States Patent
Hashimoto et al.

(10) Patent No.: US 12,084,670 B2
(45) Date of Patent: Sep. 10, 2024

(54) REGULATING ALKALOIDS

(71) Applicant: 22nd Century Limited, LLC, Buffalo, NY (US)

(72) Inventors: Takashi Hashimoto, Ikoma (JP); Akira Kato, Nara (JP)

(73) Assignee: 22nd Century Limited, LLC, Buffalo, NY (US)

( * ) Notice: Subject to any disclaimer, the term of this patent is extended or adjusted under 35 U.S.C. 154(b) by 0 days.

(21) Appl. No.: 18/093,784

(22) Filed: Jan. 5, 2023

(65) Prior Publication Data

US 2023/0340510 A1   Oct. 26, 2023

Related U.S. Application Data

(60) Division of application No. 16/925,069, filed on Jul. 9, 2020, now Pat. No. 11,572,568, which is a continuation of application No. 16/003,066, filed on Jun. 7, 2018, now Pat. No. 10,731,172, which is a division of application No. 14/822,105, filed on Aug. 10, 2015, now Pat. No. 9,994,860, which is a division of application No. 11/941,950, filed on Nov. 18, 2007, now Pat. No. 9,102,948.

(60) Provisional application No. 60/866,352, filed on Nov. 17, 2006.

(51) Int. Cl.
| | |
|---|---|
| C12N 15/82 | (2006.01) |
| A24B 13/00 | (2006.01) |
| A24B 15/10 | (2006.01) |
| A61K 31/455 | (2006.01) |
| C12N 9/02 | (2006.01) |
| C12N 9/06 | (2006.01) |

(52) U.S. Cl.
CPC ......... *C12N 15/8218* (2013.01); *A24B 13/00* (2013.01); *A24B 15/10* (2013.01); *A61K 31/455* (2013.01); *C12N 9/0004* (2013.01); *C12N 9/0012* (2013.01); *C12N 9/0022* (2013.01); *C12N 15/8216* (2013.01); *C12N 15/8243* (2013.01); *C12N 15/8279* (2013.01); *C12N 15/8286* (2013.01); *C12Y 104/03006* (2013.01); *Y02A 40/146* (2018.01)

(58) Field of Classification Search
CPC ............. C12N 15/8215; C12N 15/8218
See application file for complete search history.

(56) References Cited

U.S. PATENT DOCUMENTS

| | | |
|---|---|---|
| 4,407,956 A | 10/1983 | Howell |
| 4,987,071 A | 1/1991 | Cech et al. |
| 5,459,252 A | 10/1995 | Conkling et al. |
| 5,466,785 A | 11/1995 | De Framond |
| 5,559,021 A | 9/1996 | Smith et al. |
| 5,580,967 A | 12/1996 | Joyce |
| 5,583,032 A | 12/1996 | Torrence et al. |
| 5,589,367 A | 12/1996 | Donson et al. |
| 5,591,601 A | 1/1997 | Wagner et al. |
| 5,595,877 A | 1/1997 | Gold et al. |
| 5,622,854 A | 4/1997 | Draper |
| 5,633,363 A | 5/1997 | Colbert et al. |
| 5,803,081 A | 9/1998 | O'Donnell, Jr. et al. |
| 5,837,848 A | 11/1998 | Ely et al. |
| 5,837,876 A | 11/1998 | Conkling et al. |
| 5,852,041 A | 12/1998 | Cosford et al. |
| 6,018,099 A | 1/2000 | De Framond |
| 6,135,121 A | 10/2000 | Williams |
| 6,271,360 B1 | 8/2001 | Metz et al. |
| 6,344,222 B1 | 2/2002 | Cherukuri |
| 6,423,520 B1 | 7/2002 | Conkling et al. |
| 6,479,292 B1 | 11/2002 | Metz et al. |
| 6,805,134 B2 | 10/2004 | Peele |
| 6,895,974 B2 | 5/2005 | Peele |
| 6,959,712 B2 | 11/2005 | Bereman et al. |
| 7,060,500 B2 | 6/2006 | Metz et al. |
| 8,410,341 B2 * | 4/2013 | Page .............. C12N 15/8243 536/23.6 |
| 9,422,532 B2 * | 8/2016 | Page .............. C12N 9/0022 |
| 2003/0106105 A1 | 6/2003 | Hoffman et al. |
| 2003/0221213 A1 | 11/2003 | Rommens et al. |
| 2004/0107455 A1 | 6/2004 | Rommend et al. |
| 2004/0143874 A1 | 7/2004 | Moller et al. |
| 2005/0010974 A1 | 1/2005 | Milligan et al. |

(Continued)

FOREIGN PATENT DOCUMENTS

| | | |
|---|---|---|
| WO | WO 2000/52168 | 9/2000 |
| WO | WO 2001/59086 A2 | 8/2001 |

(Continued)

OTHER PUBLICATIONS

A. de la Peña et al., "Transgenic rye plants obtained by injecting DNA into young floral tillers", Nature, vol. 325, Jan. 15, 1987, pp. 274-276.

(Continued)

*Primary Examiner* — Russell Kallis

(74) *Attorney, Agent, or Firm* — Foley & Lardner LLP

(57) ABSTRACT

MPO1 and MPO2 can be regulated for either decreasing or increasing alkaloid levels in plants, in particular in *Nicotiana* plants. In particular, suppressing or overexpressing one or more of MPO1 and MPO2 may be used to decrease or increase nicotine and nicotinic alkaloid levels in tobacco plants. Suppression or overexpression of one or more of MPO1 and MPO2 may be used in combination with modification of expression of other genes encoding enzymes on the nicotinic alkaloid biosynthetic pathway such as A622, NBB1, PMT, and QPT.

4 Claims, 11 Drawing Sheets
Specification includes a Sequence Listing.

(56) References Cited

U.S. PATENT DOCUMENTS

| | | |
|---|---|---|
| 2005/0034365 A1 | 2/2005 | Li et al. |
| 2005/0072047 A1 | 4/2005 | Conkling et al. |
| 2005/0097633 A1 | 5/2005 | Diehn et al. |
| 2005/0223442 A1 | 10/2005 | Xu |
| 2006/0041949 A1 | 2/2006 | Xu et al. |
| 2006/0185684 A1 | 8/2006 | Albino et al. |
| 2007/0072224 A1 | 3/2007 | Reeves et al. |
| 2007/0199097 A1 | 8/2007 | Xu et al. |
| 2009/0055964 A1 | 2/2009 | Gelesko et al. |
| 2009/0210958 A1 | 8/2009 | Page et al. |
| 2015/0136152 A1* | 5/2015 | de Godoy Lusso ..... A24D 1/00 800/317.3 |

FOREIGN PATENT DOCUMENTS

| | | |
|---|---|---|
| WO | WO 2002/38588 A2 | 5/2002 |
| WO | WO 2002/098208 A2 | 12/2002 |
| WO | WO 2004/076625 A2 | 9/2004 |
| WO | WO 2005/018307 A1 | 3/2005 |
| WO | WO 2006/091194 A1 | 8/2006 |
| WO | WO 2006/109197 A2 | 10/2006 |
| WO | WO 2007/072224 A2 | 6/2007 |

OTHER PUBLICATIONS

Akama et al., "Efficient transformation of *Arabidopsis thaliana*: comparison of the efficiencies with various organs, plant ecotypes and Agrobacterium strains", Plant Cell Reports (1992) 12: 7-11.

Altschul et al., "Gapped Blast and PSI-Blast: a new generation of protein database search programs", Nucleic Acids Research, 1997, vol. 23, No. 17, pp. 3389-3402.

Archer et al., "Strategies for improving heterologous protein production from filamentous fungi", Antonie van Leeuwenhoek 65: 245-250, 1994.

Armitage et al., "Evaluation of a low to middle tar/medium nicotine cigarette designed to maintain nicotine delivery to the smoker", Psychopharmacology (1988) 96: 47-453.

Bacon et al., "Chemical Changes in Tobacco during Flue-Curing", Industrial and Engineering Chemistry, vol. 44, No. 2, pp. 292-296, Feb. 1952.

Beaucage et al., "Deoxynucleoside Phosphoramidites—A New Class of Key Intermediates for Deoxypolynucleotide Synthesis", Tetrahedron Letters, vol. 22, No. 20, pp. 1859-1862, 1981.

Bechtold et al., "In planta Agrobacterium mediated gene transfer by infiltration of adult *Arabidopsis thaliana* plants", C.R. Acad. Sci. Paris, Sciences de la vie/Life sciences, 1993:316, 1194-1199.

Beetham et al., 'A tool for functional plant genomics: Chimeric RNA/DNA oligonucleotides cause in vivo gene-specific mutations, Proc. Natl. Acad. Sci. USA, vol. 96, pp. 8774-8778, Jul. 1999.

Broothaerts et al., "Gene transfer to plants by diverse species of bacteria", Nature, vol. 433, Feb. 10, 2005, pp. 629-633.

Bush et al., "Biosynthesis and metabolism of nicotine and related alkaloids", Nicotine and Related Alkaloids: Absorption Distribution Metabolism and Excretion, 1993, pp. 1-30.

Carter et al., "Tobacco Nectarin V Is a Flavin-Containing Berberine Bridge Enzyme-Like Protein with Glucose Oxidase Activity", Plant Physiology, Jan. 2004, vol. 134, pp. 460-469.

Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology 53: 87-105, 2003.

Clough et al., "Floral dip: a simplified method for Agrobacterium-mediated transformation of *Arabidopsis thaliana*", The Plant Journal (1998) 16(6), pp. 735-743.

David et al., "Conservation of T-DNA in Plants Regenerated From Hairy Root Cultures", Bio/Technology, Jan. 1984, pp. 73-76.

Dittrich et al., "Molecular cloning, expression, and induction of berberine bridge enzyme, an enzyme essential to the formation of benzophenanthridine alkaloids in the response of plants to pathogenic attack", Proc. Natl. Acad. Sci., vol. 88, pp. 9969-9973, Nov. 1991.

Djordjevic et al., "Tobacco-Specific Nitrosamine Accumulation and Distribution in Flue-Cured Tobacco Alkaloid Isolines", J. Agric. Food Chem., 1989, 37, 752-756.

Dym, O. et al. "Sequence-structure analysis of FAD-containing proteins", Protein Science, 2001, vol. 10, pp. 1712-1728.

Fagerström, "Effects of a Nicotine-Enriched Cigarette on Nicotine Titration, Daily Cigarette Consuption, and Levels of Carbon Monoxide, Cotinine, and Nicotine", Psychopharmacology (1982) 77: 164-167.

Felpin et al., "Efficient Enantiomeric Synthesis of Pyrrolidine and Piperidine Alkaloids from Tobacco", J. Org. Chem. 2001, 66, 6305-6312.

Gori et al., "Analytical Cigarette Yields as Predictors of Smoke Bioavailability", Regulatory Toxicology and Pharmacology 5, 314-326 (1985).

Gossen et al., "Tight control of gene expression in mammalian cells by tetracycline-responsive promoters", Proc. Natl. Acad. Sci. USA, vol. 89, pp. 5547-5551, 1992.

Hakkinen, S. et al. "Functional characterisation of genes involved in pyridine alkaloid biosynthesis in tobacco", Phytochemistry, 2007, vol. 68, pp. 2773-2785.

Hecht et al., "Tobacco-Specific Nitrosamines: Occurrence, Formation, Carcinogenicity, and Metabolism", Accounts of Chemical Research, 1979 American Chemical Society, vol. 12, pp. 92-98.

Hibi et al., "Putrescine N-Methyltransferase in Cultured Roots of Hyoscyamus albus", Plant Physiol. (1992), 100, 826-835.

Hoffmann et al., "Origin in Tobacco Smoke of N'-Nitrosonornicotine, a Tobacco-Specific Carcinogen: Brief Communication", J. Natl. Cancer Inst. vol. 58, No. 6, Jun. 1977, pp. 1841-1844.

Hoffmann et al., "The Changing Cigarette: Chemical Studies and Bioassays", Smoking and Tobacco Control Monograph No. 13, Chapter 5, Nov. 19, 2001, pp. 159-192.

Hoffmann et al., "Tobacco-Specific N-Nitrosamines and Areca-Derived N-Nitrosamines: Chemistry, Biochemistry, Carcinogenicity, and Relevance to Humans", Journal of Toxicology and Environmental Health, 41: 1-52, 1994.

Hsu et al., "Phloem Mobility of Xenobiotics VI. A Phloem-Mobile Pro-nematicide Based on Oxamyl Exhibiting Root-Specific Activation in Transgenic Tobacco", Pestic. Sci, 1995, 44, pp. 9-19.

Hwang et al., "An *Arabidopsis thaliana* root-specific kinase homolog is induced by dehydration, ABA, and NaCl", The Plant Journal (1995), 8(1), 37-43.

Kanegae et al., "Species-Dependent Expression of the Hyoscyamine 6β-Hydroxylase Gene in the Pericycle", Plant Physiol. (1994) 105: 483-490.

Katoh et al., "Analysis of expression sequence tags from Nicotiana sylvestris", Proc. Japan Acad. 79, No. 6, Ser. B (2003), pp. 151-154.

Leegood, "16: Carbon Metabolism", Photosynthesis and Production in a Changing Environment A Field and Laboratory Manual, Edited by D.O. Hall et al.,(1993), pp. 247-267.

Legg et al., "Inheritance of Percent Total Alkaloids in *Nicotiana Tabacum* L. II. Genetic Effects of Two Loci in Burley 21 x LA Burley 21 Populations," Can. J. Genet. Cytol., vol. 13, pp. 287-291 (1971).

Lin, L. et al. "Steroleosin, a Sterol-Binding Dehydrogenase in Seed Oil Bodies", Plant Physiology, Apr. 2002, vol. 128, pp. 1200-1211.

Lörz et al., "Gene transfer to cereal cells mediated by protoplast transformation", Mol. Gen Genet (1985), 199: 178-182.

Matteucci et al., "Synthesis of Deoxyoligonucleotides on a Polymer Support", J. Am. Chem. Soc. 1981, 103, 3185-3191.

Mayfield et al., "Expression of human antibodies in eukaryotic micro-algae", Vaccine, 23, (2005), 1828-1832.

Miyagawa et al., "Evaluation of the Defense System in Chloroplasts to Photooxidative Stress Caused by Paraquat Using Transgenic Tobacco Plants Expressing Catalase from *Escherichia coli*", Plant Cell Physiol. 41(3): 311-320 (2000).

Miyagawa et al., "Overexpression of a cyanobacterial fructose-1,6-/sedoheptulose-1, 7-bisphosphatase in tobacco enhances photosynthesis and growth", Nature Biotechnolgoy, vol. 19, Oct. 2001, pp. 965-969.

(56) References Cited

OTHER PUBLICATIONS

Moyano et al., "Alkaloid production in Duboisia hybrid hairy root cultures overexpressing the pmt gene", Phytochemistry 59 (2002) 697-702.
Moyano et al., "Effect of pmt gene overexpression on tropane alkaloid production in transformed root cultures of Datura metal and Hyosyamus muticus", Jouranl fo Experimental Botany, vol. 54, No. 381, pp. 203-211, Jan. 2003.
Murillo et al., "Engineering photoassimilate partitioning in tobacco plants improves growth and productivity and provides pathogen resistance", The Plant Journal (2003) 36, 330-341.
Nagel et al., "Electroporation of binary Ti plasmid vector into Agrobacterium tumefaciens and Agrobacterium rhizogenes", FEMS Microbiology Letters, 67 (1990), 325-328.
Oksman-Caldentey et al., "Chapter 13: Regulation of Tropane Alkaloid Metabolism in Plants and Plant Cell Cultures", Metabolic Engineering of Plant Secondary Metabolism, Kluwar Academic Publishers, 2000, pp. 253-281.
Paszkowski et al., "Direct gene transfer to plants", The EMBO Journal, vol. 3, No. 12, pp. 2717-2722, 1984.
Pillsbury et al., "Tobacco Tar and Nicotine in Cigarette Smoke", Journal of the AOAC, vol. 52, No. 3, 1969, pp. 458-462.
Reed et al., "The A and B loci of Nicotiana tabacum have non-equivalent effects on the mRNA levels of four alkaloid biosynthetic genes", Plant Science 167 (2004) 1123 -1130.
Restrepo et al., "Nuclear Transport of Plant Potyviral Proteins", The Plant Cell, vol. 2, 987-998, Oct. 1990.
Rhodes et al., "Genetically Transformed Maize Plants from Protoplasts", Science, vol. 240, Apr. 8, 1988, pp. 204-207.
Riechers et al., "Structure and expression of the gene family encoding putrescine N-methyltransferase in Nicotiana tabacum: new clues to the evolutionary origin of cultivated tobacco", Plant Molcular Biology 41: 387-401, 1999.
Rose, "The Role of Upper Airway Stimulation in Smoking", Nicotine Replacement: A Critical Evaluation, pp. 95-106, 1988.
Rothe et al., "Alkaloids in plants and root cultures of Atropa belladonna overexpressing putrescine N-methyltransferase", Journal of Experimental Botany, vol. 54, No. 390, pp. 2065-2070, Sep. 2003.
Russell, Public Health and Levels of Nicotine: Should Nicotine Levels in Cigarettes be Minimized or Maximized? pp. 265-284 (2000).
Sagi et al., "Transient gene expression in electroporated banana (Musa spp., cv. 'Bluggoe', ABB group) protoplasts isolated from regenerable embryogenetic cell suspensions", Plant Cell Reports, (1994) 13: 262-266.
Saitoh et al., "The Alkaloid Contents of Sixty *Nicotiana* Species", Phytochemistry, vol. 24, No. 3, pp. 477-480, 1985.
Sambrook et al., "Chapter 7: Extraction, Purification, and Analysis of mRNA from Eukaryotic Cells", Molecular Cloning A Laboratory Manual vol. 1, Third Edition, 2001, 96 pages.
Shimamoto et al., "Fertile transgenic rice plants regenerated from transformed protoplasts", Nature, vol. 338, Mar. 16, 1989, pp. 274-276.
Shoji et al., "Ethylene Suppresses Jasmonate-Induced Gene Expression in Nicotine Bio-synthesis", Plant Cell Physiol. 41(9): 1072-1076, (2000).
Shoji et al., "Jasmonate Induction of Putrescine N-Methyltransferase Genes in the Root of Nicotiana sylvestris", Plant Cell Physiol. 41(7): 831-839 (2000).
Sinclair et al., "Molecular characterization of puinolinate phosphoribosyltransferase (QPRTase) in Nicotiana", Plant Molecular Biology, 44: 603-617, 2000.
Singer, "The Upside to Nicotine?", Technology Review: MIT's Magazine of Innovation, vol. 109, No. 3, Jul.-Aug. 2006, 3 pages.
Steppuhn et al., "Nicotine's Defensive Function in Nature", PLoS Biology, Aug. 2004, vol. 2, Issue 8, 1074-1080.
Stratton et al., "Clearing the Smoke Assessing the Science Base for Tobacco Harm Reduction", Committee to Assess the Science Base for Tobacco Harm Reduction, Board on Health Promotion and Disease Prevention, Institute of Medicine, 2001, 7 pages.
Tamoi et al., "Contribution of Fructose-1,6-bisphosphatase and Sedoheptulose-1,7-bisphosphatase to the Photosynthetic Rate and Carbon Flow in the Calvin Cycle in Transgenic Plants", Plant Cell Physiol. 47(3): 380-390 (2006).
Thompson et al., "Characterization of the herbicide-resistance gene bar from Streptomyces hygroscopicus", The EMBO Journal, vol. 6, No. 9, pp. 2519-2523, 1987.
Tobacco: Production, Chemistry and Technology,—Breeding and Genetics, 1999, Coresta Blackwell Science Ltd., Edited by D. Layten Davis et al., 1999, pp. 45-46.
Tso, "Production, Physiology, and Biochemistry of Tobacco Plant", 1990, Ideals Inc., 4 pages.
UniProtKB Accession No. A7WPL6 (A7WPL6_TOBAC)—berberine bridge enzyme like protein—*Nicotiana tabacum* (Common tobacco), Oct. 23, 2007, Accessed Jul. 30, 2013, 3 pages.
Voelckel et al., "Anti-sense expression of putrescine N-methyltransferase confirms defensive role of nicotine in Nocotiana sylvestris against Manduca sexta", Chemoecology 11: 121-126 (2001).
Woodman et al., "The separate effects of tar and nicotine on the cigarette smoking manoeuvre", Eur J Respir Dis, (1987) 70, pp. 316-321.
Zhang et al., "Engineering tropane biosynthetic pathway in Hyosyamus niger hairy root cultures", PNAS, Apr. 2004, vol. 101, No. 17, pp. 6786-6791.
Zhu et al., "Targeted manipulation of maize genes in vivo using chimeric RNA/DNA oligonucleotides", Proc. Natl. Acad. Sci. USA, vol. 96, pp. 8768-8773, Jul. 1999.
Zoller et al., "Oligonucleotide-directed mutagenesis using M13-derived vectors: an efficient and general procedure for the production of point mutations in any fragment of DNA", Nucleic Acids Research, vol. 10, No. 20, 1982, pp. 6487-6500.
Office Action issued in related U.S. Appl. No. 14/820,455, dated May 16, 2017.
Office Action issued in related U.S. Appl. No. 14/820,455, dated Oct. 7, 2016.
Saunders, et al., Plant Physiology, vol. 64, pp. 236-240 (1979).
Office Action issued in co-pending U.S. Appl. No. 14/820,455, dated Jun. 28, 2018.
Notice of Allowance issued in co-pending U.S. Appl. No. 14/820,455, dated Nov. 29, 2018.
Saunders and Bush Plant Physiol. (1979) 64, pp. 236-240.

\* cited by examiner

A Model of the Nicotine Biosynthetic Pathway

A Model of the Biosynthetic Pathways of Scopolamine and Cocaine

RNA Gel Blot Analysis of Regulation by NIC loci and MeJA Treatment of MPO and PMT RT-PCR Analysis of Expression Levels of *MPO1* and *MPO2*

Digestion products are indicated by asterisks.
Undigested MPO PCR products are indicated
by arrows.

Phylogenetic Tree of Tobacco N-Methylputrescine Oxidases, Plant Diamine Oxidases, and Arabidopsis Homologues

FIGURE 6
FIGURE 6A. T-DNA region of pBI-MPO-Ri
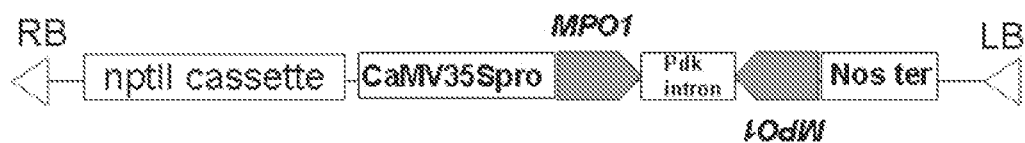
FIGURE 6B. T-DNA region of pBI-MPO
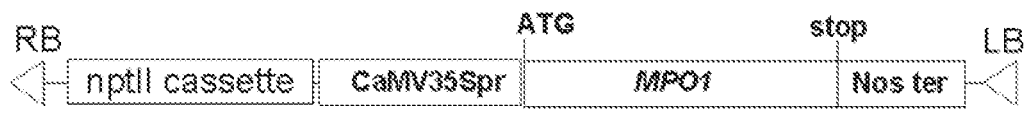
FIGURE 6C. T-DNA region of pTobRD2-MPO
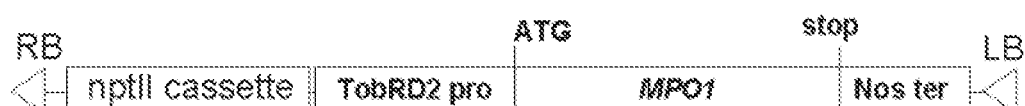
FIGURE 6D. T-DNA region of pTPoxTMoxTQRi
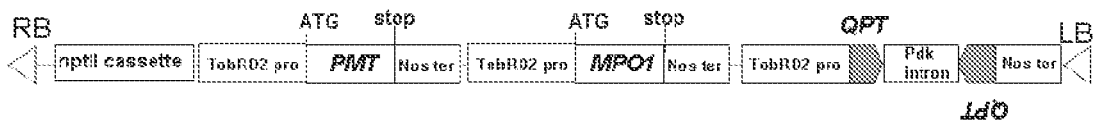

RNAi-Mediated Down-Regulation of MPO Genes

MPO = Methylputrescine oxidase
PMT = Putrescine methyltransferase
QPT = Quinolinate phosphoribosyl transferase
TUB = tubulin MPO Activity in MPO-down-regulated Hairy Root Line Alkaloid Levels in MPO-down-regulated Hairy Root Lines

FIGURE 10A Northern Blot Analysis
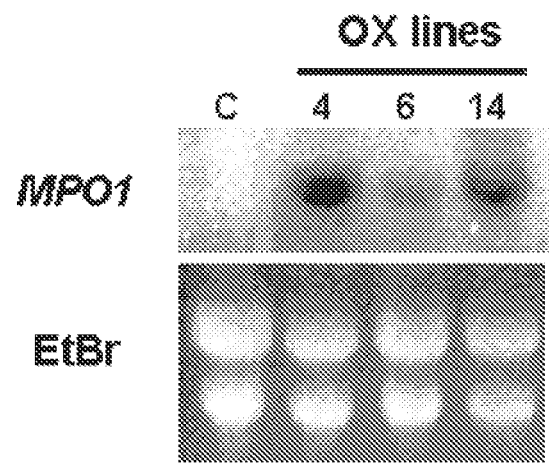
FIGURE 10B MPO Activity
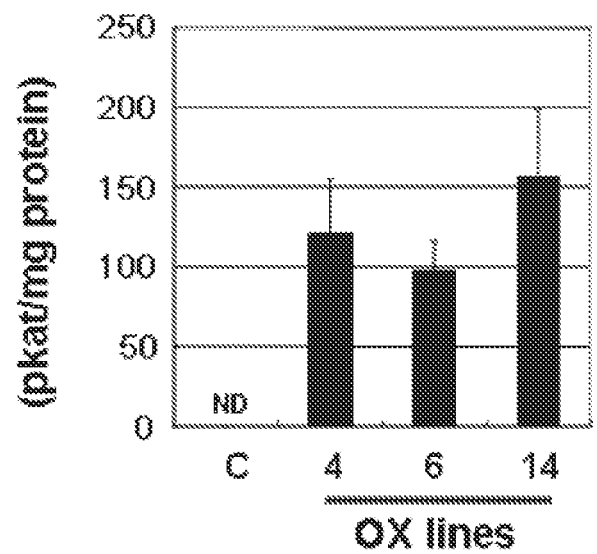

REGULATING ALKALOIDS

CROSS-REFERENCE TO RELATED PATENT APPLICATIONS

This application is a divisional of U.S. patent application Ser. No. 16/925,069, filed Jul. 9, 2020, which is a continuation of U.S. patent application Ser. No. 16/003,066, filed Jun. 7, 2018, now U.S. Pat. No. 10,731,172, which is a divisional of U.S. patent application Ser. No. 14/822,105, filed Aug. 10, 2015, now U.S. Pat. No. 9,994,860, which is a divisional of U.S. patent application Ser. No. 11/941,950, filed Nov. 18, 2007, now U.S. Pat. No. 9,102,948, which claims the benefit of U.S. Provisional Patent Application No. 60/866,352, filed Nov. 17, 2006. The contents of these applications are incorporated herein by reference in their entirety.

SEQUENCE LISTING

The specification further incorporates by reference the Sequence Listing submitted herewith. The Sequence Listing .xml file identified as 045952_0790, is 35 bytes in size and was created on May 10, 2023. The Sequence Listing, electronically filed herewith does not extend beyond the scope of the specification, and does not contain new matter.

FIELD OF THE INVENTION

The present invention relates to the field of molecular biology and regulation of alkaloid synthesis. More specifically, the invention relates to regulating alkaloid content in a plant, particularly but not exclusively nicotinic alkaloids in a tobacco plant.

BACKGROUND

Genes encoding nicotine biosynthesis enzymes are known. For example, the tobacco quinolate phosphoribosyl transferase (QPT) gene has been cloned; see U.S. Pat. No. 6,423,520 and Sinclair et al., *Plant Mol. Biol.* 44:603-17 (2000). QPT suppression provides significant nicotinic alkaloid reductions in transgenic tobacco plants. Xie et al., *Recent Advances in Tobacco Science* 30:17-37 (2004). Likewise, suppression of an endogenous putrescine methyl transferase (PMT) sequence has been shown to reduce nicotine levels but increase anatabine levels by about 2-to-6-fold. Hibi et al., *Plant Cell* 6:723-35 (1994); Chintapakorn and Hamill, *Plant Mol. Biol.* 53:87-105 (2003); Steppuhn et al. PLoS Biol 2:8:e217:1074-1080 (2004). Levels of nicotine and other nicotinic alkaloids are reduced in tobacco by suppressing either the A622 or NBB1 nicotine biosynthesis genes. See WO/2006/109197.

Despite this, a comprehensive understanding of how the nicotine biosynthetic pathway functions is essential. Accordingly, further research efforts have been underway to elucidate the biochemistry and molecular biology of this pathway, including the identification of all related genes. Additional insights into biosynthesis pathways of other nicotinic alkaloids and of other alkaloids found in non-*Nicotiana* plants would be facilitated by a comprehensive understanding of the nicotine biosynthesis pathway in tobacco.

Reducing total alkaloid content in tobacco would increase the value of tobacco as a biomass resource. Reduced-alkaloid tobacco is more amenable for non-traditional purposes, such as biomass and derived products. For example, it is advantageous to use reduced-alkaloid tobacco for producing ethanol and protein co-products. Additionally, alkaloid-free tobacco or fractions thereof may be used as a forage crop, animal feed, or a human nutritive source. See WO/2002/098208.

An additional use of reduced-nicotine tobacco is for smoking cessation. Nicotine-reduced or nicotine-free tobacco cigarettes have assisted smokers in quitting smoking. Additionally, denicotinized cigarettes relieve craving and other smoking withdrawal symptoms. See Rose, *Psychopharmacology* 184:274-285 (2006) and Rose et al., *Nicotine Tobacco Res.* 8:89-101 (2006).

It may be beneficial to overexpress a nicotine biosynthesis gene, as means for increasing nicotine biosynthesis and accumulation in tobacco. For example, because nicotinic alkaloids play an important role in protecting plants against insects and herbivores, it is likely to be advantageous to increase nicotinic alkaloid synthesis in a host plant. From an herbivory perspective, increased nicotine synthesis and accumulation would provide an environmentally acceptable means for mediating plant-pest interactions.

As nicotine is the physically and psychologically active component in cigarette smoke, it may be advantageous to increase nicotine content in tobacco by genetic engineering. Research studies demonstrate that when supplementary nicotine is added to cigarette tobacco from an outside source, smokers inhale less of the more harmful components of smoke such as tar and carbon monoxide. See Armitage et al., *Psychopharmacology* 96:447-53 (1988), Fagerström, *Psychopharmacology* 77:164-67 (1982), Russell, *Nicotine and Public Health* 15:265-84 (2000), and Woodman et al., *European Journal of Respiratory Disease* 70:316-21 (1987). Likewise, a report by The Institute of Medicine of the U.S. on potential reduced exposure products (PREPS) concluded that "retaining nicotine at pleasurable or addictive levels while reducing the more toxic components of tobacco is another general strategy for harm reduction." See CLEARING THE SMOKE. ASSESSING THE SCIENCE BASE FOR TOBACCO HARM REDUCTION, IOM at page 29 (2001), commonly referred to as the "TOM Report" by the tobacco industry.

The part of the nicotine biosynthesis pathway that produces the N-methylpyrrolinium cation also is part of the pathway for the biosynthesis of other alkaloids, including medicinal tropane alkaloids. Hashimoto and Yamada, *Annu. Rev. Plant Physiol. Plant Mol. Biol.* 45:257-285 (1994); Kutchan, T. M., "Molecular genetics of plant alkaloid biosynthesis. In: Cordell, G. A. (ed.) 50 ALKALOIDS 257-316 (Academic Press, 1998).

A plant also can be genetically engineered to regulate its alkaloid profile, such as the ratio of a particular alkaloid to total alkaloid content. For example, if the goal is increasing the ratio of anatabine to total alkaloid content of a *N. tabacum* plant, PMT is suppressed. Chintapakorn and Hamill, supra.

As more alkaloid biosynthesis genes are discovered, including an understanding of their function and location in alkaloid biosynthesis pathways, the more sophisticated genetic engineering of these pathways can become. Accordingly, there is a continuing need to identify additional genes whose expression can be regulated to not only decrease or increase alkaloid(s) but to alter a plant's alkaloid profile, in particular, nicotinic alkaloids in *N. tabacum* plants.

SUMMARY OF THE INVENTION

The present inventors have identified two genes, MPO1 and MPO2, which can be regulated independently or simultaneously to achieve a decrease or increase of nicotine levels in *Nicotiana* plants, and to achieve a decrease or increase of tropane alkaloids in Erythroxylaceae, Solanaceae, and Convolvulaceae plant families.

In one aspect, the invention provides an isolated nucleic acid molecule comprising a nucleotide sequence selected from the group consisting of: (a) a nucleotide sequence set forth in SEQ ID NO: 1; (b) a nucleotide sequence set forth in SEQ ID NO: 3; (c) a nucleotide sequence comprising at least 15 consecutive nucleotides of the nucleotide sequence set forth in SEQ ID NO: 1 or 3; (d) a nucleotide sequence that encodes a polypeptide having the amino acid sequence set forth in SEQ ID NO: 2 or 4; and (e) a nucleotide sequence that encodes a polypeptide having an amino acid sequence with at least 80% similarity to at least one of SEQ ID NO: 2 and 4 and that has MPO activity. In one embodiment, a nucleic acid construct comprising the nucleic acid molecule, wherein the nucleic acid is operatively linked in sense, antisense, or inverted repeat orientation to a heterologous promoter. In a further embodiment, a plant cell comprises the nucleic acid construct. In another embodiment, there is provided a method of producing a reduced-alkaloid plant, comprising genetically engineering MPO suppression in the plant, wherein the engineering comprises introducing into a plant cell of the plant the nucleic acid construct. In a further embodiment, the plant is tobacco. In another embodiment, a tobacco plant comprises a chimeric nucleic acid construct, wherein the construct comprises the nucleic acid linked to a heterologous nucleic acid.

In another aspect, the invention provides a nucleic acid construct, comprising, in the 5' to 3' direction, a promoter operably linked to a heterologous nucleic acid encoding at least a portion of MPO1 or MPO2 in sense, antisense, or inverted repeat orientation, and a terminator. In an embodiment, a plant cell comprises the nucleic acid construct. In another embodiment, there is provided a method of producing a reduced-alkaloid plant, comprising genetically engineering MPO suppression in the plant, wherein the engineering comprises introducing into a plant cell of the plant the nucleic acid construct. In a further embodiment, the plant is tobacco.

In another aspect, the invention provides a mutational vector comprising a sequence of oligonucleotides targeting a region comprising 15 consecutive nucleotides of SEQ ID NO: 1 or 3.

In further embodiment, a method is provided for producing a reduced-alkaloid plant, comprising genetically engineering MPO suppression in the plant, wherein the engineering comprises introducing into a plant cell of the plant the aforementioned nucleic acid construct.

In another aspect, the invention provides a method for reducing an alkaloid in a tobacco plant, comprising (a) genetically engineering MPO suppression in the plant; and (b) suppressing at least one additional nicotine biosynthesis enzyme selected from the group consisting of aspartate oxidase, quinolinate synthase, quinolate phosphoribosyl transferase, ornithine decarboxylase, putrescine N-methyltransferase, A622, and NBB1.

In another aspect, the invention provides a tobacco plant having genetically engineered suppression of MPO and reduced content of nicotine. In one embodiment, the there is provided progeny of the tobacco plant, wherein the progeny have MPO suppression. In another embodiment, the invention provides seeds from the tobacco plant. In another embodiment, there is provided a reduced-alkaloid tobacco product comprising a portion of the tobacco plant. In a further embodiment, the product is a cigarette. In another further embodiment, there is provided a smoking cessation product comprising a portion of the tobacco plant.

In another aspect, the invention provides a reduced-alkaloid tobacco product produced from genetically engineered tobacco having suppressed MPO, wherein the product has a reduced collective amount of N'-nitrosonornicotine (NNN), 4-methylnitrosoamino-1-(3-pyridyl)-1-butanone (NNK), N'-nitrosoanatabine (NAT) and N'-nitrosoanabasine (NAB) compared to a similar tobacco product prepared from a non-genetically engineered control tobacco plant. In one embodiment, the product is a cigarette.

In another aspect, the invention provides an MPO1 polypeptide having the amino acid sequence of SEQ ID NO: 2

In another aspect, the invention provides an MPO2 polypeptide having the amino acid sequence of SEQ ID NO: 4

In another aspect, there is provided an isolated MPO enzyme encoded by a nucleic acid sequence selected from the group consisting of: (a) a nucleotide sequence set forth in SEQ ID NO: 1; (b) a nucleotide sequence set forth in SEQ ID NO: 3; (c) nucleic acid sequences which hybridize to at least one of SEQ ID NO: 1 and SEQ ID NO: 3 under moderate stringency or high stringency conditions and encode an MPO enzyme; and (d) nucleic acid sequences which differ from the nucleic acid sequence of (a), (b), or (c) above due to the degeneracy of the genetic code and encode an MPO enzyme.

In another aspect, the invention provides a method of producing an MPO enzyme, comprising (a) introducing an isolated nucleic molecule encoding at least one of MPO1 and MPO2 into a cell; and (b) growing the cell under conditions such that MPO enzyme is produced. In one embodiment, the cell is selected from the group consisting of bacteria, yeast, filamentous fungi, algae, green plants, and mammalian cells.

In another aspect, the invention provides a method for increasing alkaloids in a plant, comprising overexpressing MPO relative to a control plant. In one embodiment, the method further comprises overexpressing PMT. In another embodiment, an increased alkaloid plant is produced by the these methods. In another embodiment, an increased nicotine plant is produced by the these methods. In a further embodiment, an increased nicotine product is produced from the increased nicotine plant. In a still further embodiment, the product is selected from the group consisting of a cigarette, a pharmaceutical, and a nutraceutical.

In another aspect, the invention provides a method for increasing nicotine in a *Nicotiana* plant, comprising overexpressing at least one of MPO1 and MPO2 relative to a control plant. In one embodiment, the method further comprises overexpressing at least one of QPT, PMT, A622, and NBB1. In another embodiment, an increased alkaloid plant is produced by the these methods. In another embodiment, an increased nicotine plant is produced by the these methods. In a further embodiment, an increased nicotine product is produced from the increased nicotine plant. In a still further embodiment, the product is selected from the group consisting of a cigarette, a pharmaceutical, and a nutraceutical.

In another aspect, the invention provides a method for increasing nicotine and yield in a *Nicotiana* plant, comprising: (a) crossing an increased nicotine *Nicotiana* plant of claim 27 with a high yielding *Nicotiana* plant; and (b) selecting a progeny plant with increased nicotine and high yield. In an embodiment, an increased nicotine and yield plant is produced by the method.

In another aspect, the invention provides a method for increasing nicotine and yield in a *Nicotiana* plant, comprising (a) introducing into a Nicotiana plant a construct comprising, in the 5' to 3' direction, a promoter operably linked to a heterologous nucleic acid encoding an enzyme that increases yield; (b) regenerating transgenic Nicotiana plants from the plant; and (c) selecting a transgenic Nicotiana plant having increased nicotine content and increased yield relative to a control plant. In an embodiment, an increased nicotine and yield plant is produced by the method.

In another aspect, the invention provides a method for increasing the ratio of nicotine to total alkaloids in a tobacco plant, comprising: (a) overexpressing at last one of MPO1 and MPO2; (b) overexpressing PMT; and (c) suppressing QPT. In one embodiment, there is provided a plant produced by the method. In a further embodiment, a product with increased nicotine to total alkaloids is produced from the plant.

BRIEF DESCRIPTION OF THE DRAWINGS

FIG. 6: T-DNA regions of pBI-MPO-Ri, pBI-MPO, pTobRD2-MPO, and pTPoxTMoxTQRi.

FIG. 10A: MPO mRNA in BY-2 cells transformed with pBI-MPO.

FIG. 10B: MPO enzyme activity in BY-2 cells transformed with pBI-MPO.

DETAILED DESCRIPTION OF THE INVENTION

Figure 1A:
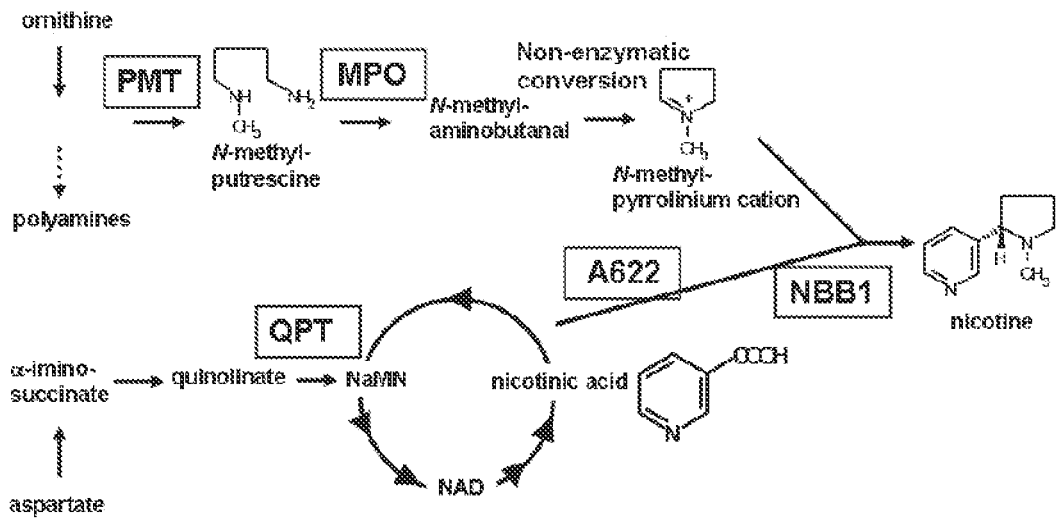
FIG. 1A: Depicts a model of the nicotine biosynthesis pathway. The abbreviations are: MPO1=methylputrescine oxidase-1, MPO2=methylputrescine oxidase-2, PMT=putrescine N-methyltransferase, QPT=quinolinate phosphoribosyl transferase. A662 and NBB1 are the products of genes recently identified as nicotine biosynthesis genes. See WO/2006/109197.
Figure 1B:
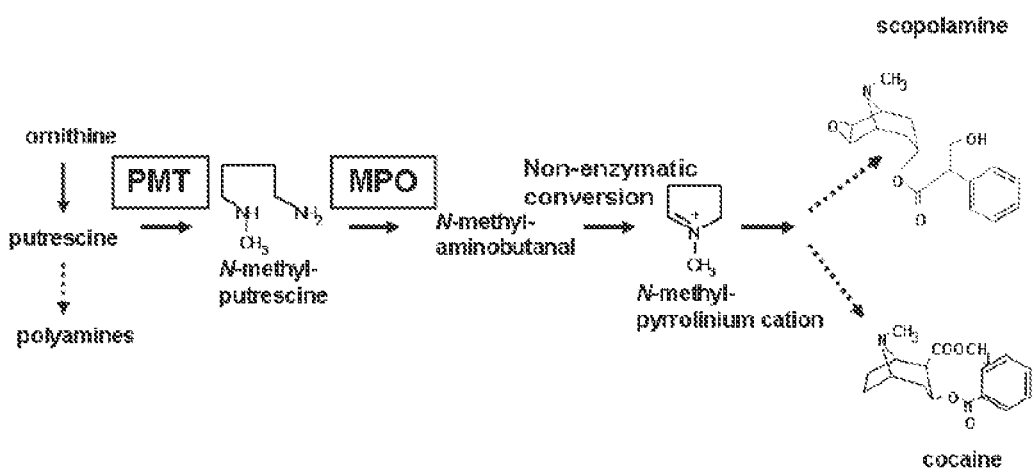
FIG. 1B: Depicts a model of the biosynthetic pathway of Scopolamine and cocaine.

The present inventors have cloned two N-methylputrescine oxidase (MPO) genes, N-methylputrescine oxidase-1 (MPO1) and N-methylputrescine oxidase-2 (MPO2). The nucleic acid sequence of MPO1, SEQ ID NO: 1, has been determined and encodes the polypeptide sequence set forth in SEQ ID NO: 2. The nucleic acid sequence of MPO2, SEQ ID NO: 3, has been determined and encodes the polypeptide sequence set forth in SEQ ID NO: 4. The nucleotide sequences of the MPO1 ORF and the MPO2 ORF are set forth in SEQ ID NO: 5 and SEQ ID NO: 6, respectively. All polynucleotide and polypeptide sequences of SEQ ID NO: 1 through SEQ ID NO: 6, including all respective variants thereof, are an object of the present invention.

MPO is a specific type of diamine oxidase (EC 1.4.3.6) that catalyzes the oxidative deamination of N-methylputrescine to 4-methylaminobutanal, which spontaneously cyclizes to N-methylpyrrolinium cation. Hashimoto, et al., Plant Phsyiol. 93:216-221 (1990). Tobacco MPO enzymes have been partially purified from the roots of N. tabacum and N. rustica, and were shown to oxidize N-methylputrescine more efficiently than putrescine and cadaverine Mizusaki et al., Phytochemistry 11:2757-2762 (1972); Feth and Wagner, Phytochemistry 24:1653-1655 (1985); Davies et al., Phytochemistry 28:1573-1578 (1989); Walton and McLauchlan, Phytochemistry 29:1455-1457 (1990); Haslam and Young, Phytochemistry 31:4075-4079 (1992); McLauchlan et al., Planta 191:440-445 (1993).

Inhibitor studies suggest that MPO contains copper and pyrroloquinoline quinone, as found for typical diamine oxidases. Davies, et al., Phytochemistry 28:1573-1578 (1989). Roots of tobacco nic mutants, which are defective in regulation of nicotine biosynthesis, contained somewhat lower MPO activity than wild-type tobacco roots, indicating that the NIC regulatory loci might regulate MPO gene expression, although the NIC regulation of MPO activity was not as clear as the tight regulation found for putrescine N-methyltransferase (PMT) activity. Saunders and Bush, Plant Physiol. 64:236-240 (1979). Immunological studies using a putative MPO antiserum suggest that MPO is associated with S-adenosylhomocysteine hydrolase as part of a larger multi-enzyme complex Heim and Jelesko, Plant Mol. Biol. 56:299-308 (2004). However, direct biochemical evidence was missing. Until now, MPO genes have not been molecularly cloned from tobacco and other solanaceous plants that synthesize N-methylputrescine-derived alkaloids.

Four lines of evidence indicate that the inventive MPO genes, MPO1 and MPO2, are involved in the oxidation of methylputrescine and nicotine biosynthesis in tobacco. First, the MPO1 and MPO2 genes are regulated by the nicotine regulatory NIC loci, in the same way as other genes encoding nicotine biosynthetic enzymes, such as PMT, QPT, A622, and NBB1. Second, the MPO1 and MPO2 genes are expressed exclusively in tobacco roots, as are PMT, QPT, A622, and NBB1. Third, like PMT, QPT, A622, and NBB1, MPO1 and MPO2 expression is up-regulated by treatment with methyljasmonate. Fourth, recombinant MPO1 oxidizes N-methylputrescine more efficiently than putrescine and cadaverine. The enzymatic property is the same for MPO enzymes partially purified from roots of N. tabacum and N. rustica. Thus, the two novel genes, MPO1 and MPO2, identified and cloned by the inventors, have a critical role during nicotine biosynthesis in Nicotiana.

Plants of the Solanaceae, Erythroxylaceae, and Convolvulaceae synthesize N-methylputrescine-derived alkaloids, such as nicotine, hyoscyamine, scopolamine, atropine and cocaine. Accordingly, the present invention encompasses both methodology and constructs for regulating alkaloids in a plant, by increasing or decreasing at least one of MPO1 and MPO2. That is, levels of nicotine and some other nicotinic alkaloids in tobacco can be decreased or increased by regulating at least one of MPO1 and MPO2. Pursuant to this aspect of the invention, a plant, or any part thereof, is transformed with a nucleotide sequence, expression of which suppresses or up-regulates at least one of MPO1 and MPO2 and reduces or increases alkaloid content, respectively.

Definitions

All technical terms employed in this specification are commonly used in biochemistry, molecular biology and agriculture; hence, they are understood by those skilled in the field to which this invention belongs. Those technical terms can be found, for example in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed., Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, 5th ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; TOBACCO: PRODUCTION, CHEMISTRY AND TECHNOLOGY, D. L. Davis and M. T. Nielson (eds.); Wiley, 1999.

Methodology involving plant biology techniques are described here and also are described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, for example, in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, $2^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, MA. Methods for chemical synthesis of nucleic acids are discussed, for example, in Beaucage & Caruthers, Tetra. Letts. 22:1859-62 (1981), and Matteucci & Caruthers, J. Am. Chem. Soc. 103: 3185 (1981).

Restriction enzyme digestions, phosphorylations, ligations, and transformations were done as described in Sambrook et al., MOLECULAR CLONING: A LABORATORY MANUAL, 2nd ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.) unless otherwise specified.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequences encoding MPO1 and MPO2, respectively, which do not substantially affect the functional properties of either enzyme are contemplated.

Gene refers to a polynucleotide sequence that comprises control and coding sequences necessary for the production of a polypeptide or precursor. The polypeptide can be encoded by a full-length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

As is conventional in the art, nucleotide sequences may be denoted by italicized font (e.g., *PMT*), whereas polypeptide sequences are not italicized (e.g., PMT).

NIC1 and NIC2 loci are two independent genetic loci in *N. tabacum*, formerly designated as A and B. Mutations nic1 and nic2 reduce expression levels of nicotine biosynthesis enzymes and nicotine content, generally the nicotine content of wild type>homozygous nic2>homozygous nic1>homoyzgous nic1 and homozygous nic2 plants. Legg & Collins, Can. J. Cyto. 13:287 (1971); Hibi et al., Plant Cell 6:723-735 (1994); Reed & Jelesko, Plant Science 167:1123 (2004).

As used herein, "expression" denotes the production of the protein product encoded by a nucleotide sequence. "MPO1 expression" refers to biosynthesis of a gene product encoded by SEQ ID NO: 1. "MPO2 expression" refers to biosynthesis of a gene product encoded by SEQ ID NO: 3. "MPO expression" refers to biosynthesis of a gene product encoded by SEQ ID NO: 1 and biosynthesis of a gene product encoded by SEQ ID NO: 3.

The terms "suppression" or "reduction" or "down-regulation" are used synonymously to indicate that expression of a particular gene sequence, or variant thereof, in a cell or plant, including all progeny plants derived thereof, has been reduced, relative to a control cell or plant.

MPO1 suppression denotes a reduction of MPO1 expression in an organism such as a cell or plant, relative to a control cell or plant. MPO1 suppression includes the biosynthesis of a gene product encoded by SEQ ID NO: 1, any related ORF sequence, and all MPO1 polynucleotide variants.

MPO2 suppression denotes a reduction of MPO2 expression in an organism such as a cell or plant, relative to a control cell or plant. MPO2 suppression includes the biosynthesis of a gene product encoded by SEQ ID NO: 3, any related ORF sequence, and all MPO2 polynucleotide variants.

MPO suppression refers to a reduction of both MPO1 and MPO2 expression in the same organism such as a cell or plant, relative to a control cell or plant.

MPO1 and MPO2 belong to the sub-group of the larger enzyme family of copper containing diamine oxidases. Typically, these "regular" diamine oxidases prefer symmetric diamines over N-methylated diamines for substrates. Although the DNA sequences of regular tobacco diamine oxidases are not known, it is likely that several nucleotide segments are common to MPO1 or MPO2 and regular tobacco diamine oxidases. If a full-length MPO-encoding polynucleotide, MPO ORF, or an MPO nucleotide fragment of at least 15 nucleotides, or variants of any the foregoing, is utilized for the suppression of one or both of the MPO genes, suppression of regular diamine oxidase genes may also occur.

It is therefore an object of the present invention, that if MPO suppression is desired without the co-suppression of the regular diamine oxidases, segments of the 3'- or 5'-untranslated regions of MPO1 and/or MPO2 genes are utilized for these specific sequences in tandem to precisely target the MPO gene(s). Co-suppression of related-family member genes and specific suppression of target genes by gene-specific regions have been reported in RNAi suppression of rice Rac gene family members. See Miki D, Itoh R, Shimamoto K, *Plant Physiol.* 138:1903-1913, 2005, which is incorporated herein by reference.

"Overexpression" or "up-regulation" or "increased expression" are used synonymously to indicate that expression of a particular gene sequence, or variant thereof, in a cell or plant, including all progeny plants derived thereof, has been increased, relative to a control cell or plant.

"MPO1 overexpression" denotes an increasing of MPO1 expression in an organism such as a cell or plant, relative to a control cell or plant. MPO1 overexpression includes the biosynthesis of a gene product encoded by SEQ ID NO: 1, any related ORF sequence, and all MPO1 polynucleotide variants.

"MPO2 overexpression" denotes an increasing of MPO2 expression in an organism such as a cell or plant, relative to a control cell or plant. MPO2 overexpression includes the biosynthesis of a gene product encoded by SEQ ID NO: 3, any related ORF sequence, and all MPO2 polynucleotide variants.

"MPO overexpression" refers to an increase of both MPO1 and MPO2 expression in the same organism such as a cell or plant, relative to a control cell or plant.

MPO1, MPO2, and MPO suppression and overexpression have the ability to regulate (decrease or increase) nicotine biosynthesis in *N. tabacum*, the most preferred plant. MPO suppression and overexpression also have the ability to regulate (decrease or increase) nicotine biosynthesis in other nicotine-producing plants. Preferred nicotine-producing plants include *Nicotiana*, *Duboisia*, *Anthocercis* and *Salpiglessis* genera in the Solanaceae or the *Eclipta* and *Zinnia* genera in the Compositae.

An "alkaloid" is a nitrogen-containing basic compound found in plants and produced by secondary metabolism. A "nicotinic alkaloid" is nicotine or an alkaloid that is structurally related to nicotine and that is synthesized from a compound produced in the nicotine biosynthesis pathway. As used herein and in the case of tobacco, "nicotinic alkaloid content," "total alkaloid content" and "total alkaloids" are synonymous and mean the total levels of alkaloids found in a tobacco plant, for example, in terms of pg/g dry weight (DW). For non-tobacco plants "total alkaloid content" and "total alkaloids" are synonymous and mean the total levels of alkaloids found in a plant, for example, in terms of pg/g dry weight (DW).

"Alkaloid biosynthesis genes," are genes that encode alkaloid biosynthesis enzymes and many are known. Additionally, about 12,000 chemical structures are currently known as alkaloids. Exemplary alkaloid biosynthesis enzymes include Tropinone reductase-I, Tropinone reductase-II and Hyoscyamine 6b-hydroxylase, which are involved in tropane alkaloid biosynthesis. Hashimoto and Yamada, *Current Opinion in Biotechnology,* 14:163-168 (2003), which is incorporated herein by reference.

Illustrative nicotinic alkaloids include but are not limited to nicotine, nornicotine, anatabine, anabasine, anatalline, N-methylanatabine, N-methylanabasine, myosmine, anabaseine, N'-formylnornicotine, nicotyrine, and cotinine. Other very minor nicotinic alkaloids in tobacco leaf are reported, for example, in Hecht, S. S. et al., *Accounts of Chemical Research* 12:92-98 (1979); Tso, T. C., Production, *Physiology and Biochemistry of Tobacco Plant.* Ideals Inc., Beltsville, MD (1990). The chemical structures of several alkaloids are presented, for example, in Felpin et al., *J. Org. Chem.* 66:6305-6312 (2001).

"Anatabine" is formed in tobacco from two molecules of a metabolite of nicotinic acid. Leete and Slattery, *J. Am. Chem. Soc.* 98:6326-6330 (1976). Since this proposed biosynthetic pathway does not involve a diamine oxidation step, diamine oxidase or MPO do not seem to be involved in the formation of anatabine. Previous studies have demonstrated that PMT suppression reduces nicotine content but increases putrescine and anatabine levels. Chintapakorn & Hamill, *Plant Mol. Biol.* 53:87-105 (2003); Sato et al., Proc. Natl. Acad. Sci. USA 98, 367-372. (2001); Steppuhn, A., et al., *PLoS Biol* 2(8):e217:1074-1080 (2004). Accordingly, the MPO genes of the present invention likely do not contribute to the formation of anatabine. Increasing MPO expression may decrease anatabine accumulation, apparently by competitive use of a common precursor in the formation of nicotine and other alkaloids.

Anabasine and anatalline contain a piperidine moiety. The piperidine moiety of anabasine is thought to be derived from cadaverine via delta-1-piperidine in tobacco. Watson AB, Brown, *J. Chem. Soc. Perkin Trans.* 1:2607-2610 (1990). The conversion from cadaverine to delta-1-piperidine can be catalyzed by diamine oxidase Hashimoto et al., *Plant Physiol.* 93:216-221 (1990). Cadaverine is a good substrate for general diamine oxidases but is also a substrate for MPO, although it has a lower affinity than N-methylated diamines. Hashimoto et al., id; Walton and McLauchlan, *Phytochemistry* 29:1455-1457 (1990); Boswell et al., *Phytochemistry* 52:871-878 (1999). The MPO genes of the present invention may therefore contribute to the formation of anabasine and anatalline.

Many other pyridyl bases plus many derivatives of nornicotine, anatabine, and anabasine are nicotinic alkaloids that have been reported to be present in tobacco and for purposes of the invention shall be included within minor *Nicotiana* alkaloids or nicotinic alkaloids. Most of these so-called "minor nicotinic alkaloids" are present in less than 50 µg/g (dry weight basis) and many others are present in nanogram amounts. Bush, L. P., et al., "Biosynthesis and metabolism in nicotine and related alkaloids" in NICOTINE AND RELATED ALKALOIDS, J. W. Gorrod & J. Wahren (eds.) Chapman & Hall, London (1993); Bush, L. P., et al., "Alkaloid Biosynthesis" in TOBACCO PRODUCTION CHEMISTRY AND TECHNOLOGY. L. Davis and M. T. Nielson (eds.) Wiley, 1999.

"Nicotine" is the primary alkaloid in *N. tabacum* along with 50-60 percent of other species of *Nicotiana*. Based on alkaloid accumulation in the leaves, nornicotine, anatabine, and anabasine are the other foremost alkaloids in *N. tabacum*. Anatabine is usually not the primary alkaloid in any species but does accumulate to relatively higher amounts in 3 species; anabasine is the primary alkaloid in four species. Nornicotine is the primary alkaloid in 30 to 40 percent of *Nicotiana* species. Depending on the variety, about 85 to about 95 percent of total alkaloids in *N. tabacum* is nicotine. Bush, L. P., et al., "Alkaloid Biosynthesis" in Tobacco Production, Chemistry and Technology, D. L. Davis and M.

T. Nielson (eds.) Wiley pp. 285-291 (1999); Hoffmann, et al., *Journal of Toxicology and Environmental Health,* 41:1-52, (1994).

A "reduced-nicotine plant" encompasses a plant that contains less than half, preferably less than 25%, and more preferably less than 20% or less than 10% of the nicotine content of a control plant of the same variety. A reduced-nicotine plant also includes a plant (*Nicotiana, Duboisia, Solanum, Anthocercis* and *Salpiglessis* genera in the Solanaceae or the *Eclipta* and *Zinnia* genera in the Compositae) that contains less nicotine compared with a control plant of the same variety.

A "reduced-alkaloid" plant encompasses a plant that contains less than half, preferably less than 25%, and more preferably less than 20% or less than 10% of the "total alkaloid content" of a control plant of the same variety.

A "reduced-anabasine" plant encompasses a plant that contains less than half, preferably less than 25%, and more preferably less than 20% or less than 10% of the anabasine content of a control plant of the same variety.

A "reduced-anatalline" plant encompasses a plant that contains less than half, preferably less than 25%, and more preferably less than 20% or less than 10% of the anatalline content of control plant of the same variety.

A "reduced-nornicotine" plant encompasses a plant that contains less than half, preferably less than 25%, and more preferably less than 20% or less than 10% of the anatalline content of a control plant of the same variety.

A "reduced-anatabine" plant encompasses a plant that contains less than half, preferably less than 25%, and more preferably less than 20% or less than 10% of the anatabine content of a control plant of the same variety.

I. Nicotinic Alkaloid Reduction (Down-Regulation)

A. Decreasing *Nicotiana* Nicotinic Alkaloids by Suppressing at Least One of MPO1 and MPO2

Because MPO is a critical enzyme in the biosynthesis of nicotinic alkaloids, the inventive MPO sequences can be used for regulating nicotinic alkaloids. That is, nicotinic alkaloid content may be decreased by suppressing at least one of MPO1 and MPO2. Accordingly, the present invention provides methodology and constructs for decreasing nicotinic alkaloid content in a *Nicotiana* plant, by suppressing at least one of MPO1 or MPO2 Suppressing both MPO1 and MPO2 may further decrease nicotinic alkaloids levels in a *Nicotiana* plant.

B. Decreasing *Nicotiana* Nicotinic Alkaloids by Suppressing at Least One of MPO1 and MPO2 and at Least One of A622, NBBI, QPT, and PMT Previous reports indicate that suppressing more than one nicotine biosynthesis gene in *Nicotiana* decreases nicotinic alkaloid content further than suppressing one. For example, suppressing both A622 and NBB1 further reduces nicotine levels than suppressing either A622 or NBB1. See WO/2006/109197. Accordingly, the present invention contemplates further decreasing nicotinic alkaloid content by suppressing at least one of MPO1 and MOP2 and one or more of A622, NBB1, QPT, and PMT in *Nicotiana*. Pursuant to this aspect of the invention, a nucleic acid construct comprising a segment of at least one of MPO1 and MOP2 and one or more of A622, NBB1, QPT, and PMT is introduced into a *Nicotiana* cell or plant. An illustrative nucleic acid construct may comprise segments of both MPO1 and QPT.

II. Nicotinic Alkaloid Biosynthesis (Up-Regulation)

A. Increasing *Nicotiana* Nicotinic Alkaloids by Overexpressing at Least One of MPO1 and MPO2

The present invention also relates to increasing nicotinic alkaloids in *Nicotiana* plants by overexpressing at least one of MPO1 and MPO2. Accordingly, the present invention provides methodology and constructs for increasing nicotinic alkaloid content in a *Nicotiana* plant, by overexpressing at least one of MPO1 and MPO2. Overexpressing at least one of MPO and MPO2 to further increase nicotinic alkaloid levels in a *Nicotiana* plant is similar to the methodology in Examples 7 and 8 of the present invention.

B. Increasing *Nicotiana* Nicotinic Alkaloids by Overexpressing at Least One of MPO1 and MPO2, and at Least One of PMT, QPT, A622, and NBB1

The only previous report demonstrating overexpression of a nicotinic biosynthesis gene in any *Nicotiana* species was in *N. sylvestris*, where PMT overexpression resulted in a modest 40% increase in leaf nicotine. Sato et al., *Proc. Nat'l Acad. Sci. USA* 98:367-72 (2001). While overexpressing a nicotinic alkaloid biosynthesis gene in one plant species, such as *N. sylvestris*, results in an increased accumulation of secondary metabolites, it does not necessarily follow that similar accumulation of secondary metabolites will occur in a related species, such as *N. tabacum*. Saitoh et al., *Phytochemistry* 24:477-80 (1985). This is especially relevant for PMT overexpression, since *N. tabacum* contains five expressed PMT genes and *N. sylvestris* contains three expressed PMT genes. Hashimoto et al., *Plant Mol. Biol.* 37:25-37 (1998); Reichers & Timko, *Plant Mol. Biol.* 41:387-401 (1999).

Indeed, when the PMT gene from *N. tabacum* was overexpressed in *Duboisia* hairy root cultures, the levels of nicotine, hyoscyamine, and scopolamine did not increase significantly. Moyano et al., *Phytochemistry* 59, 697-702 (2002). Likewise, overexpressing the same PMT gene in transgenic plants and hairy root cultures of *Atropa belladonna* did not affect hyoscyamine and scopolamine levels. Sato et al., *Proc. Nat'l Acad. Sci.* USA 98:367-72 (2001); Rothe et al., *J. Exp. Bot.* 54:2065-070 (2003).

In Solanaceous species, such as tobacco, evidence suggests that the same alkaloid biosynthesis pathway in two related plant species can be regulated differently and overexpression of a given gene does not necessarily lead to a similar accumulation pattern of secondary metabolites. Moyano et al., *J. Exp. Bot.* 54:203-11 (2003). For example, when sixty *Nicotiana* species were analyzed, there was considerable variation in total alkaloid content and alkaloid profile amongst the species. Saitoh et al., *Phytochemistry* 24:477-80 (1985).

For instance, while *N. sylvestris* had the highest dry weight content of total alkaloids (the sum of nicotine, nornicotine, anabasine and anatabine) at 29,600 pg/g or 2.96 percent, *N. alata* contained the lowest at 20 pg/g or 0.002 percent. The ratio of nicotine to total alkaloids in the leaves of *N. sylvestris* was about 80 percent versus about 95 percent for *N. tabacum*. Id. Also, the ratio of nornicotine to total alkaloid in *N. sylvestris* leaves was 19.1 percent versus 3 percent for *N. tabacum*

Based on these large variations among the sixty *Nicotiana* species, Saitoh et al. conclude that the "amount and ratio of total and individual alkaloids present in a plant depend on the species. No clear-cut correlation between alkaloid pattern and classification of the genus *Nicotiana* seems to exist." Id. at page 477.

Members of the *Nicotiana* genus can also differ in evolutionary orgin and other characteristics. See Clarkson et al., *New Phytologist* 168:241-252 (2005). For example, *N. tabacum* is an allotetraploid, has 24 chromosomes, and is believed to originate from *N. sylvestris* (n=12) and *N.*

*tomentosiformis* (n=12). *N. benthamiana*, indigenous to Australia, is also an allotetraploid species, but it has 38 chromosomes and is thought to be the result of the hybridization of *N. suaveolens* (n=16) and *N. debneyi* (n=24). *N. tabacum* has about three fold the total alkaloid content of *N. benthamiana* and *N. tabacum* has a greater percentage of its total alkaloid content as nicotine. Saitoh et al., *Phytochemistry* 24:477-80 (1985).

It may be desirable, therefore, to overexpress different combinations of nicotinic alkaloid biosynthesis genes in different species of *Nicotiana* to produce elevated amounts of particular alkaloids. PMT, QPT, A622 and NBB up-regulation in *N. tabacum* increases nicotine biosynthesis. Nicotine can be further increased by genetically engineering more than one gene in the nicotine biosynthesis pathway. See WO2007/072224.

Therefore, the present invention contemplates further increases of nicotine synthesis in *N. tabacum* by overexpressing at least one of MPO1 and MPO2, and at least one of A622, NBB1, QPT, and PMT. Pursuant to this aspect of the invention, a nucleic acid construct comprising at least one of MPO1 and MPO2, and at least one of A622, NBB1, QPT, and PMT is introduced into a *Nicotiana* plant cell. An illustrative nucleic acid construct may comprise, for example, both MPO1 and PMT. See FIG. 6D. Similarly, for example, a genetically engineered plant overexpressing MPO1 and PMT may be produced by crossing a transgenic plant overexpressing MPO1 with a transgenic plant overexpressing PMT. Following successive rounds of crossing and selection, a genetically engineered plant having overexpressing MPO1 and PMT can be selected.

C. Increasing *Nicotiana* Nicotinic Alkaloids and Yield

Increased nicotine plants of the invention may be produced by conventional breeding or crossing, as described by Wernsman et al., in PRINCIPLES OF CULTIVAR DEVELOPMENT—Vol. 2: CROP SPECIES (WR Fehr (ed.), Macmillan, 1997). For example, a stable genetically engineered transformant, regenerated from tobacco material that contains a suitable transgene, is employed to introgress a high-nicotine trait into a desirable commercially acceptable genetic background, thereby obtaining a tobacco cultivar or variety that combines a high nicotine level with the desirable background.

While any desirable gene can be introgressed into a high-nicotine variety, there is a critical need for introducing a high nicotine trait into a high-yielding tobacco background. Several studies indicate that "Yield improvements have been hampered by the negative relationship that exists with nicotine concentration." (PRODUCTION, CHEMISTRY AND TECHNOLOGY, D. L. Davis and M. T. Nielson (eds.) Wiley (1999), at page 46). In his reflections of tobacco breeding, Wernsman asserts "continued selection for yield alone will soon result in a population whose nicotine concentration in cured leaf is so low that the tobaccos are unacceptable to industry" Wernsman, Recent Advances in Tobacco Science 25:5-35 (1999). He postulates that "genetic methods of up-regulating nicotine synthesis may be needed to permit additional increases in yielding ability while maintaining nicotine concentration" Id.

Accordingly, the present invention provides a means for correcting the "negative correlation" between yield and nicotine content in *Nicotiana* plants by overexpressing a gene encoding a nicotine biosynthesis enzyme in a high-yielding *Nicotiana* plant. Exemplary nicotine biosynthesis enzymes include but are not limited to MPO1, MPO2, QPT, PMT, A622, NBB1, arginine decarboxylase (ADC), NADH dehydrogenase, ornithine decarboxylase (ODC), and S-adenosyl-methionine synthetase (SAMS). Increased-nicotine plants resulting therefrom are then crossed with any desirable commercially acceptable genetic background that maintains high yield. Suitable high-yield *Nicotiana* plants include but are not limited to *Nicotiana tabacum* cultivars K326, NC71, NC72 and RG81. Following successive rounds of crossing and selection, a genetically engineered plant having increased nicotine and increased yield is accordingly produced.

A further aspect of the invention provides crossing an increased-nicotine plant with an increased-yield plant as another strategy for breaking the negative correlation between nicotine content and yield.

"Increased yield genes" encompass any gene whose expression correlates with increased production capacity as reflected by, for example, increased photoassimilate production, increased growth rate, improved vigor, enhanced yield, enhanced $CO_2$ fixation, enhanced biomass, increased seed production, improved storage, enhanced yield, increased disease tolerance, increased insect tolerance, increased water-stress tolerance, enhanced sweetness, improved starch composition, improved sucrose accumulation and export, and improved response to oxidative stress compared with a wild-type control plant.

Likewise, an "increased yield plant" refers to a plant, or any portion thereof, overexpressing an "increased yield gene" and exhibits increased production capacity as reflected by, for example, increased photoassimilate production, increased growth rate, improved vigor, enhanced yield, enhanced $CO_2$ fixation, enhanced biomass, increased seed production, improved storage, enhanced yield, increased disease tolerance, increased insect tolerance, increased water-stress tolerance, enhanced sweetness, improved starch composition, improved sucrose accumulation and export, and improved response to oxidative stress compared with a wild-type control plant.

For example, and in no way limiting the invention, an increased yield plant can be produced by overexpressing a pathogenesis-related (PR) gene. It has been shown that overexpressing a maize PRms gene, in tobacco produced transgenic tobacco plants having enhanced biomass and seed production. See Murillo et al., *Plant* 36:330-41 (2003), which is incorporated herein by reference. Likewise, an increased yield plant can be produced by overexpressing a gene encoding a Calvin cycle enzyme. See Tamoi et al. *Plant Cell Physiol.* 47(3)380-390 (2006), which is incorporated herein by reference. Tobacco plants overexpressing, for example, a cyanobacterial fructose-1,6-/sedoheptulose-1,7-bisphosphatase displayed enhanced photosynthetic efficiency and growth efficiency compared with wild-type tobacco. See Miyagawa et al., *Nature Biotech.* 19:965-69 (2001).

The present invention also contemplates producing a plant having increased yield and increased nicotine by overexpressing a gene encoding a nicotine biosynthesis enzyme, such as MPO1, MPO2, QPT, PMT, A622, or NBB1, and overexpressing an increased yield gene, such as genes encoding PRms, fructose-1,6-/sedoheptulose-1,7-bisphosphatase, fructose-1,6-bisphosphatase, and sedoheptulose-1, 7-bisphosphatase, sedoheptulose-1,7-bisphosphatase in the same plant or cell.

D. Producing Nicotinic Alkaloids and Related Compounds in Non-Nicotine Producing Cells At least one of MPO1 and MPO2 can be introduced into a non-nicotine producing plant or cell, thereby producing nicotine or related compounds in an organism or cell that does not produce these compounds otherwise. A variety of products can be produced from these engineered organisms and cells, including nicotine, nicotine precursors, nicotine analogs, and nicotine biosynthesis enzymes.

A "non-nicotine producing plant" refers to any plant that does not produce nicotine or related nicotinic alkaloids. Illustrative non-nicotine producing plants include but are not limited to *Atropa belladonna* and *Arabidopsis thaliana*.

"Non-nicotine producing cells" refers to cells from any organism that does not produce nicotine or related nicotinic alkaloids. Illustrative cells include but are not limited to plant cells, such as *Atropa belladonna, Arabidopsis thaliana*, as well as insect, mammalian, yeast, fungal, algal, or bacterial cells.

A "nicotine analog" has the basic structure of nicotine but may, for example, have different ring substituents. For example, a nicotine analog may substitute a hydrogen (—H) for the methyl group (—CH3) thereby producing nornicotine, which is an analog of nicotine. In addition to sharing a similar structure with nicotine, nicotine analogs may provide similar physiological effects. Cotinine, for example, has been cited for its positive effects on improving concentration and memory and, accordingly, is a nicotine analog. Accordingly, nicotine analogs are defined broadly to cover any and all compounds having similar structural and functional activity to nicotine.

III. Nicotinic Alkaloid Ratio Regulation

In addition to (a) suppressing nicotine biosynthesis gene(s) to produce reduced-nicotine tobacco plants and products or (b) up-regulating nicotine biosynthesis gene(s) to produce increased-nicotine tobacco plants and products, an object of the present invention is to alter the ratio of nicotine-to-total alkaloid content of plants, *N. tabacum* plants being preferred, thus changing the alkaloid profile of a plant. The total alkaloid content may be approximately the same, or may be higher or lower.

For example, nicotine and anatabine are formed by the addition of different heterocyclic rings to the same pyridine precursor derived from nicotinic acid. See FIG. 1A. Increasing the level of N-methylpyrrolinium ion increases the ratio of the nicotine-specific precursor N-methylpyrrolinium ion to the common pyridine precursor and also the ratio of the N-methylpyrrolinium ion to the anatabine specific precursor 3,6-dihydropyridine, resulting in an increase in the ratio of nicotine to anatabine. The level of N-methylpyrrolinium ion can be increased by upregulating at least one of MPO1, MPO2 and PMT Additionally, the ratio of N-methylpyrrolinium ion to the common pyridine precursor may be further increased by suppressing a gene encoding an enzyme required for synthesis of nicotinic acid, such as QPT. For example, since the specific precursor of anatabine, 3,6-dhydropyridine, is also derived from nicotinic acid this will also increase the ratio of the nicotine-specific precursor to the anatabine-specific precursor.

As pertaining to traditional tobacco products such as snus, an advantage of genetically engineering a tobacco plant's alkaloid profile in which nicotinic alkaloids levels other than nicotine are reduced is that certain TSNAs, such as N'-nitrosoanatabine (NAT) and N'-nitrosoanabasine (NAB) are reduced. Xie et al. (2004); Djordjevic et al., *J. Agric. Food Chem.*, 37:752-756 (1989).

IV. Products

A. Reduced Nicotine Products

Reducing total alkaloid content in tobacco would increase the value of tobacco as a biomass resource. When grown under conditions that maximize biomass, such as high density and multiple cuttings, tobacco can yield more than 8 tons dry weight per acre, which is comparable with other crops used for biomass. Large-scale growing and processing of conventional tobacco biomass has several drawbacks, however. For example, significant time and energy is spent extracting, isolating, and disposing tobacco alkaloids because conventional tobacco biomass, depending on the variety, contains about 1 to about 5 percent alkaloids. On a per acre basis, conventional tobacco biomass contains approximately as much as 800 pounds of alkaloids. Also, people handling tobacco may suffer from overexposure to nicotine, commonly referred to as "green tobacco disease."

An additional use of reduced-nicotine tobacco is for smoking cessation. More successful methods are needed to assist smokers in quitting smoking. Nicotine replacement therapy (NRT) is not very effective as a smoking cessation treatment because its success rate is less than 20 percent after 6 to 12-months from the end of the nicotine replacement period. Bohadana et al., *Arch Intern. Med.* 160:3 128-3 134 (2000); Croghan et al., *Nicotine Tobacco Res.* 5:18 1-1 87 (2003); Stapleton et al., *Addiction* 90:3 1-42 (1995). Nicotine-reduced or nicotine-free tobacco cigarettes have assisted smokers in quitting smoking successfully, by weaning the smoker from nicotine yet allowing the smoker to perform the smoking ritual. Additionally, denicotinized cigarettes relieve craving and other smoking withdrawal symptoms. See Rose, *Psychopharmacology* 184:274-285 (2006) and Rose et al., *Nicotine Tobacco Res.* 8:89-101 (2006).

B. Increased Nicotine Products

In addition to the more traditional applications for increased nicotine products, such as cigarettes and other tobacco products, recent pharmacological studies suggest a therapeutic role for nicotine and related compounds. For example, several research groups are presently studying drugs that target nicotine receptors as a means for treating cognitive impairments, such as Alzheimer's disease, schizophrenia, and age-related memory loss. Singer, E., "The Upside to Nicotine," *Technology Review* (Jul. 28, 2006). Acetylcholine receptor ligands, such as nicotine, have been demonstrated to have effects on attention, cognition, appetite, substance abuse, memory, extra pyramidal function, cardiovascular function, pain, and gastrointestinal motility and function. U.S. Pat. No. 5,852,041. Accordingly, there are therapeutic benefits of nicotine and related compounds, and thus there is a need for improved methods for producing them.

V. Synthesis of Compounds Using Novel Enzymes

Recently, there has been great interest in synthesizing nicotine analogs that target nicotine receptors and provide therapeutic effects for neurogenerative diseases and cognitive disabilities. For example, Targacept, a pharmaceutical company formed as a spinout from R. J. Reynolds Tobacco Company, endeavors to develop and commercialize nicotine analog drugs based on selective activation of neuronal nicotinic acetylcholine receptors (NNRs). The present invention provides novel nucleic acids encoding nicotine biosynthesis enzymes, which may be valuable in using at least one of MPO1 and MPO2, or at least two of MPO1, MPO2, A622, NBB1, QPT, or PMT, for developing novel nicotine analogs. For example, using the inventive methods and constructs, a nicotinic alkaloid analog can be produced by providing a nicotine analog precursor in a cell culture system comprising cells overexpressing at least one of MPO1 and MPO2.

Additionally, the enzymes produced from the inventive nucleic acid sequences may be used for in vitro synthesis of nicotine and related compounds. That is, recombinant MPO1 and MPO2 can be used for the synthesis or partial synthesis of a nicotinic alkaloid and a nicotinic alkaloid analog.

The enzymes produced from the inventive nucleic acid sequences may be used for synthesizing alkaloids other than nicotinic alkaloids, including tropane alkaloids, as well as precursors of such alkaloids, and analogs of such alkaloids and alkaloid precursors.

MPO enzymes are known to accept, to varying degrees, substrates other than N-methylputrescine. Hashimoto et al., *Plant Physiol.* 93:216 (1990); Walton et al., *Phytochemistry* 29:1455 (1990); McLauchlan et al., *Planta* 191:440 (1993); Boswell et al., *Phytochemistry* 52:855 (1999).

Nicotinic Alkaloid Biosynthesis Sequences

Nicotinic alkaloid biosynthesis genes have been identified in several plant species, exemplified by *Nicotiana* plants. Accordingly, the present invention embraces any nucleic acid, gene, polynucleotide, DNA, RNA, mRNA, or cDNA molecule that is isolated from the genome of a plant species, or produced synthetically, that increases *Nicotiana* nicotinic alkaloid biosynthesis. Additionally, expression of such nicotinic alkaloid biosynthesis sequence produces nicotinic alkaloids in a non-nicotine producing cell, such as an insect cell. The DNA or RNA may be double-stranded or single-stranded. Single-stranded DNA may be the coding strand, also known as the sense strand, or it may be the non-coding strand, also called the antisense strand.

It is understood that the terms MPO1 and MPO2 designate the sequences set forth in SEQ ID NO: 1 and 3, respectively, as well as nucleic acid molecules comprised of variants of SEQ ID NO: 1 and 3, with one or more bases deleted, substituted, inserted, or added, which variant codes for a polypeptide with nicotinic alkaloid biosynthesis activity. Accordingly, sequences having "base sequences with one or more bases deleted, substituted, inserted, or added" retain physiological activity even when the encoded amino acid sequence has one or more amino acids substituted, deleted, inserted, or added. Additionally, multiple forms of MPO1 and MPO2 may exist, which may be due to post-translational modification of a gene product, or to multiple forms of the respective MPO1 or MPO2, genes. Nucleotide sequences that have such modifications and that code for a nicotinic alkaloid biosynthesis enzyme are included within the scope of the present invention.

For example, the poly A tail or 5'- or 3'-end, nontranslation regions may be deleted, and bases may be deleted to the extent that amino acids are deleted. Bases may also be substituted, as long as no frame shift results. Bases also may be "added" to the extent that amino acids are added. It is essential, however, that any such modification does not result in the loss of nicotinic alkaloid biosynthesis enzyme activity. A modified DNA in this context can be obtained by modifying the DNA base sequences of the invention so that amino acids at specific sites are substituted, deleted, inserted, or added by site-specific mutagenesis, for example. Zoller & Smith, *Nucleic Acid Res.* 10:6487-500 (1982).

A nicotinic alkaloid biosynthesis sequence can be synthesized ab initio from the appropriate bases, for example, by using an appropriate protein sequence disclosed herein as a guide to create a DNA molecule that, though different from the native DNA sequence, results in the production of a protein with the same or similar amino acid sequence. This type of synthetic DNA molecule is useful when introducing a DNA sequence into a non-plant cell, coding for a heterologous protein, that reflects different (non-plant) codon usage frequencies and, if used unmodified, can result in inefficient translation by the host cell.

By "isolated" nucleic acid molecule(s) is intended a nucleic acid molecule, DNA or RNA, which has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules, according to the present invention, further include such molecules produced synthetically.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

In contrast, "endogenous nucleic acid" refers to a nucleic acid, gene, polynucleotide, DNA, RNA, mRNA, or cDNA molecule that is present in the genome of a plant or organism that is to be genetically engineered. An endogenous sequence is "native" to, i.e., indigenous to, the plant or organism that is to be genetically engineered.

"Heterologous nucleic acid" refers to a nucleic acid, DNA or RNA, which has been introduced into a cell (or the cell's ancestor) which is not a copy of a sequence naturally found in the cell into which it is introduced. Such heterologous nucleic acid may comprise segments that are a copy of a sequence which is naturally found in the cell into which it has been introduced, or fragments thereof.

A "chimeric nucleic acid" comprises a coding sequence or fragment thereof linked to a transcription initiation region that is different from the transcription initiation region with which it is associated in cells in which the coding sequence occurs naturally.

Unless otherwise indicated, all nucleotide sequences determined by sequencing a DNA molecule herein were determined using an automated DNA sequencer, such as the Model 373 from Applied Biosystems, Inc. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

For the purpose of the invention, two sequences hybridize when they form a double-stranded complex in a hybridization solution of 6×SSC, 0.5% SDS, 5×Denhardt's solution and 100 pg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 μg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

"Sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties, such as charge and hydrophobicity, and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4:11-17 (1988), as implemented in the program PC/GENE (Intelligenetics, Mountain View, California, USA).

Use in this description of a percentage of sequence identity denotes a value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present application is directed to such nucleic acid molecules which are at least 60%, 65%, 70%, 75%, 80%, 85%, 90%, 95%, 96%, 97%, 98%, 99%, or 100% identical to a nucleic acid sequence described in any of SEQ ID NO: 1, 3. Preferred are nucleic acid molecules which are at least 95%, 96%, 97%, 98%, 99%, or 100% identical to the nucleic acid sequence shown in any of SEQ ID NO: 1, 3. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98%, or 99% identical to a reference nucleotide sequence refers to a comparison made between two molecules using standard algorithms well known in the art and can be determined conventionally using publicly available computer programs such as the BLASTN algorithm. See Altschul et al., *Nucleic Acids Res.* 25: 3389-402 (1997).

The present invention further provides nucleic acid molecules comprising the nucleotide sequence of SEQ ID NOS.: 1,3, respectively, which encode an active nicotine biosynthesis MPO enzyme, wherein the enzyme has amino acid sequence that corresponds to SEQ ID NO.: 2 and 4, respectively, and wherein the protein of the invention encompasses amino acid substitutions, additions and deletions that do not alter the function of the nicotine biosynthesis enzyme.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents.

Methodology for Reducing Alkaloids

In one aspect of the invention, methods are provided for reducing alkaloid levels. While any method may be used for reducing alkaloid levels, the present invention contemplates antisense, sense co-suppression, RNAi, artificial microRNA, ribozyme, and virus-induced gene silencing (VIGS), and targeted mutagenesis approaches.

For example, a heterologous sequence utilized in the antisense methods of the present invention may be selected so as to produce an RNA product complementary to an entire MPO1 or MPO2 mRNA sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA.

Suitable antisense sequences may be from at least about 13 to about 15 nucleotides, at least about 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof.

The particular antisense sequence and the length of the antisense sequence will vary, depending, for example, upon the degree of inhibition desired and the stability of the antisense sequence. Generally available techniques and the information provided in this specification can guide the selection of appropriate MPO1 or MPO2 antisense sequences. With reference to SEQ ID NO: 1 or 3 herein, an oligonucleotide of the invention may be a continuous fragment of MPO1 or MPO2 cDNA sequence in antisense orientation, of any length that is sufficient to achieve the desired effects when transformed into a recipient plant cell.

The present invention may contemplate sense co-suppression of one or both of MPO1 and MPO2. Sense polynucleotides employed in carrying out the present invention are of a length sufficient to suppress, when expressed in a plant cell, the native expression of the plant MPO1 or MPO2 protein in that plant cell. Such sense polynucleotides may be essentially an entire genomic or complementary nucleic acid encoding the MPO1 or MPO2 enzyme, or a fragment thereof, with such fragments typically being at least 15 nucleotides in length. Techniques are generally available for ascertaining the length of sense DNA that results in suppression of the expression of a native gene in a cell.

In an alternate embodiment of the present invention, plant cells are transformed with a nucleic acid construct containing a polynucleotide segment encoding an enzymatic RNA molecule (a "ribozyme"), which enzymatic RNA molecule is directed against (i.e., cleaves) the mRNA transcript of DNA encoding MPO1 or MPO2, as described herein. Ribozymes contain substrate binding domains that bind to accessible regions of the target rnRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif.

Ribozyme cleavage sites within an RNA target may initially be identified by scanning the target molecule for ribozyme cleavage sites (e.g., GUA, GUU or GUC sequences). Once identified, short RNA sequences of 15, 20, 30, or more ribonucleotides corresponding to the region of the target gene containing the cleavage site may be evaluated for predicted structural features.

The suitability of candidate targets also may be evaluated by testing their accessibility to hybridization with complimentary oligonucleotides, using ribonuclease protection assays as are known in the art. DNA encoding enzymatic RNA molecules may be produced in accordance with known techniques. For example, see Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al., U.S. Pat. No. 5,595,877; Wagner et al., U.S. Pat. Nos. 5,591,601; and 5,622,854.

Production of such an enzymatic RNA molecule in a plant cell and disruption of MPO1 or MPO2 protein production reduces protein activity in plant cells, in essentially the same manner as production of an antisense RNA molecule; that is, by disrupting translation of mRNA in the cell which produces the enzyme. The term "ribozyme" describes an RNA-containing nucleic acid that functions as an enzyme, such as an endoribonuclease, and may be used interchangeably with "enzymatic RNA molecule."

The present invention further includes nucleic acids encoding ribozymes, nucleic acids that encode ribozymes and that have been inserted into an expression vector, host cells containing such vectors, and methodology employing ribozymes to decrease MPO1 and MPO2 expression in plants.

In one embodiment, the present invention provides double-stranded nucleic acid molecules of that mediate RNA interference gene silencing. In another embodiment, the siNA molecules of the invention consist of duplex nucleic acid molecules containing about 15 to about 30 base pairs between oligonucleotides comprising about 15 to about 30 (e.g., about 15, 16, 17, 18, 19, 20, 21, 22, 23, 24, 25, 26, 27, 28, 29, or 30) nucleotides. In yet another embodiment, siNA molecules of the invention comprise duplex nucleic acid molecules with overhanging ends of about 1 to about 32 (e.g., about 1, 2, or 3) nucleotides, for example, about 21-nucleotide duplexes with about 19 base pairs and 3'-terminal mononucleotide, dinucleotide, or trinucleotide overhangs. In yet another embodiment, siNA molecules of the invention comprise duplex nucleic acid molecules with blunt ends, where both ends are blunt, or alternatively, where one of the ends is blunt.

An siNA molecule of the present invention may comprise modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

The present invention includes nucleic acids encoding comprising RNAi gene silencing vectors, host cells containing such vectors, and methodology employing RNAi vectors to decrease MPO1 and MPO2 expression in plants. RNAi constructs generate siNA in situ from transcripts that contain segments of target sequences in an inverted repeat orientation, allowing formation of "hairpin" RNAs containing double-stranded regions. Reviews on the design and use of such RNAi constructs include McGinnis et al. *Methods Enzymol.* 392: 1-24 (2005), Watson et al. (*FEBS Lett.* 579:5982-7 (2005), Wesley et al., *Methods Mol. Biol.* 236: 273-86 (2003). RNAi constructs containing segments of target gene sequences ranging from less than 100 nt to more than 800 nt are useful in suppressing genes in plants. Wesley et al., *Plant J.* 27: 581-590 (2001).

Artificial microRNAs, which have double stranded regions comprising target gene sequences of only about 21 bases, are effective for suppression of gene expression in plants. Schwab et al., *Plant Cell* 18: 1121-1133 (2006), Lu et al., *Nucleic Acids Research* 32:e171 (2004) Nucleic acids comprising segments of the MPO1 and MPO2 that are distinct or identical may be incorporated in artificial microRNAs for suppression of MPO1, MPO2, or both MPO1 and MPO2.

The present invention further includes nucleic acids encoding comprising virus-induced gene silencing (VIGS) vectors, host cells containing such vectors, and methodology employing VIGS vectors to decrease MPO1 and MPO2 expression in plants. Liu et al. *The Plant Journal* 30(4), 415-429 (2002).

In one embodiment, the present invention provides VIGS vectors which comprise nucleic acid molecules containing MPO1 or MPO2 oligonucleotides. The MPO1 or MPO2 oligonucleotides may be about 15 to about 30 bases (e.g., about 15, 16, 17, 18, 19, 20, 21, 22, 23, 24, 25, 26, 27, 28, 29, or 30) nucleotides or longer.

Expression may be reduced by introducing a nucleic acid comprising a portion of an MPO1 or MPO2 sequence that causes targeted in situ mutagenesis of an endogenous gene, resulting in its inactivation.

The MPO1 and MPO2 sequences of the present invention can be used in methods for screening for mutations in specific target gene regions. For example, specific primers comprising segments of the MPO1 or MPO2 sequences are used to amplify a region of the corresponding gene in DNA from pools of mutagenized plants, and the presence of mutations within the segment is detected by cleavage of heteroduplexes formed by mutant and wild type sequences (Till et al. *BMC Plant Biol.* 7:19 (2007)). This approach was used to identify mutations in nicotine demethylase. U.S. published patent application 2007/0199097. Alternatively, mutations can be identified by sequencing of the DNAs amplified using the specific primers, or direct sequencing of the DNA from mutagenized plants using primers comprising segments of the MPO1 and MPO2 nucleic acids of the present invention. Mutations in MPO1 and MPO2 can also be detected by hybridizing nucleic acids comprising nucleic acids of the present invention to probes comprising regions of the corresponding genes from mutagenized plants arrayed on microarrays and observing differential hybridization.

The MPO1 and MPO2 sequences of the present invention can be used in oligonucleotide-directed gene repair, in which oligonucleotides, which may be chimeric nucleotides composed of DNA and modified RNA residues, are used to induce mutations at specific target sites. The oligonucleotide mutational vectors may include substitutions of U for T and substitutions of non-natural nucleotide analogs. Zhu et al., *Proc Nat'l Acad Sci USA* 96:8768-73 (1999), Beetham et al., *Proc Nat'l Acad Sci USA* 96:8774-8 (1999); Kipp et al. *Methods Mol Biol* 133:213-21 (2000); Dong et al., *Plant Cell Rep.* 25:457-65 (2006); U.S. Pat. Nos. 6,271,360, 6,479,292, and 7,060,500.

Nucleic Acid Constructs

In accordance with one aspect of the invention, a sequence that suppresses nicotinic alkaloid biosynthesis is incorporated into a nucleic acid construct that is suitable for plant or cell transformation. Thus, such a nucleic acid construct can be used to suppress at least one of MPO1 and MPO2. Further, a nucleic acid construct at can be used to suppress at least one of MPO1 and MPO2 and, in addition, at least one of A622, NBB1, PMT, and QPT in a plant.

In another aspect of the invention, a sequence that increases nicotinic alkaloid biosynthesis is incorporated into a nucleic acid construct that is suitable for plant or cell transformation. Thus, such a nucleic acid construct can be used to overexpress at least one of MPO1 and MPO2 in a plant. Further, such a nucleic acid construct can be used to overexpress at least one of MPO1 and MPO2, and, in addition, at least one of A622 and NBB1, PMT and QPT in a plant, or in a non-nicotine producing cell.

Recombinant nucleic acid constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence then is cloned into a vector containing suitable regulatory elements, such as upstream promoter and downstream terminator sequences.

An important aspect of the present invention is the use of nucleic acid constructs wherein a nicotinic alkaloid biosynthesis-encoding sequence is operably linked to one or more regulatory sequences, which drive expression of the nicotinic alkaloid biosynthesis-encoding sequence in certain cell types, organs, or tissues without unduly affecting normal development or physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to either decrease or increase expression of MPO1, MPO2, A622, NBB1, PMT, or QPT may be constitutive promoters, such as the cauliflower mosaic virus (CaMV) 35S promoter, or tissue specific, tissue-preferred, cell type-specific, and inducible promoters. Preferred promoters include promoters which are active in root tissues, such as the tobacco RB7 promoter (Hsu et al. *Pestic. Sci.* 44:9-19 (1995); U.S. Pat. No. 5,459,252), maize promoter CRWAQ81 (US published patent application 20050097633); the *Arabidopsis* ARSK1 promoter (Hwang and Goodman, Plant J. 8:37-43 (1995)), the maize MR7 promoter (U.S. Pat. No. 5,837,848), the maize ZRP2 promoter (U.S. Pat. No. 5,633,363), the maize MTL promoter (U.S. Pat. Nos. 5,466,785 and 6,018,099) the maize MRS1, MRS2, MRS3, and MRS4 promoters (U.S. Pat. App. 200500 10974), an *Arabidopsis* cryptic promoter (U.S. Pat. App. 20030106105) and promoters that are activated under conditions that result in elevated expression of enzymes involved in nicotine biosynthesis such as the tobacco RD2 promoter (U.S. Pat. No. 5,837,876), PMT promoters (Shoji T. et al., *Plant Cell Physiol.* 41:831-39 (2000b); WO 2002/038588) or an A622 promoter (Shoji T. et al., *Plant Mol Biol.* 50:427-40 (2002)).

The vectors of the invention may also contain termination sequences, which are positioned downstream of the nucleic acid molecules of the invention, such that transcription of mRNA is terminated, and polyA sequences added. Exemplary of such terminators are the cauliflower mosaic virus (CaMV) 35S terminator and the nopaline synthase gene (Tnos) terminator. The expression vector also may contain enhancers, start codons, splicing signal sequences, and targeting sequences.

Expression vectors of the invention may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thyrnidne kinase, xanthine-guanine phospho-ribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, and gentamicin. The construct may also contain the selectable marker gene bar that confers resistance to phosphinothricin (glufosinate) and bialafos. Thompson et al., EMBO J. 9:2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

Plants for Genetic Engineering

The present invention comprehends the genetic manipulation of a *Nicotiana* plant for regulating nicotinic alkaloid synthesis via introducing a polynucleotide sequence that encodes an enzyme in the pathway for nicotinic alkaloid synthesis. Accordingly, the present invention provides methodology and constructs for reducing or increasing nicotinic alkaloid synthesis. Additionally, the invention provides methods for producing nicotinic alkaloids and related compounds in non-nicotine producing plants, such as *Arabidopsis thaliana*.

"Genetically engineered" (GE) encompasses any methodology for introducing a nucleic acid or specific mutation into a host organism For example, a tobacco plant is genetically engineered when it is transformed with a polynucleotide sequence that increases expression of a gene, such as MPO1 or MPO2, and thereby increases nicotine levels. Likewise, a plant is genetically engineered when it is transformed with a polynucleotide sequence that reduces expression of a gene, such as MPO1 or MPO2. In contrast, a tobacco plant that is not transformed with a polynucleotide sequence is a control plant and is referred to as a "nontransformed" plant.

In the present context, the "genetically engineered" category includes "transgenic" plants and cells (see definition, infra), as well as plants and cells produced by means of targeted mutagenesis effected, for example, through the use of chimeric RNA/DNA oligonucleotides, as described by Beetham et al., Proc. Nat'l. Acad. Sci. USA 96:8774-8778 (1999) and Zhu et al., loc. cit. at 8768-8773, or so-called "recombinagenic olionucleobases," as described in PCT application WO 03/013226. Likewise, a genetically engineered plant or cell may be produced by the introduction of a modified virus, which, in turn, causes a genetic modification in the host, with results similar to those produced in a transgenic plant, as described herein. See, e.g., U.S. Pat. No. 4,407,956. Additionally, a genetically engineered plant or cell may be the product of any native approach (i.e., involving no foreign nucleotide sequences), implemented by introducing only nucleic acid sequences derived from the host species or from a sexually compatible species. See, e.g., U.S. published application No. 2004/0107455.

"Plant" is a term that encompasses whole plants, plant organs (e.g. leaves, stems, roots, etc.), seeds, differentiated or undifferentiated plant cells, and progeny of the same. Plant material includes, without limitation, seeds suspension cultures, embryos, meristernatic regions, callus tissues, leaves, roots, shoots, stems, fruit, gametophytes, sporophytes, pollen, and microspores. The class of plants which can be used in the present invention is generally as broad as the class of higher plants amenable to genetic engineering techniques, including both monocotyledonous and dicotyledonous plants, as well as gymnosperms. A preferred nicotine producing plant includes *Nicotiana*, *Duboisia*, *Solanum*, *Anthocercis*, and Salpiglessis genera in the Solanaceae or the *Eclipta* and *Zinnia* genera in the Compositae.

"Tobacco" refers to any plant in the *Nicotiana* genus that produces nicotinic alkaloids. Tobacco also refers to products comprising material produced by a *Nicotiana* plant, and therefore includes, for example, expanded tobacco, reconstituted tobacco, cigarettes, cigars, chewing tobacco or forms of smokeless tobacco, snuff and snus made from GE increased-nicotine tobacco. Examples of *Nicotiana* species include but are not limited to the following: *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana hybrida, Nicotiana ingulba, Nicotiana kawakamii, Nicotiana knightiana, Nicotiana langsdorffiii, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana. tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and *Nicotianaxsanderae*.

The Erythroxylaceae (or coca family) is a family of flowering plants consisting of 4 genera and about 240 species. The best-known species by far is the coca (*Erythroxylum coca*). It has been previously reported that when labeled 4-methylaminobutanal diethyl acetal (an acetal derivative of N-methylpyrrolinium cation) was fed to the leaf of *Erythroxylum coca*, the label was incorporated into the tropane moiety of cocaine. Leete, Planta Med. 56:339-

352 (1990). Therefore, it is reasonable to presume that MPO genes of the present invention are involved in the formation of cocaine.

In the present description, "tobacco hairy roots" refers to tobacco roots that have T-DNA from an Ri plasmid of *Agrobacterium rhizogenes* integrated in the genome and grow in culture without supplementation of auxin and other phytohormones. Tobacco hairy roots produce nicotinic alkaloids as roots of a tobacco plant do. These types of roots are characterized by fast growth, frequent branching, plagiotropism, and the ability to synthesize the same compounds as the roots of the intact plant. David et al., *Biotechnology* 2:73-76.(1984). Roots of Solanaceae plants are the main site of tropane alkaloid biosynthesis, and hence hairy root cultures also are capable of accumulating high levels of these metabolites. For example, see Oksman-Caldentey & Arroo, "Regulation of tropane alkaloid metabolism in plants and plant cell cultures," in METABOLIC ENGINEERING OF PLANT SECONDARY METABOLISM pp. 253-81 (Kluwer Academic Publishers, 2000).

Non-Nicotine Producing Cells for Genetic Engineering

The invention contemplates genetically engineering "non-nicotine producing cells" with a nucleic acid sequence encoding an enzyme involved in the production of nicotinic alkaloids. Non-nicotine producing cells refer to a cell from any organism that does not produce nicotine. Illustrative cells include but are not limited to plant cells, such as *Atropa belladonna, Arabidopsis* thalianu, as well as insect, mammalian, yeast, fungal, algal, or bacterial cells. Suitable host cells are discussed further in Goeddel, GENE EXPRESSION TECHNOLOGY: METHODS IN ENZYMOLOGY 185, Academic Press, San Diego, Calif. (1990).

"Insect cell" refers to any insect cell that can be transformed with a gene encoding a nicotine biosynthesis enzyme and is capable of expressing in recoverable amounts the enzyme or its products. Illustrative insect cells include Sf9 cells (ATCC CRL 171 1).

"Fungal cell" refers to any fungal cell that can be transformed with a gene encoding a nicotine biosynthesis enzyme and is capable of expressing in recoverable amounts the enzyme or its products. Illustrative fungal cells include yeast cells such as *Saccharomyces* cerivisae (Baldari, et al., 1987. EMBO J. 6:229-234) and *Pichia pastoris* (e.g. *P. pastoris* KM714 available from Invitrogen). Cells of filamentous fungi such as *Aspergillus* and *Trichodemza* may also be used. Archer, et al., *Antonie van Leeuwenhoek* 65:245-250 (2004).

"Bacterial cell" refers to any bacterial cell that can be transformed with a gene encoding a nicotinic alkaloid biosynthesis enzyme and is capable of expressing in recoverable amounts the enzyme or its products. Illustrative bacterial cells include *E. coli*, such as *E. coli* strain M15/rep4, which is available commercially from QIAGEN.

"Mammalian cell" refers to any mammalian cell that can be transformed with a gene encoding a nicotine bios synthesis enzyme and is capable of expressing in recoverable amounts the enzyme or its products. Illustrative mammalian cells include Chinese hamster ovary cells (CHO) or COS cells. Mammalian cells may also include a fertilized oocyte or an embryonic stem cell into which nicotinic alkaloid biosynthesis enzyme-coding sequences have been introduced. Such host cells can then be used to create non-human transgenic animals. Examples of systems for regulated expression of proteins in mammalian cells include Clontech's Tet-Off and Tet-On gene expression systems and similar systems. Gossen and Bujard, *Proc. Natl. Acad. Sci. USA* 89:55475551 (1992).

"Algae cell" refers to any algae species that can be transformed with a gene encoding a nicotine biosynthesis enzyme without adversely affecting normal algae development or physiology. Illustrative algae cells include *Chlamydomonas reinhardtii* (Mayfield and Franklin, *Vaccine* 23:1828-1 832 (2005).

Because production of nicotinic alkaloids in an insect cell could adversely affect insect growth and development, an inducible expression system may mitigate adverse affects. For example, insect cells may be first grown under non-inducing conditions to a desired state and then expression of the enzyme is induced.

Additionally, cells expressing nicotinic alkaloid biosynthesis genes may be supplied with precursors to increase substrate availability for nicotinic alkaloid synthesis. Cells may be supplied with analogs of precursors which may be incorporated into analogs of naturally occurring nicotinic alkaloids.

Transformation and Selection

While nicotine is the major alkaloid in *N. tabacum* and some other species in the *Nicotiana* genus, other plants have nicotine-producing ability, including, for example, *Duboisia, Solanum, Anthocercis* and *Salpiglessis* genera in the Solanaceae, and *Eclipta* and *Zinnia* genera in the Compositae. Using the inventive constructs and methods, nicotine may be produced in non-nicotine producing plants, such as *Atropa belladonna* and *Arabidopsis thaliana*, and cells, such as insect, fungal, and bacterial cells.

For the purposes of this description, a plant or non-nicotine producing cell, such as a fungal cell, may be transformed with a plasmid comprising one or more sequences, each operably linked to a promoter. For example, an illustrative vector may comprise a MPO1 sequence operably linked to a promoter. Likewise, the plasmid may comprise a MPO1 sequence operably linked to a promoter and an MPO2 sequence operably linked to a promoter. Alternatively, a plant or non-nicotine producing cell may be transformed with more than one plasmid. For example, a plant or non-nicotine producing cell may be transformed with a first plasmid comprising a QPT sequence operably linked to a promoter, which is distinct from a second plasmid comprising an MPO1 or MPO2 sequence. The first and second plasmids or portions thereof may be introduced into the same cell.

Plant Transformation

"Transgenic plant" refers to a plant that comprises a nucleic acid sequence that also is present per se in another organism or species or that is optimized, relative to host codon usage, from another organism or species. Both mono-cotyledonous and dicotyledonous angiosperm or gymno-sperm plant cells may be transformed in various ways known to the art. For example, see Klein et al., *Biotechnology* 4:583-590 (1993); Bechtold et al., *C. R. Acad. Sci. Paris* 3 16:1 194-1 199 (1993); Bent et al., *Mol. Gen. Genet.* 204:383-396 (1986); Paszowski et al., *EMBO J.* 3:2717-2722 (1984); Sagi et al., *Plant Cell Rep.* 13:262-266 (1994). *Agrobacterium* species such as *A. tumefaciens* and *A. rhizogenes* can be used, for example, in accordance with Nagel et al., *Microbial Lett* 67:325 (1990). Additionally, plants may be transformed by *Rhizobium, Sinorhizobium* or *Mesorhizobium* transformation. Broothaerts et al., *Nature* 433:629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation (Lorz et al., *Mol. Genet.* 199:179-182 (1985)), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

Transgenic plants without marker genes may be produced using a second plasmid comprising a nucleic acid encoding the marker, distinct from a first plasmid that comprises an MPO1 or MPO2 sequence. The first and second plasmids or portions thereof are introduced into the same plant cell, such that the selectable marker gene that is transiently expressed, transformed plant cells are identified, and transformed plants are obtained in which the MPO1 or MPO2 sequence is stably integrated into the genome and the selectable marker gene is not stably integrated. See U.S. published application No. 2003/0221213. The first plasmid that comprises a MPO1 or MPO2 sequence may optionally be a binary vector with a T-DNA region that is completely made up of nucleic acid sequences present in wild-type non-transgenic *N. tabacum* or sexually compatible *Nicotiana* species.

The *Agrobacterium* transformation methods discussed above are known to be useful for transforming dicots. Additionally, de la Pena et al., *Nature* 325:274-276 (1987), Rhodes et al., *Science* 240:204-207 (1988), and Shimamato et al., *Nature* 328:274-276 (1989) have transformed cereal monocots using *Agrobacterium*. Also see Bechtold et al., *C. R. Acad. Sci. Paris* 3 16 (1994), illustrating vacuum infiltration for *Agrobacterium*-mediated transformation.

Methods of regenerating a transgenic plant from a transformed cell or culture vary according to the plant species but are based on known methodology. For example, methods for regenerating of transgenic tobacco plants are well-known. Genetically engineered plants are selected that have increased expression of at least one of MPO1 and MPO2. Additionally, the inventive genetically engineered plants may have increased nicotine levels and yield. The inventive genetically engineered plants may optionally have genetically engineered increased expression of one or more of A622, NBB1, PMT, and QPT in addition to increased expression of at least one of MPO1 and MPO2.

Non-Nicotine Producing Cell Transformation

Constructs according to the invention may be used to transform any cell, using a suitable transformation technique, such as *Agrobacterium*-mediated transformation for plant cells, particle bombardment, electroporation, and polyethylene glycol fusion, calcium phosphate transfection, DEAE-dextran mediated transfection, or cationic lipid-mediated transfection.

Non-nicotine producing cells may be transformed with nucleic acid constructs of the present invention without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

For the purposes of the present description non-nicotine genetically engineered cells are selected that express at least one of MPO1 and MPO2 heterologously.

Quantifying Alkaloid Content

A. Reduced Alkaloids

Pursuant to one aspect of the invention, genetically engineered plants and cells are characterized by reduced alkaloid content.

A quantitative reduction in alkaloid levels can be assayed by several methods, as for example by quantification based on gas-liquid chromatography, high performance liquid chromatography, radio-immunoassays, and enzyme-linked immunosorbent assays. In the present invention, nicotinic alkaloid levels were measured by gas-liquid chromatography equipped with a capillary column and an FID detector, as described in Hibi et al., *Plant Physiology* 100:826-35 (1992).

In describing a plant of the invention, the phrase "reduced nicotine" or "reduced nicotinic alkaloid content" refers to a decrease in the amount of nicotinic alkaloid in the plant or cell when compared with a non-transformed control plant or cell. A reduced-nicotine plant encompasses a genetically engineered plant that contains less than half, preferably less than 25%, and more preferably less than 20% or less than 10% of the nicotine content of a control plant of the same variety. A reduced-nicotine plant also includes genetically engineered plants, such as *Nicotiana, Duboisia, Solanum, Anthocercis* and Salpiglessis genera in the Solanaceae or the *Eclipta* and *Zinnia* genera in the Compositae, that contain less total alkaloids compared with a control plant.

A reduced-alkaloid plant encompasses a genetically engineered plant that contains less than half, preferably less than 25%, and more preferably less than 20% or less than 10% of the "total alkaloid content" of a control plant of the same variety.

A reduced-anabasine plant encompasses a genetically engineered plant that contains less than half, preferably less than 25%, and more preferably less than 20% or less than 10% of the anabasine content of a control plant of the same variety.

A reduced-anatalline plant encompasses a genetically engineered plant that contains less than half, preferably less than 25%, and more preferably less than 20% or less than 10% of the anatalline content of a non-transgenic control plant of the same variety.

B. Increased Alkaloids

In one aspect of the invention, genetically engineered plants and cells are characterized by increased alkaloid content. Transformed nicotine producing cells are characterized by increased nicotinic alkaloid production.

In describing a plant of the invention, the phrase "increased alkaloid content" or "increased nicotinic alkaloid content" refers to an increase in the amount of alkaloid or nicotinic alkaloids in the plant or cell when compared with a non-transformed control plant or cell. "Increased nicotine plant" encompasses a genetically engineered plant that has an increase in nicotine content greater than 10%, and preferably greater than 50%, 100%, or 200% of the nicotine content of a control plant of the same species or variety. "Increased alkaloid plant" encompasses a genetically engineered plant that has an increase in alkaloid content greater than 10%, and preferably greater than 50%, 100%, or 200% of the alkaloid content of a control plant of the same species or variety. Plants of the Solonaceae and Erythroxylaceae are examples of plants that can be genetically engineered with MPO1 or MPO2 to increase alkaloids.

A quantitative increase in nicotinic alkaloid levels can be assayed by several methods, as for example by quantification based on gas-liquid chromatography, high performance liquid chromatography, radio-immunoassays, and enzyme-linked immunosorbent assays. In the present invention, nicotinic alkaloid levels were measured by gas-liquid chromatography equipped with a capillary column and an FID detector, as described in Hibi et al., *Plant Physiology* 100: 826-35 (1992).

Quantifying Yield

In one aspect, the genetically engineered plants and cells of the invention are characterized by increased nicotinic alkaloid content and yield. Increased nicotinic alkaloid production in the genetically engineered plants is preferably achieved by overexpressing one or more nicotine biosynthesis pathway genes, including at least one of MPO1 and MPO2.

In describing a plant of the invention, the phrase "increased yield" or "high yielding" refers to an increase in the amount of yield of a plant or crop of said plant when compared to an increased-nicotine control plant or crop of said plant. "Increased yield plant" encompasses a genetically engineered plant that yields the same as a non-increased nicotine plant, or yields a greater amount than an increased-nicotine plant, preferably greater than 110%, and more preferably greater than 125% of the yield of an increased-nicotine plant of the same species or variety.

A quantitative increase in photosynthetic efficiency can be assayed by several methods, as for example by quantifying photosynthetic rates, such as gas exchange and $CO_2$ fixation, and chlorophyll florescence. Miyagawa et al., *Plant Cell Physiol.* 41, 31 1-320 (2000). Photosynthetic rates may also be quantified by measuring metabolite and carbohydrate levels as described by Leegood, *Carbon Metabolism In Photosynthesis and production in a changing environment: a field and laboratory manual* (eds. Hall, Scurlock, Bolhar-Nordenkampf, Leegood, & Long) 247-267 (Chapman & Hall, London; 1993). Alternatively, photosynthetic activity may be calculated based on enzyme activity, such as Rubisco activity. Portis, A. R. *J. Exp. Bot.* 46:1285-1291 (1995).

Of course, increased yield can be determined by measuring more readily discernible characteristics, including but not limited to plant height, weight, leaf size, number of seeds produced, and seed weight.

Reduced-Nicotine Products

The present invention provides a transgenic plant or cell having reduced nicotinic-alkaloid levels. For example, the instant invention contemplates reducing nicotine levels by suppressing at least one of MPO1 and MPO2 expression. Following selection of a transgenic plant having suppression of at least MPO1 or MPO2 and reduced-nicotine content, a variety of products may be made from such a plant.

Because the present invention provides a method for reducing alkaloids, TSNAs may also be reduced because there is a significant, positive correlation between alkaloid content in tobacco and TSNA accumulation. For example, a significant correlation coefficient between anatabine and NAT was 0.76. Djordjevic et al., *J. Agric. Food Chem.*, 37:752-756 (1989). TSNAs are a class of carcinogens that are predominantly formed in tobacco during curing, processing, and smoking. Hoffman et al., *J. Natl. Cancer Inst.* 58, 1841-4 (1977); Wiernik et al., *Recent Adv. Tob. Sci*, 21:39-80 (1995). Nitrosamines, containing the organic functional group, N—N=O, are formed from the facile addition of an N=O group by a nitrosating agent to a nitrogen of a secondary or tertiary amine. This particular class of carcinogens is found only in tobacco although they could potentially occur in other nicotinic alkaloid-containing products.

TSNAs are considered to be among the most prominent carcinogens in cigarette smoke and their carcinogenic properties are well documented. See Hecht, *S. Mutat. Res.* 424:127-42 (1999); Hecht, *S. Toxicol.* 11,559-603 (1998); Hecht, S., et al., *Cancer Surv.* 8, 273-294 (1989). TSNAs have been cited as causes of oral cancer, esophageal cancer, pancreatic cancer, and lung cancer (Hecht & Hoffman, *IARC Sci. Publ.* (105) 54-61 (1991)). In particular, TSNAs have been implicated as the causative agent in the dramatic rise of adenocarcinorna associated with cigarette smoking and lung cancer (Hoffmann et al., *Crit. Rev. Toxicol.* 26, 199-21 1 (1996)).

The four TSNAs considered to be the most important by levels of exposure and carcinogenic potency and reported to be possibly carcinogenic to humans are N'-nitrosonornicotine (NNN), 4-methylnitrosoarnino-1-(3-pyridyl)-1-butanone (NNK), N'-nitrosoanatabine (NAT) and N'-nitrosoanabasine (NAB) Reviewed in IARC Monographs of the Evaluation of Carcinogenic Risk to Humans. Lyon (France) Vol 37, pp. 205-208 (1985). These TSNAs are formed by N-nitrosation of nicotine and of the minor *Nicotiana* alkaloids that include nornicotine, anatabine, and anabasine.

The following levels of alkaloid compounds have been reported for mainstream smoke of non-filter cigarettes (measured in yg/cigarette): nicotine: 100-3000, nornicotine: 5-150, anatabine: 5-15, Anabasine: 5-12 (Hoffmann et al., *Chem. Res. Toxicol.* 14:7:767-790 (2000)). Mainstream smoke of U.S. cigarettes, with or without filter tips, contain (measured in ng/cigarette): 9-180 ng NNK, 50-500 ng NNN, 3-25 ng NAB and 55-300 ng NAT. Hoffmann, et al., *J. Toxicol. Environ. Health* 41:1-52 (1994). It is important to note that the levels of these TSNAs in sidestream smoke are 5-10 fold above those in mainstream smoke. Hoffmann, et al (1994).

Xie et al. (Recent Advances in Tobacco Science 30:17-37 (2004)) reported that Vector 21-41, a genetically engineered reduced-nicotine tobacco with down-regulation of QPT, has a total alkaloid level of about 2300 ppm, which is less than 10 percent of the wild-type tobacco. See U.S. Pat. No. 6,907,887. Mainstream smoke from cigarettes made from the Vector 21-41 tobacco had less than 10 percent of NNN, NAT, NAB, and NNK compared to the levels of a standard full flavor cigarette produced from wild-type tobacco.

Strategies for reducing TSNAs by reducing the corresponding tobacco alkaloid precursors is currently a main focus of agricultural tobacco research. Sirninszky et al., *Proc. Natl. Acad. Sci. USA* 102(41) 14919-14924 (2005). To reduce formation of all TSNAs there is an urgent need to reduce the precursor nicotinic alkaloids as much as possible by genetic engineering.

A reduced-nicotine tobacco product may be in the form of leaf tobacco, shredded tobacco, cut tobacco and tobacco fractions. A reduced-nicotine tobacco product may include cigarette tobacco, cigar tobacco, snuff, chewing tobacco, pipe tobacco, and cigarettes made from genetically engineered reduced-nicotine tobacco for use in smoking cessation. Reduced-nicotine tobacco may also be used to produce reconstituted tobacco (Recon). Recon is produced from tobacco stems and/or smaller leaf particles by a process that closely resembles paper making. This process entails processing the various tobacco portions that are to be made into Recon and cutting the tobacco into a size and shape that resembles cut rag tobacco made from whole leaf tobacco. This cut recon then is mixed with cut-rag tobacco and is ready for cigarette making.

In addition to traditional tobacco products, such as cigarette and cigar tobacco, reduced-nicotine tobacco can be used as source for protein, fiber, ethanol, and animal feeds. See WO/2002/098208. For example, reduced-nicotine tobacco may be used as a source of Rubisco (ribulose bisphosphate carboxylase-oxygenase, or fraction 1 protein) because unlike other plants, tobacco-derived Rubisco can be readily extracted in crystalline form. With the exception of slightly lower levels of methionine, Rubisco's content of essential amino acids equals or exceeds that of the FAO Provisional Pattern. Ershoff, B. H., et al. *Society for Experimental Biology and Medicine* 157:626-630 (1978); Wildman, S. G. *Photosynthesis Research* 73:243-250 (2002).

For biofuels to replace a sizable portion of the world's dependence on nonrenewable energy sources, co-products, such as Rubisco, are required to help defray the cost of producing this renewable energy. Greene et al., *Growing Energy. How Biofuels Can End America's Oil Dependence; National Resources Defense Counsel* (2004). Thus, the greater reduction in nicotinic alkaloids in tobacco, the greater the likelihood of a successful tobacco biomass system.

Increased-Nicotine Products

The present invention provides a genetically engineered plant having increased-nicotine levels, as well as a genetically engineered non-nicotine producing cell that produces nicotine or related compounds, where said cell is derived from an organism that does not produce nicotine. A variety of products may be made from such a genetically engineered plant. Likewise, products can be made from cells that are genetically engineered for production of nicotine or related compounds.

Herbivore-Resistant Plant

Nicotine serves as a natural pesticide which helps protect tobacco plants from damage by pests. It has been show that conventionally bred or transgenic low-nicotine tobacco have increased susceptibility to insect damage. Legg, P. D., et al., *Can. J. Cyto.*, 13:287-291 (197 1); Voelckel, C., et al., *Chemoecology* 1 1:121-126 (2001); Steppuhn, A., et al., *PLoS Biol,* 2(8):e217:1074-1080 (2004). Using the inventive methods and constructs, increased-nicotine plants may be produced that have increased resistance to insect and other pest damage.

Increased-Nicotine Tobacco Products

The inventive constructs and methods may be used to produce, for example, cigarettes, cigars, and other traditional tobacco products such as snuff and snus. Additionally, increased-nicotine cigarettes may be produced that have reduced-exposure to smoke components, such as tar, yet have similar or increased nicotine deliveries as conventional cigarettes.

In the present description, an increased-nicotine tobacco product may be in the form of leaf tobacco, shredded tobacco, cut rag tobacco, ground tobacco, reconstituted tobacco, expanded or puffed tobacco and tobacco fractions including, for example, nicotine. An increased-nicotine tobacco product may include cigarettes, cigars, pipe tobaccos, and any form of smokeless tobacco such as snuff, snus, or chewing tobacco.

Blending different tobacco types or cultivars within a tobacco product such as a cigarette is common in tobacco art. It will therefore be appreciated that increased-nicotine tobacco could be blended at any percentage with non-transformed tobacco to obtain any level of desired nicotine content, up to the nicotine content of the increased nicotine tobacco utilized, to manufacture a tobacco product.

Increased nicotine cigarettes are particularly advantageous because studies demonstrate that when nicotine is increased, smokers inhale less tar and carbon monoxide. See Armitage et al., *Psychopharmacology* 96:447-453 (1988); Fagerström, *Psychopharmacology* 77:164-167 (1982); Russell, *Nicotine and Public Health* 15:265-284 (2000) and Woodman et al., *European Journal of Respiratory Disease* 70:3 16-321 (1987).

Cigarette smoke is an extremely complex mixture of more than 4,000 different compounds. Green & Rodgman, *Recent Advances in Tobacco Science* 22:131-304 (1996); TOM Report, page 9 of executive summary. Cigarette smoke is made up of two phases: a particulate phase, which is commonly called "tar" or total particulate matter, and a vapor phase, which contains gases and semi-volatile compounds. A common definition for "tar" is "nicotine-free dry smoke" or "nicotine-free dry particulate matter" (NFDPM) captured by a Cambridge pad when a cigarette is machine smoked. More specifically, "tar" is the total particulate matter isolated from smoke, excluding water and nicotine. Tar makes up less than ten percent of the weight of cigarette smoke. The tar component contains the majority of the most harmful smoke compounds.

Analytical methods combined with sensitive biological assays have led to the identification of 69 carcinogens in tobacco smoke. See THE CHANGING CIGARETTE: CHEMICAL STUDIES AND BIOASSAYS Chapter 5, Smoking and Tobacco Control Monograph No. 13 (NIH Pub. No. 02-5074, October 2001). It has become clear to researchers, however, that not all components of cigarette smoke have equal toxicity. Notably, the first U.S. Surgeon General's report on smoking in 1964 came to the conclusion that nicotine was probably not toxic at the levels inhaled by smokers, with the implication that the source of the primary pharmacologic reward to smokers was not of immediate concern. The Surgeon General's 1964 report stated, at page 74, that "[t]here is no acceptable evidence that prolonged exposure to nicotine creates either dangerous functional changes of an objective nature or degenerative diseases."

In fact, the U.S. Food and Drug Administration allows the sale of nicotine replacement products such as patches and chewing gum for use in smoking cessation therapy. These products may deliver more nicotine in one day than a pack of cigarettes. Page 167 of the IOM Report states, "Many studies of nicotine suggest that nicotine is unlikely to be a cancer-causing agent in humans or, at worst, that its carcinogenicity would be trivial compared to that of other components of tobacco. The consideration of nicotine as a carcinogenic agent, if at all, is trivial compared to the risk of other tobacco constituents."

Cigarettes are generally rated by the FTC (in the U.S.) or ISO smoking machine methods which determine, for example, the amount of tar and nicotine generated when a cigarette is smoked by a machine under standardized conditions. See Pillsbury et al., *J. Assoc. Off. Analytical Chem.* (1969); ISO:4387 (1991). Most commercial cigarettes generally yield about 10 to 15 parts "tar" to every 1 part nicotine, measured in milligrams, as analyzed in PCT application WO 2005/018307. Many public health officials believe that the current FTC/ISO machine smoking regime is flawed since these methodologies fail to take into account human smoking behavior which is primarily driven by nicotine seeking. In other words, these methods don't consider compensatory smoking. Compensatory smoking or compensation, as it is also called, essentially means over smoking (smoking more intensively) due to the reduced presence of nicotine in tobacco smoke or under smoking (smoking less intensively) due to the increased presence of nicotine. See Benowitz, N. *Compensatory Smoking of Low Yield Cigarettes, In Risks Associated with Smoking Cigarettes with Low Machine Measured Yields of Tar and Nicotine NCI Smoking and Tobacco Control Monograph* 13 (2001).

Novel smoking-machine methods are currently being evaluated, especially those that consider compensatory smoking of low-yield brands. An example is a method involving the adjustment of smoking parameters so that brands with lower ISO nicotine yields are machine smoked more intensely. Kozlowski and O'Connor *Lancet* 355:2159 (2000). Other proposed methods measure yields of toxins on a per nicotine unit basis or at a defined "target" nicotine yield. This is achieved, for example, by systematically varying puff volume, puff interval, and blockage of ventilation holes until the target nicotine yield is reached. Cigarettes can then be rated on the effort required to get the target nicotine yield as well as on toxin delivery at that yield. Consumers would benefit from these smoking-machine methods since comparisons of specific toxins among different brands could be evaluated.

Studies have suggested that many smokers Inhale just as much smoke with most "light" and "ultra-light" cigarettes as full flavor cigarettes (Gori and Lynch, *Regulatory Toxicology and Pharmacology* 5:3 14-326). Smokers may compensate or smoke lower-yield cigarettes (per the FTC or ISO method) more aggressively (than higher-yield cigarettes) in order to obtain their desired nicotine impact and mouth feel of smoke, which are important sensory properties. Rose, J. E. "The role of upper airway stimulation in smoking," in *Nicotine Replacement: A Critical Evaluation*, pp. 95-106, 1988.

The manner in which a smoker may compensate include the frequency of puffs per cigarette and volume of smoke inhalation of such puffs, duration of the smoke inhalation being held before exhaling, number of cigarettes smoked within a specified time period, and the percentage of each cigarette that is smoked (how far down the cigarette is smoked).

When the percentage of nicotine per unit of inhaled smoke volume increases, many smokers may compensate and inhale less smoke. Gori G. B., *Virtually Safe Cigarettes. Reviving an opportunity once tragically rejected*. IOS Press. Amsterdam, (2000). The higher the percentage of nicotine in cigarette tobacco, the higher the percentage of nicotine in cigarette smoke. More specifically, the higher the percentage of nicotine in a cigarette's filler, the higher the percentage of nicotine in cigarette smoke. "Filler" means any smokable material that is rolled within a cigarette or cigarette-like device and includes (a) all tobaccos, including but not limited to reconstituted and expanded tobaccos, (b) any non-tobacco substitutes that may accompany (a); (c) tobacco casings, (d) other additives including flavorings that (a), (b) or (c) are supplemented with. A cigarette-like device is any device specifically intended to deliver nicotine through an alternative "smoke" aerosol formed by heating tobacco materials. Characteristics of such devices are that they contain a high content of glycerin or a glycerin substitute with minimal or no combustion pyrolysis. Glycerin when heated, vaporizes rapidly and forms an aerosol that can be inhaled and is very similar in appearance and feel to conventional cigarette smoke.

Therefore, the nicotine content of tobacco filler contained within a cigarette or cigarette-like device, all other factors held constant (including but not limited to, the type of filter, cigarette paper including its porosity, plug wraps, and tipping paper utilized, and the amount of filter ventilation), would roughly have to double for a corresponding two-fold increase of nicotine in mainstream cigarette smoke. Further, the nicotine content of tobacco filler contained within a cigarette or cigarette-like device, all other factors held constant, would roughly have to triple for a corresponding three-fold increase of nicotine in mainstream cigarette smoke. The calculations in this section refer to protonated nicotine in the mainstream smoke of a cigarette augmented with the described increase in nicotine levels and not "free" or "volatile" nicotine.

In one preferred embodiment of the invention, a reduced-exposure cigarette is manufactured that comprises an increased-nicotine tobacco plant having up to a two-fold increase of nicotine. In another preferred embodiment of the present invention a reduced-exposure cigarette is manufactured comprising an increased-nicotine tobacco having greater than a two-fold increase of nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf "Flue-cured tobacco" refers to a method of drying tobacco plants in a ventilated barn with heat and is characterized by a unique color, high reducing sugar content, medium to heavy in body and exceptionally smooth smoking properties. Bacon et al., *Ind. Eng. Chem.* 44:292 (1952).

Increased-nicotine tobacco may contain higher nitrosamines since there is a positive correlation between alkaloid content in tobacco and TSNA accumulation. However, U.S. Pat. Nos. 5,803,081, 6,135,121, 6,805,134, 6,895,974 and 6,959,712 and U.S. Published Applications 2005/0034365, 2005/0072047, 2005/0223442, 2006/0041949, and PCT published application WO 2006/091194, and others, discuss methodology to reduce tobacco-specific nitrosamines, which can be applied to a tobacco product that utilizes the subject invention.

Accordingly, the present invention provides constructs and methodology for producing cigarettes and other tobacco products containing increased nicotine levels. A desirable reduced-exposure cigarette should deliver a smoker's desired level of nicotine per cigarette as efficiently as possible while maintaining acceptable taste. See WO 05/018307.

Reconstituted Tobacco, Expanded Tobacco and Blending

Increased-nicotine tobacco also may be used to produce reconstituted sheet tobacco (Recon) and expanded tobacco or puffed tobacco. Recon can be produced from the following: tobacco dust, stems, small leaf particles, other byproducts of tobacco processing and cigarette manufacturing, and sometimes straight whole leaf. The recon process, which varies by manufacturer, closely resembles the typical paper making process and entails processing the various tobacco fractions and then cutting the recon sheets into a size and shape that resembles cigarette tobacco (cut-rag tobacco).

In addition, increased-nicotine tobacco may be used, according to the present invention, to produce expanded tobacco, also known as puffed tobacco, which is an important component in many cigarette brands. Expanded tobacco is made through expansion of suitable gases, whereby the tobacco is "puffed," resulting in reduced density and greater filling capacity, which in turn reduces the weight of tobacco used in cigarettes. By using increased-nicotine tobacco as a starting material, cigarettes made with the resultant expanded tobacco will yield reduced ratios of toxic chemicals, such as tar and carbon monoxide, to nicotine.

Increased-nicotine expanded tobacco, increased-nicotine Recon, and increased-nicotine cut-rag tobacco can be blended at any percentage among the three or with any percentages of non-transformed expanded tobacco, non-transformed recon or non-transformed cut-rag to produce cigarette filler containing varying nicotine contents. Any such blend is then incorporated into the cigarette making process according to standard methods known in the art.

Tobacco products other than cigarettes utilizing genetically engineered increased-nicotine tobacco are manufactured using any of the tobacco plant material described herein according to standard methods known in the art. In one embodiment, tobacco products are manufactured comprising plant material obtained from increased-nicotine tobacco. The increased-nicotine content can be up to greater than three times that of wild type cultivars.

Nicotinic Alkaloid Enzymes and Analogs

In addition to traditional tobacco products, such as cigarettes and chewing tobacco, the present invention provides methodology for producing nicotine and nicotine analogs, as well as enzymes for synthesis of nicotine and nicotine analogs. These compounds may be produced by genetically engineered nicotine-producing plants and non-nicotine producing cells, as well as in a cell-free/in vitro system.

Because recent studies suggest a role for nicotine receptors in treating a variety of conditions and disorders, such as Alzheimer's disease, schizophrenia, central and autonomic nervous systems dysfunction, and addictions, there is a need for nicotine receptor ligand sources. For example, the inventive methods and constructs may be used for producing nicotinic alkaloids. It has been shown that transgenic hairy root cultures overexpressing PMT provide an effective means for large-scale commercial production of scopolamine, a pharmaceutically important tropane alkaloid. Zhang et al, *Proc. Nat'l Acad. Sci. USA* 101:6786-91 (2004). Accordingly, large-scale or commercial quantities of nicotinic alkaloids can be produced in tobacco hairy root culture by overexpressing at least one of MPO1 and MPO2. Likewise, the present invention contemplates cell culture systems, such as bacterial or insect cell cultures, for producing large-scale or commercial quantities of nicotinic alkaloids, nicotine analogs or nicotine precursors by expressing at least one of MPO1 and MPO2. The cells may optionally express other nicotine biosynthesis genes such as PMT, QPT, A622 and NBB1.

Additionally, products can be made directly using the activity of MPO enzymes encoded by MPO1 and MPO2. For example, recombinant MPO1 and MPO2 enzymes may be used for the synthesis, or partial synthesis, of nicotinic alkaloids or nicotinic alkaloid analogs. Accordingly, large-scale or commercial quantities of MPO1 and MPO2 can be produced by a variety of methods using the MPO1 and MPO2 genes, including extracting recombinant enzyme from a genetically engineered plant, cell, or culture system, including but not limited to hairy root cultures, insect, bacterial, fungal, plant, algae, and mammalian cell culture, or in vitro.

Specific examples are presented below of methods for identifying sequences encoding MPO enzymes involved in alkaloid biosynthesis, as well as for introducing target gene to produce plant transformants with altered alkaloid contents. They are meant to be exemplary and not as limitations on the present invention.

Example 1: Identification of MPO1 and MPO2 as Genes Regulated by the Nic Loci

A cDNA micro-array prepared from a *Nicotiana sylvestris*-derived cDNA library, see Katoh et al., *Proc. Japan Acad.*, Vol. 79, Ser. B, No. 6, pp. 151-154 (2003), was used to search for novel genes which are controlled by the nicotine biosynthesis regulatory NIC loci.

*N. sylvestris* cDNAs were amplified by PCR and spotted onto mirror-coated slides (type 7 star, Amersham) using an Amersham Lucidea array spotter. DNA was immobilized on the slide surface by UV crosslinking (120 mJ/m2). *N. tabacum* Burley 21 plantlets (WT and nic1nic2) were grown on half-strength B5 medium supplemented with 1.5% (W/V) sucrose and 0.35% (W/V) gellan gum (Wako) in Agripot containers (Kirin).

Roots of eight-week-old plantlets were harvested, immediately frozen with liquid nitrogen, and kept at −80° C. until use. Total RNA was isolated from the frozen roots using a Plant RNeasy Mini kit (Qiagen), and mRNA was purified using a GenElute mRNA Miniprep kit (Sigma). cDNA was synthesized from 0.4 pg of the purified mRNA using a Labelstar Array Kit (Qiagen) and Cy3 or Cy5-dCTP (Amersham). cDNA hybridization to the microarray slides and post-hybridization washes were performed using a *Lucida Pro* hybrid-machine (Amersham). Microarrays were scanned using an FLA-8000 scanner (Fujifilm). Acquired array images were quantified for signal intensity with ArrayGauge software (Fujifilm). cDNA probes from wild type and nic1nic2 tobacco were labeled with Cy3 and Cy5 in reciprocal pair-wise combinations. Hybridization signals were normalized to the total signal intensity of dyes. cDNA clones which hybridized to wild-type probes more than twice as strongly as they did to nic1nic2 probes were identified, and these included MPO1. Full-length MPO1 cDNA was obtained by 5'- and 3'-RACE from total RNA of *N. tabacum* by using a SMART RACE cDNA Amplification Kit (Clontech). During this cloning precudure, another cDNA clone of *N. tabacum* that was highly homologous to the MPO1 nucleotide sequence was found, and its full-length cDNA, obtained by 5'- and 3'-RACE as described above, was designated as MPO2.

The nucleotide sequences of the MPO1 and MPO2 cDNA inserts were determined on both strands using an ABI PRISM® 3100 Genetic Analyzer (Applied Biosystems) and a BigDye® Terminator v3.1 Cycle Sequencing Kit (Applied Biosystems). The nucleotide sequences of the MPO1 and the MPO2 are set forth in SEQ ID NO: 1 and SEQ ID NO: 3, respectively. The respective amino acid sequences encoded by the nucleotide sequences are set forth in SEQ ID NO: 2 and SEQ ID NO: 4. The protein sequences include a putative active-site tyrosine and three histidines presumably required for binding copper. The nucleotide sequences of the MPO1 ORF and the MPO2 ORF are set forth in SEQ ID NO: 5 and SEQ ID NO: 6, respectively.

Example 2: Enzymology of MPO1

The open reading frame of the MPO1 nucleotide sequence (SEQ ID NO: 1) was amplified by PCR using the following primers:

```
primer 1:
                                            (SEQ ID NO: 7)
5'-CGATATCAATGGCCACTACTAAACAGAAAGTGACGGCACC-3'
```

-continued

```
primer 2:
                                        (SEQ ID NO: 8)
5'-TCGCCGGCGTCAAAGCTTGGCCAGCAA-3'
```

The PCR product was first cloned into a pGEM-T Easy vector (Promega), then excised as the EcoRV-Not1 fragment, and finally cloned into the expression vector pGEX-6P (GE Healthcare). The resultant plasmid pGEX-MPO1 was introduced into the *E. coli* strain Rosetta (DE3) (Novagen). The recombinant bacteria were cultured in LB medium containing 50 µg/ml carbenicillin at 37° C. until the $OD_{600}$ of the culture reached 0.4, IPTG and CuSO4 were added to the culture to the final concentrations of 0.1 mM and 4 mM, respectively, and the cultures were incubated at 16° C. for 16 h. Bacteria were harvested by centrifugation, suspended in a PBS buffer containing 10 mM DTT and 1 mg/ml lysozyme, incubated at 4° C. for 2 h, and then sonicated for 3 min. After centrifugation of the homogenate, the recombinant MPO1 protein fused to GST was purified from the supernatant by GSTrap HP (GE Healthcare) according to the manufacturer's protocol.

To measure the amine oxidase activity, ammonia produced was measured enzymatically using glutamate dehydrogenase (from beef liver; Oriental Yeast Co., Tokyo) by monitoring the decrease in NADH at 339 nm (Kusche and Lorenz, Methods of Enzymatic Analysis, Vol. 3, pp. 237-250 (1983)). Purified diamine oxidase from pig kidney was purchased from Sigma. Enzyme activities were calculated by data analysis software, Kaleida Graph (HULINKS). Table 1 shows that recombinant tobacco MPO1 preferentially oxidatively deaminated N-methlated diamines, with the lowest $K_m$ value of 0.036 mM observed for N-methylputrescine. On the other hand, pig kidney diamine oxidase preferred putrescine over N-methylputrescine. This demonstrates that MPO1 is a diamine oxidase with a high preference for N-methylputrescine as substrate.

To determine the subunit organization of MPO1 protein, the GST purification tag in the fusion protein was removed by treatment with PreScission protease (GE Healthcare). The molecular weight of the native MPO1 protein was determined by chromatography using a calibrated TSK-GEL gel filtration column (TOSOH, Tokyo) and PBS buffer. The subunit size was determined by measuring the molecular weight of the denatured MPO1 protein by SDSPAGE. The native molecular weight of MPO1 was estimated to be 172+/−10 kDa, whereas its denatured molecular weight was 84+/−11 kDa, which is in reasonable agreement with a molecular weight of 89 kDa calculated from the predicted amino acid sequence. This experiment indicates that MPO1 is a dimer, as are known diamine oxidases.

Example 3: Expression Profile of MPO

MPO expression was investigated in tobacco plants by Northern blot analysis. RNA was extracted from plant bodies which had been treated with methyljasmonate vapor, using *Nicotiana tabacum* cv. Burley 21 (abbreviated below as WT) and lines in which nic1, nic2 and nic1 nic2 mutations had been introduced into the Burley 21 background. Plants were raised in a sterile sealed environment for 2 months at 25° C. with 150 µmole photons/m2 of light (16 h light, 8 h dark) on ½×B5 medium (with 3% sucrose and 0.3% gellan gum). Methyl jasmonate treatment was accomplished by adding 0.5 mL of 100 µM methyl jasmonate to an Agripot container (Kirin, Tokyo) with a solid medium volume of 80 $cm^3$ and a gas volume of 250 $cm^3$ containing the plants. The root parts and leaf parts (2nd through 6th leaves from a plant with a total of 7 to 10 leaves) were collected from treated and control plants 24 h after the addition of methyl jasmonate and immediately stored frozen using liquid nitrogen.

RNA was extracted using an RNeasy Midi Kit (Qiagen) according to the manufacturer's protocol, except that polyvinyl pyrrolidone was added to a concentration of 1% to the extraction buffer. The column operation was performed twice to increase the purity of the RNA.

RNA blotting was carried out according to the ordinary methods given by Sambrook, J. et al., *Molecular Cloning*, Cold Spring Harbor Laboratory, Chapter 7 (2001).

The sequence fragment from the start (1 bp) to 413 bp of the MPO1 nucleotide sequence (SEQ ID NO: 1) was used as the probe template. The template was prepared by amplification from the cDNA clone using PCR using the following primers:

```
primer 1:
                                        (SEQ ID NO: 9)
5'-GGGTTCTCATCRCAGCTTTC primer 2:
                                        (SEQ ID NO: 10)
5'-CCATCTCTGACCTCAGGTGTT
```

The probe was labeled with $^{32}P$ using a Bcabest labeling kit (Takara) according to the manufacturer's instructions. Hybridization was accomplished using ULTRAhyb (Ambion) as the buffer according to the manufacturer's protocol. Because MPO1 and MPO2 have very similar nucleotide sequences, the MPO1 probe used probably detected transcripts of both MPO1 and MPO2. When a probe was prepared from MPO2 the hybridization patterns were similar to those obtained with the MPO1 probe (results not shown).

PMT probe was prepared from a PMT sequence cloned into a pcDNAII vector in *E. coli* (Hibi et al, 1994). The plasmid was extracted and purified from the *E. coli* using a QIAprep Spin Miniprep Kit (Qiagen), treated with the restriction enzymes XbaI and Hind111 by ordinary methods, and run through agarose gel electrophoresis, and DNA fragments having a size of about 1.5 kb were collected. A QIAquick Gel Extraction Kit (Qiagen) was used for collection. The collected DNA fragments were labeled with $^{32}P$ by the same methods used for the MPO1 probe, and hybridized.

Figure 2:
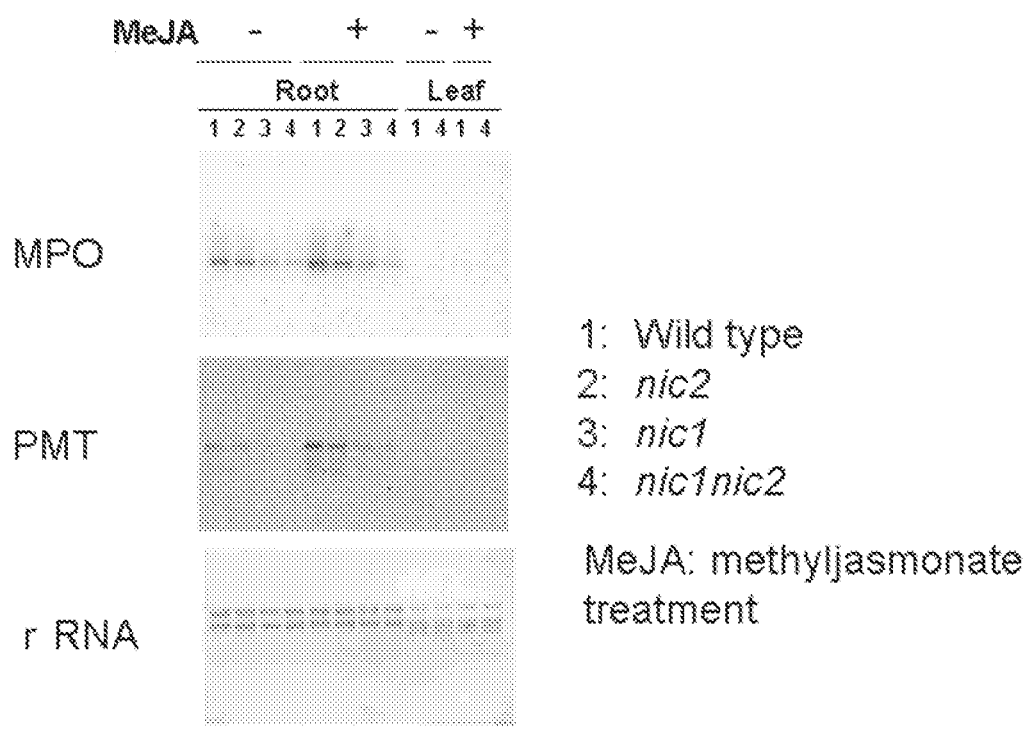
FIG. 2: Depicts an RNA gel blot analysis of expression of MPO and PMT in tobacco lines with different alleles at the NIC loci and in response to methyljasmonate treatment.
Figure 3:
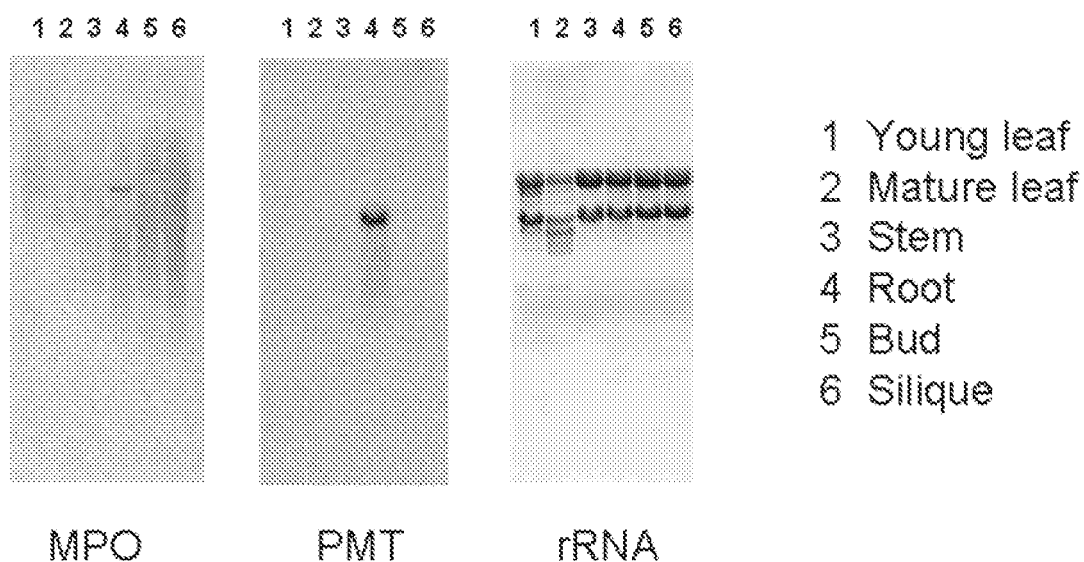
FIG. 3: Depicts an RNA gel blot analysis of expression of MPO and PMT in different tissues of tobacco plants. rRNA indicates RNA blots probed with a ribosomal RNA control sequence.

As FIGS. 2 and 3 clearly show, MPO and PMT have the same pattern of expression in tobacco plants. Both genes are regulated positively by the NIC loci and methyljasmonate, and are expressed exclusively in the roots of tobacco plants.

Relative Expression Levels of MPO1 and MPO2

Figure 4:
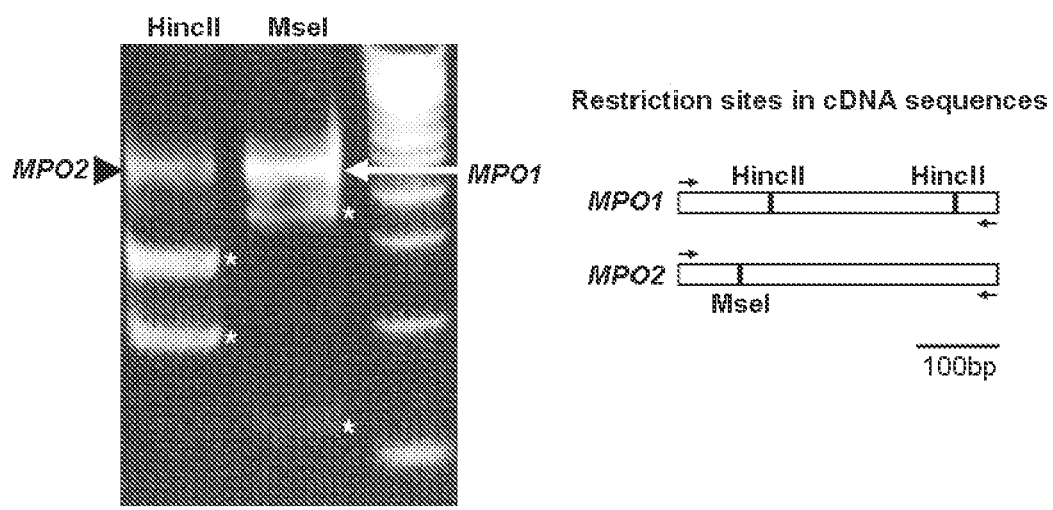
FIG. 4: Relative expression levels of MPO1 and MPO2 in tobacco hairy roots.

The tobacco genome contains two homologous MPO genes, MPO1 and MPO2. MPO1 contains an NsiI restriction site that is not present in in MPO2, and MPO2 contains a BamHI site that is not present in MPO1. We estimated the relative levels of each transcript by semi-quantitative RT-PCR followed by specific cleavage. Using an RNeasy Kit, total RNA was isolated from tobacco hairy roots, and first-strand cDNAs were synthesized with SuperScriptII reverse transcriptase. A pair of primers designed to anneal with sequences identical in MPO1 and MPO2 was used to amplify the intervening sequences from both cDNAs as a mixture. The PCR cycle number was adjusted to avoid saturated amplification. The PCR products containing both MPO sequences were treated with BamHI and NsiI to digest MPO2 and MPO1, respectively. The reaction products were separated on an agarose gel and stained with EtBr. Undigested MPO1 and MPO2 fragments were detected along with smaller digestion products. From comparing the intensities of the undigested products bands in FIG. 4 it is evident that expression of MPO1 was much higher than expression of MPO2 in tobacco hairy roots.

Example 4: Phylogenetic Analysis of MPO1 and MPO2

The amino acid sequences of MPO1 and MPO2 show 88% identity and 96% homology. MPO1 has 25% identity and 43% homology to the *Pisum sativum* amine oxidase (PSAO; Tipping AJ and McPherson M J, *J Biol. Chem. Vol.* 270, 16939-16946 (1995)) and 27% identity and 43% homology to the *Arabidopsis thaliana* amine oxidase (ATAO1, At4g14940; Moller SG and McPherson M J, *Plant J.* Vol. 13, 781-791 (1998)). A phylogenetic tree was constructed using the sequences of MPO1, MPO2, PSAO, ATAO1, and diamine oxidase-like proteins of *Arabidopsis thaliana*. The phylogenetic analysis was performed using neighbor joining method with the CLUSTAL W program. Branch lengths reflect sequence diversity counted as the number of substitutions per residue. The *Arabidopsis* sequences used were: At1g31710, At1g31690, At1g31670, At1g31680, At4g12280, At4g1229990, At4g14940 (ATAO1), At4g12270, At1g62810, At3g43670, and At2g42490.

Figure 5:
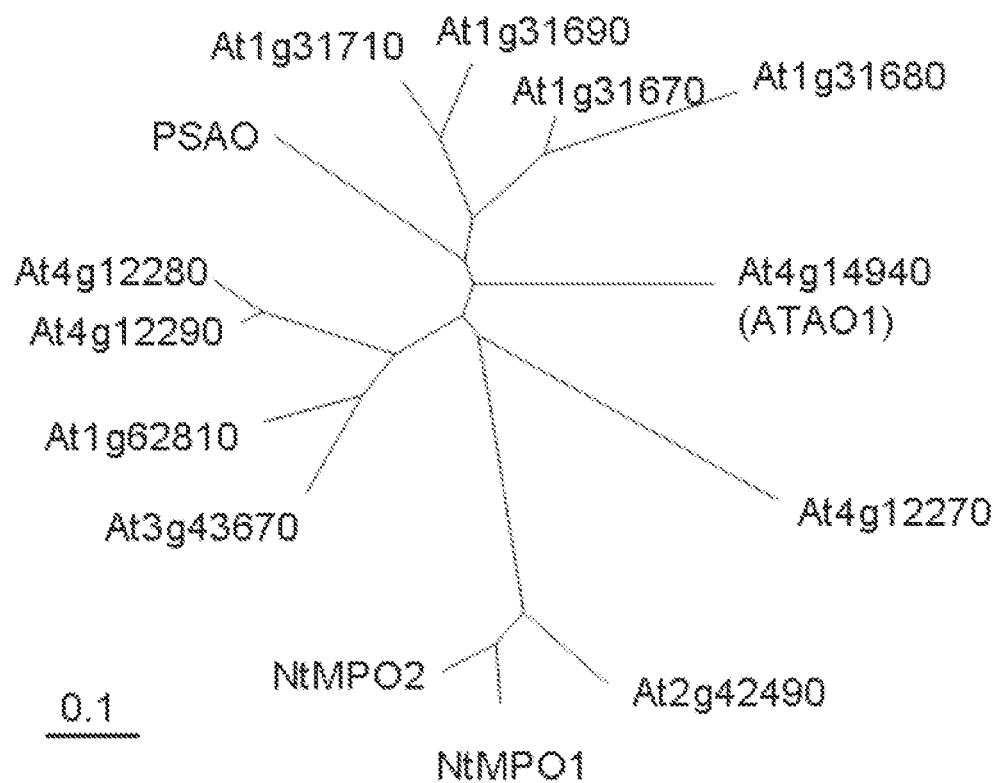
FIG. 5: Depicts a phylogenetic tree constructed using full length cDNA sequences of tobacco N-methylputrescine oxidases, plant diamine oxidases, and Arabidopsis homologues.

The results are shown in FIG. 5. MPO1, MPO2, and an uncharacterized *Arabidopsis* protein At2g42490 form a distinct clade, and are separated from the other sequences, including PSAO and ATAO1, at the base of the tree. PSAO and ATAO1 both contain predicted signal peptides at their N-termini, and are thought to be extracellular copper amine oxidases, whereas MPO1, MPO2, and At2g42490 lack predicted signal peptides.

Example 5: MPO Suppression in Transgenic Hairy Roots

RNAi was used to down-regulate the MPO genes in tobacco hairy roots. A portion of the MPO1 cDNA (about 400 bp in length), which is a highly homologous between MPO1 and MPO2, was amplified by PCR using the following primers:

```
Primer 1:
                                   (SEQ ID NO: 11)
5' GTTAGACGCTCGAGGCGACTAACAGTG 3'

Primer 2:
                                   (SEQ ID NO: 12)
5' GCATATTGTGAATTCCATAGATTGTGC 3'

Primer 3:
                                   (SEQ ID NO: 13)
5' GTTAGACGGTCTAGACGACTAACAGTG 3'

Primer 4:
                                   (SEQ ID NO: 14)
5' GCATATTGTGTAAGCTTTAGATTGTGC 3'
```

The fragment was subcloned into the pHANNIBAL vector such that two identical cDNA segments were placed in an inverted orientation on both sides of a pdk intron linker to produce a transcriptional cassette that expresses an mRNA capable of forming a dsRNA region comprising a segment of the MPO1 sequence. This unit was excised and inserted into the binary vector pBI121 to obtain pBI-MPO-Ri. (see FIG. 6A)

The pBI-MPO-Ri vector was introduced into *Agrobacterium rhizogenes* strain 15834, which was used to transform tobacco SR-1 using a leaf disc method. Kanega et al. (1994) *Plant Physiol* 105:483-490. After selection on kanamycin-containing medium, transgenic hairy roots were maintained by subculturing in liquid MS medium every two weeks. Hairy roots that were growing well were used for further analyses.

To confirm the suppression of the MPO genes, we carried out RT-PCR analysis of expression. Root tissue was frozen in liquid nitrogen and total RNA was isolated using an RNeasy Kit (Qiagen). First-strand cDNAs were reverse-transcribed using SuperScriptII (Invitrogen). PCR amplifications were done with following sets of primers:

```
for both MPO1 and MPO2:
                                   (SEQ ID NO: 15)
5'-CCTTTGGACCCTTTATCTGCTGC-3'
and
                                   (SEQ ID NO: 16)
5'-GGTCTTGCATATCCATTTTCCATTGG-3' for MPO1 alone:
                                   (SEQ ID NO: 17)
5'-CAGCTTTCTTCCTAGCTAAGC-3'
and
                                   (SEQ ID NO: 18)
5'-CTCTCTGTCCTGAATACAAGTGG-3' for MPO2 alone:
                                   (SEQ ID NO: 19)
5'-TGGAAGTTTGCCTGTTGTGTGTC-3'
and
                                   (SEQ ID NO: 20)
5'-AAGCTGGTACCTGGTCCAAACTG-3'
```

Figure 7A:
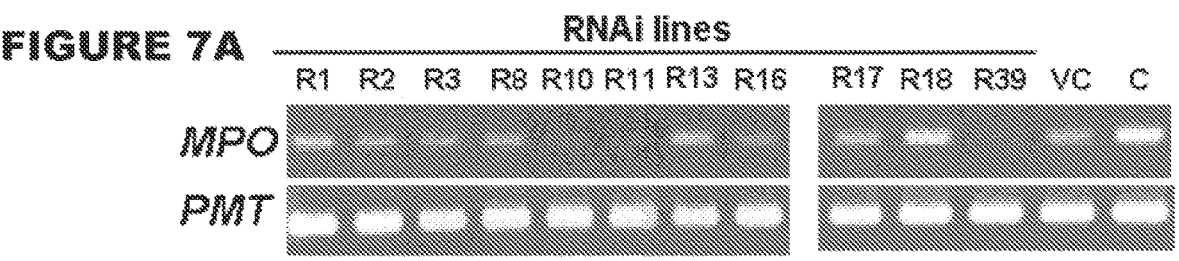
FIG. 7A: MPO and PMT mRNA levels in tobacco hairy roots lines.
Figure 7B:
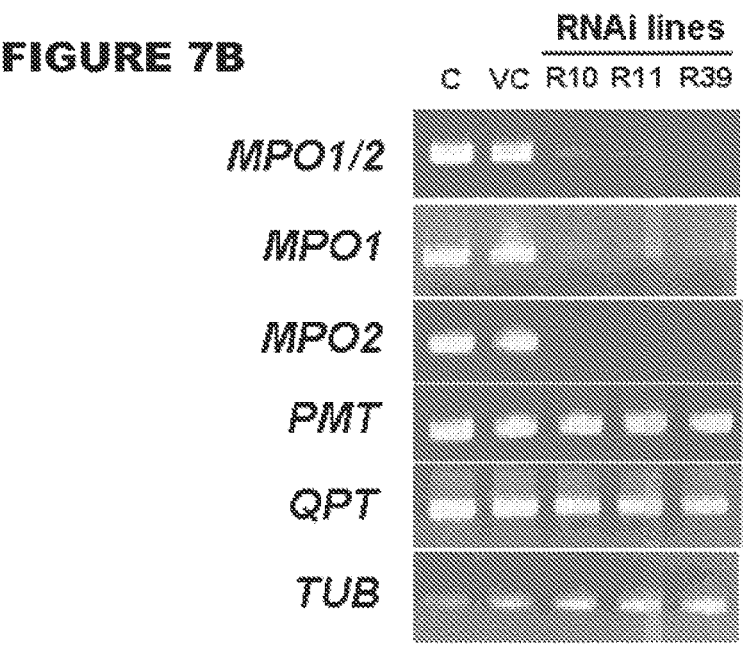
FIG. 7B: MPO1, MPO2, PMT and QPT mRNA levels in MPO down-regulated tobacco hairy roots.
Figure 8:
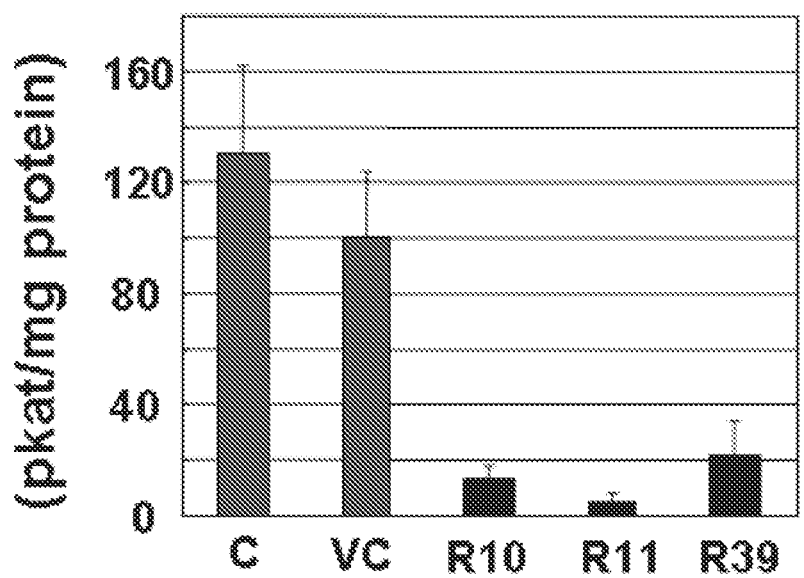
FIG. 8: MPO activity in MPO down-regulated tobacco hairy root lines.

In three lines (R10, R11, and R39) out of 11 independent hairy root lines examined, the transcript levels of MPO genes were significantly decreased. See FIG. 7A. In these lines the transcript levels of both MPO1 and MPO2 were decreased, but the levels of other nicotine biosynthetic genes (PMT and QPT). See FIG. 7B. Consistent with the reduced MPO RNA level, the MPO enzyme activities were significantly lower in these lines than in the control lines. See FIG. 8.

Figure 9:
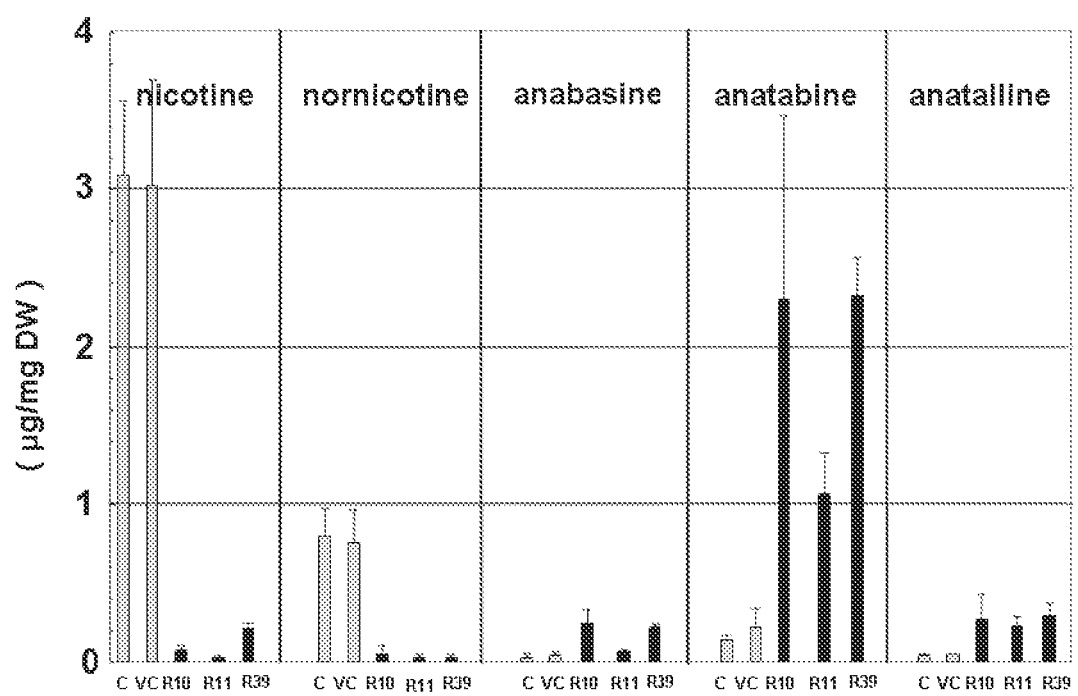
FIG. 9: Alkaloid levels in MPO down-regulated tobacco hairy root lines.

We analyzed the alkaloid contents in the MPO down-regulated lines. Alkaloids were extracted from hairy roots 7 days after subculture and quantified by GLC as described in the previous section. In all three lines, nicotine and nornicotine were markedly decreased, while other alkaloids (anatabine, anabasine, and anatalline) were increased. See FIG. 9. Anatabine was the major alkaloid accumulating in the hairy roots in which MPO was suppressed. These results indicate that reduced MPO expression restricts the pyrrolidine branch of tobacco alkaloid biosynthesis, and leads to elevated levels of alkaloids that do not possess the pyrrolidine moiety, such as anatabine, anabasine, and anatalline.

The effects of MPO suppression on the content of its substrate, N-methylputrescine, and precursors and related compounds, including the polyamines putrescine, spermidine, and spermine, were examined. Extraction and quantification of polyamines were carried out as described in Hibi et al. (1992). In brief, free and conjugated forms of these compounds were separately extracted using perchloric acid and heat treatments, and then subjected to HPLC analysis after dansylation for fluormetric detection. Free and conjugated forms of putrescine and N-methylputrescine increased in the MPO-suppressed lines R11 and R39. In contrast, spermidine and spermine were not markedly affected, except that conjugated spermine in a perichloric acid-insoluble fraction was elevated relative to the control. Overall, MPO suppression resulted in increased accumulation of N-methylputrescine and some polyamines.

Example 6: MPO Suppression in Transgenic Tobacco Plants

Production of Transgenic Tobacco Plants

The MPO1 RNAi suppression vector pBI-MPO-Ri was transformed into *Agrobacterium tumefaciens* strain EH.4105, which was used to transform leaf segments of tobacco variety K326. Transgenic TO shoots were regenerated.

To produce transgenic plants, transgenic shoots are transferred to rooting medium. Several rooted transgenic plants are transferred to soil. Transgenic plants are grown at 27° C. under continuous light in a growth chamber.

Expression of MPO

MPO expression in transgenic plants is analyzed by Northern blot analysis. The root parts of transgenic and control plants are collected and immediately stored frozen using liquid nitrogen. RNA is extracted from the frozen roots using an RNeasy Midi Kit (Qiagen) according to the manufacturer's protocol, except that polyvinyl pyrrolidone is added to a concentration of 1% to the extraction buffer. The column operation is performed twice to increase the purity of the RNA. RNA blotting is carried out according to the ordinary methods given by Sambrook, J. et al., MOLECULAR CLONING, Cold Spring Harbor Laboratory, Chapter 7 (2001). The fragment corresponding to the MPO1 nucleotide sequence in the MPO1 RNAi suppression cassette in pBI-MPO-Ri is used as the probe template. The template is prepared by amplification from the cDNA clone using PCR primers. The probe is labeled with $^{32}$P using a Bcabest labeling kit (Takara) according to the manufacturer's instructions. Hybridization are accomplished using ULTRAhyb (Ambion) as the buffer according to the manufacturer's protocol. Transgenic plants having reduced levels of MPO mRNA compared to the control are selected.

Procedure for Analysis of Alkaloid Levels

The nicotine content in leaves of plants is sampled 36 days after transfer to soil. Alkaloids are extracted from the transgenic tobacco leaves and analyzed, as described above. Lines that show reduced nicotine accumulation compared to control (non-transformed lines) are selected.

Example 7: Overexpression of MPO1 in Tobacco BY-2 Cells

To examine whether MPO overexpression changes the alkaloid profile, a binary vector containing MPO1 cDNA under the control of the CaMV 35S promoter was constructed and introduced by *Agrobacterium*-mediated transformation into tobacco BY-2 cells. A full-length MPO1 ORF was amplified by PCR with primers attached with appropriate restriction sites with high fidelity KOD-plus DNA polymerase (Toyobo) and subcloned into multi-cloning sites of pBluescriptII. After sequencing for confirmation, the ORF was excised and inserted into pBI121 to produce pBI-MPO (see FIG. 6B) *Agrobacterium tumefaciens* strain EHA105 with the vector was used to transform tobacco BY-2 cells and transgenic cells were selected by kanamycin resistance. Independent transgenic cell lines were subcultured each week in liquid MS medium supplemented with the synthetic auxin 2,4-D. Because tobacco BY-2 cells do not produce tobacco alkaloids under normal culture conditions, four-day-old tobacco cell cultures were rinsed to remove 2,4-D, and were transferred to fresh auxin-free MS medium containing 100 μM methyljasmonate, and cultured for an additional 1 day for the RNA and protein analyses, or for 3 days for alkaloid measurements.

Overexpression of MPO1

For RNA gel blotting, total RNA was isolated from methyljasmonate-treated cells with a RNeasy Kit, separated by electrophoresis on a 1.2% formaldehyde agarose gel, and transferred onto a Hybond-N+ nylon membrane (Amersham Pharmatia Biotech). Equal loading of RNA was confirmed by ethidium bromide staining. The blots were hybridized with a MPO1 cDNA fragment that was labeled with $^{32}$P by using a Bcabest labeling kit (Takara). Three independent lines (OX4, OX6, and OX14) showed highly increased mRNA accumulation, in contrast to the control cells that showed no detectable MPO mRNA. See FIG. 10A.

The transgenic cell lines OX4, OX6, and OX14 also showed enzymatic activity of MPO, in contrast to the control cells that showed no detectable MPO activity. See FIG. 10B.

Alkaloid Profiles

Figure 11:
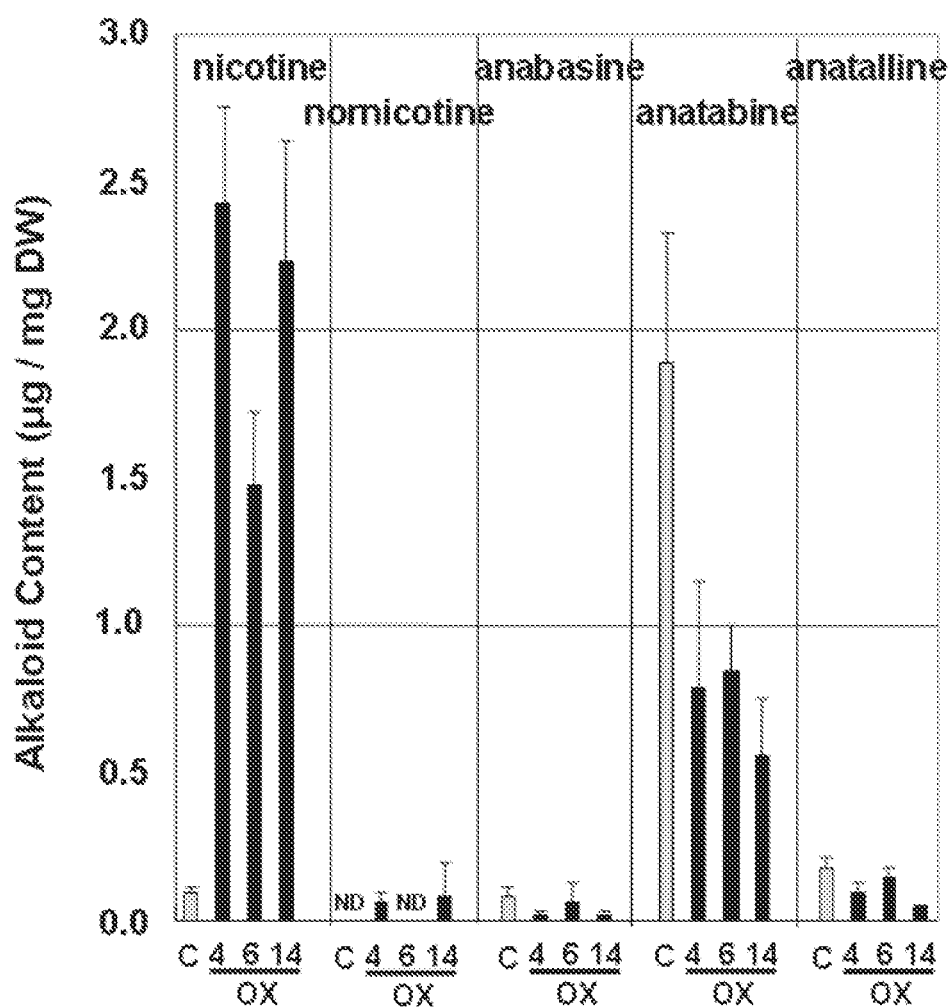
FIG. 11: Alkaloid levels in BY-2 cells transformed with pBI-MPO.

Alkaloid contents in tobacco BY-2 cells after methyljasmonate treatment were analyzed. Anatabine was the major alkaloid observed in the control BY-2 cells, reflecting the very low expression of MPO1. On the contrary, MPO1-overexpressing cell lines accumulated highly elevated levels of nicotine and reduced levels of anatabine. See FIG. 11. This suggests that increased expression of MPO1 facilitated formation of methylpyrrolinium cation, resulting a large shift in the nicotine-to-anatabine ratio in favor of nicotine accumulation.

Example 8: Overexpression of MPO1 in Tobacco Plants

Description of pBI-QPT-MPO1 Overexpression Vector

The MPO1 cDNA sequence was inserted between the pTobRD2 promoter and the nos terminator to produce an MPO1 expression cassette in which expression is controlled by the root-cortex specific promoter. The MPO1 expression cassette was cloned within the T-DNA borders of an *Agrobacterium* binary vector plasmid that contains an nptII selectable marker cassette within the T-DNA region to produce an MPO1 overexpression vector pBI-QPT-MPO1 with the T-DNA region comprising the nptII casssette and the TobRD2-MPO1 expression cassette. See FIG. 6C. pBI-QPT-MPO1 is similar to pBI-MPO1, except that the MOP cDNA is expressed from the tobacco root cortex specific promoter rather than the CaMV 35S promoter.

Production of Transgenic Tobacco Plants

The MPO1 overexpression vectors pBI-QPT-MPO1 and pBI-MPO1 were transformed separately into *Agrobacterium tumefaciens* strain EHA105, which was used to transform leaf segments of tobacco cultivar K326. Transgenic TO shoots were regenerated on selection medium, and transferred to rooting medium.

Several rooted transgenic plants from independent transgenic lines are transferred to soil to produce material for further analysis.

Expression of MPO

MPO expression in transgenic plants is analyzed by Northern blot analysis. The root parts of transgenic and control plants are collected and immediately stored frozen using liquid nitrogen. RNA is extracted from the frozen roots using an RNeasy Midi Kit (Qiagen) according to the manufacturer's protocol, except that polyvinyl pyrrolidone is added to a concentration of 1% to the extraction buffer. The column operation is performed twice to increase the purity of the RNA. RNA blotting is carried out according to the ordinary methods given by Sambrook, J. et al., MOLECULAR CLONING, Cold Spring Harbor Laboratory, Chapter 7 (2001)).

The sequence fragment from the start (1 bp) to 413 bp of the MPO1 nucleotide sequence (SEQ ID NO: 1) is used as the probe template. The template is prepared by amplification from the cDNA clone using PCR using the following primers:

```
primer 1:
                                         (SEQ ID NO: 9)
5'-GGGTTCTCATCRCAGCTTTC primer 2:
                                         (SEQ ID NO: 10)
5'-CCATCTCTGACCTCAGGTGTT
```

The probe is labeled with 32P using a Bcabest labeling kit (Takara) according to the manufacturer's instructions. Hybridization are accomplished using ULTRAhyb (Ambion) as the buffer according to the manufacturer's protocol.

Transgenic plants having elevated levels of MPO mRNA compared to the control are selected.

Example 9: Overexpression of MPO and PMT and Suppression of QPT

Description of the Vector

A PMT ORF sequence (NCBI accession number D28506) was inserted between the pTobRD2 promoter and the nos terminator to produce a PMT expression cassette in which PMT is expressed under control of the root cortex specific promoter. (see WO 2007072224).

A QPT suppression cassette is constructed by cloning two copies of a segment of the QPT cDNA in inverted orientation separated by the Pdk intron operably linked to the TobRD2 promoter and the nos terminator such that the cassette expresses an RNA capable of forming a dsRNA region comprising a segment of the QPT sequence. U.S. published patent applications 20060185684.

The PMT expression cassette, the MPO1 overexpression cassette described in Example 8, and the QPT RNAi suppression cassette are cloned within the T-DNA borders of an *Agrobacterium* binary vector plasmid that contains an nptII selectable marker cassette within the T-DNA region to produce the vector having a T-DNA region diagramed in FIG. 6D.

Production of Transgenic Tobacco Plants

The vector is transformed into *Agrobacterium tumefaciens* strain EHA105, which is used to transform leaf segments of tobacco cultivar K326. Transgenic TO shoots are regenerated, and transferred to the rooting medium. Several rooted transgenic plants are transferred to soil.

Analysis of Alkaloid Levels

Alkaloids are extracted from the leaves of the transgenic tobacco plants and analyzed, as described above. The alkaloid profile in leaves of plants sampled 36 days after transfer to soil is analyzed. Transgenic lines that show an increased ratio of nicotine to total alkaloid content are selected.

TABLE 1

| Substrate Specificity of MPO1 and Pig Diamine Oxidase | | | | | | |
|---|---|---|---|---|---|---|
| | Recombinant tobacco MPO1 | | | Pig kidney diamine oxidase | | |
| | Vmax (pkat/mg) | Km (mV) | V/K | Vmax (pkat/mg) | Km (mM) | V/K |
| 1,3-Diaminopropane | 666 ± 86 | 0.158 ± 0.10 | 4200 | | | |
| N-Methy-1,3-diaminopropane | 1270 ± 131 | 0.096 ± 0.02 | 13000 | | | |
| n-Butylamine | 862 ± 138 | 0.249 ± 0.18 | 3500 | | | |
| Putrescine | 902 ± 24 | 0.247 ± 0.04 | 3600 | 79 ± 7.6 | 0.228 ± 0.09 | 350 |
| N-Methylputrescine | 926 ± 160 | 0.036 ± 0.02 | 26000 | 83 ± 13.5 | 0.657 ± 0.24 | 120 |
| Cadavarine | 715 ± 109 | 0.362 ± 0.32 | 2000 | 51 ± 9.2 | 0.915 ± 0.42 | 55 |

What is claimed is:

1. A method for increasing the ratio of nicotine to total alkaloids in a tobacco plant, comprising:

(a) introducing into the plant a nucleic acid construct comprising:

(i) an expression cassette comprising at least one nucleotide sequence selected from the group consisting of a nucleotide sequence set forth in SEQ ID NO: 1, a nucleotide sequence set forth in SEQ ID NO: 5, and a nucleotide sequence that encodes a polypeptide having the amino acid sequence set forth in SEQ ID NO: 2;

(ii) a putrescine N-methyltransferase (PMT) expression cassette; and (iii) a quinolate phosphoribosyl transferase (QPT) suppression cassette; and (b) growing the plant under conditions which allow for overexpression of MPO1, overexpression of PMT, and suppression of QPT, wherein overexpression of MPO1, overexpression of PMT, and suppression of QPT results in the plant having an increased ratio of nicotine to total alkaloids in the plant as compared to a non-transformed control plant.

2. A plant produced by the method of claim 1, wherein the plant comprises the nucleic acid construct.

3. A product with an increased nicotine to total alkaloids ratio produced from the plant of claim 2, wherein the product has an increased nicotine to total alkaloids ratio as compared to a similar product produced from a control plant.

4. The product of claim 3, wherein the product is selected from the group consisting of a cigarette, cigar, pipe tobacco, snus, snuff, and chewing tobacco.

* * * * *

SEQUENCE LISTING

```
Sequence total quantity: 20
SEQ ID NO: 1           moltype = DNA  length = 2465
FEATURE                Location/Qualifiers
source                 1..2465
                       mol_type = other DNA
                       organism = Nicotiana tabacum
SEQUENCE: 1
gggttctcat cgcagctttc ttcctagcta agcagtactc acaatataat ggccactact   60
aaacagaaag tgacggcacc ttctccttct ccttcttctt cgactgcttc ttgctgtcct  120
tccacttcta tcctccgtcg tgaggcaaca gcggccattg cagtcgtggg tgacggcctg  180
cagaattgga ccaacatccc ctccgtcgac gagaagcaga aaaagacggc ctcatcagct  240
ctagcgtcat tgccaaccac tgaacctctt tccaccaata cctctaccaa aggtatccaa  300
atcatgacaa gggctcaaac ctgccatcct ttggaccctt tatctgctgc tgagatctca  360
gtggctgtgg caactgttag agctgccggt gaaacacctg aggtcagaga tgggatgcga  420
tttattgagg tggttctggt agaaccagat aaaagtgtag ttgcattggc agatgcatat  480
ttcttccac cttttcagtc atcattgatg ccgagaacca aaggaggatc tcagattcct  540
actaagcttc ctccaaggag agctaggctt attgtttaca ataagaaaac aaatgagaca  600
```

```
agcatttgga ttgttgagct aaacgaagta catgctgctg ctcgaggtgg acatcacagg    660
ggaaaagtca tcgcatccaa tgttgtccct gatgttcagc cacccataga tgctcaagag    720
tatgctgaat gtgaagctgt ggtgaaaagt tatcctccct ttcgacgcg aatgaggaga     780
agggtattg atgacttgga tcttgtgatg gttgacccct tggtgtgttgg ttatcatagt    840
gaggctgatg ctcctagccg caggctcgcg aaaccacttg tattctgcg acagagagt     900
gactgcccaa tggaaaatgg atatgcaaga ccagttgaag aatatatgt gcttgttgat    960
gtacaaaaca tgaagattat agaatttgaa gaccgaaaac ttgtaccatt acctccagtt   1020
gacccactga ggaactacac tgctggtgag acaagaggag gggttgatcg aagtgatgtg   1080
aaaccctac atattattca gcctgagggt ccaagctttc gtatcagtgg aaactacgta   1140
gagtggcaga gtggaacttt tcggattggt ttcacccta gagagggttt agttatacac    1200
tctgtggcgt atcttgatgg tagcagaggt cgtagaccaa tagcacatag gttgagtttt   1260
gtagagatgt tgtccccta tggagatcca atgatccac attataggaa gaatgcattt     1320
gatgcaggag aagatggcct tggaaagaat gctcattcac tgaagagggg atgtgattgt   1380
ttagggtaca taaagtactt tgatgcccat ttcacaaact ttaccggagt agttgaaacg   1440
actgaaaatt gtgtatgctt gcatgaagaa gatcacggaa tgctttggaa gcatcaagat   1500
tggagaactg gccttgctga agttagacgg tctaggcgac taacagtgtc tttttgtttgt  1560
acagtggcca attatgaata tgcattctac tggcatttct accaggatgg aaaaattgaa   1620
gcggaagtca aactcactgg aattcttagt tggggaacta tgcaacctgg agaatatcgc   1680
aaatatggta ccacaatttt accaggtttt tatgcaccag ttcatcaaca cttcttttgtt  1740
gcacgaatga atatggcagt tgattgtaag ccaggagaag cacacaatca ggttgttgaa   1800
gtaaatgtca aagttgaaga acctggcaag gaaaatgttc ataataatgc attctatgct   1860
gaagaaacat tgcttaggtc tgaattgcaa gcaatgcgtg atgtgattct ctgcttgaa   1920
cgtcattgga ttgttaggaa cacaagaaca gtaaatagaa caggacagct aacagggtac   1980
aagctggtac ctggtccaaa ctgtttgcca ctggctggtc ctgaggcgaa attttttgaga   2040
agagctgcat ttctgaagca caatctatgg gttacaaca atgcacctgg agaagatttt    2100
ccaggaggag agttccctaa tcaaaatccc cgtgttggga aggattagc ttcttgggtc    2160
aagcaagacc ggcctctgga gaaagtgat attgttctct ggtatatttt tggaatcaca    2220
catgttcctc ggttggaaga ctggcctgtt atgccagtag aacacattgg ttttgtgcta   2280
cagccacatg gatactttaa ctgctctccg gctgttgatg tccctccgcc ctttgcatgc   2340
gactcagaaa gcagagacag tgatgttact gaaactagtg tagcaaagtc cactgccact   2400
agcttgctgg ccaagctttg aatgtttcgt ttatcctaac atgagtcctc ctcgcctatt   2460
taatc                                                              2465

SEQ ID NO: 2           moltype = AA   length = 790
FEATURE                Location/Qualifiers
source                 1..790
                       mol_type = protein
                       organism = Nicotiana tabacum
SEQUENCE: 2
MATTKQKVTA PSPSPSSSTA SCCPSTSILR REATAAIAVV GDGLQNWTNI PSVDEKQKKT     60
ASSALASLPT TEPLSTNTST KGIQIMTRAQ TCHPLDPLSA AEISVAVATV RAAGETPEVR    120
DGMRFIEVVL VEPDKSVVAL ADAYFFPPFQ SSLMPRTKGG SQIPTKLPPR RARLIVYNKK    180
TNETSIWIVE LNEVHAAARG GHHRGKVIAS NVVPDVQPPI DAQEYAECEA VVKSYPPFRD    240
AMRRRGIDDL DLVMVDPWCV GYHSEADAPS RRLAKPLVFC RTESDCPMEN GYARPVEGIY    300
VLVDVQNMKI IEFEDRKLVP LPPVDPLRNY TAGETRGGVD RSDVKPLHII QPEGPSFRIS    360
GNYVEWQKWN FRIGFTPREG LVIHSVAYLD GSRGRRPIAH RLSFVEMVVP YGDPNDPHYR    420
KNAFDAGEDG LGKNAHSLKR GCDCLGYIKY FDAHFTNFTG GVETTENCVC LHEEDHGMLW    480
KHQDWRTGLA EVRRSRRLTV SFVCTVANYE YAFYWHFYQD GKIEAEVKLT GILSLGALQP    540
GEYRKYGTTI LPGLYAPVHQ HFFVARMNMA VDCKPGEAHN QVVEVNVKVE EPGKENVHNN    600
AFYAEETLLR SELQAMRDCD PFSARHWIVR NTRTVNRTGQ LTGYKLVPGP NCLPLAGPEA    660
KPLRRAAFLK HNLWVTQYAP GEDFPGGEFP NQNPRVGEGL ASWVKQDRPL EESDIVLWYI    720
FGITHVPRLE DWPVMPVEHI GFVLQPHGYF NCSPAVDVPP PFACDSESRD SDVTETSVAK    780
STATSLLAKL                                                          790

SEQ ID NO: 3           moltype = DNA   length = 2405
FEATURE                Location/Qualifiers
source                 1..2405
                       mol_type = other DNA
                       organism = Nicotiana tabacum
SEQUENCE: 3
gattacactt ggcattttca ttccattcgc aatggccgca actttgcaca aggtgactcc     60
gactactgct tcggcctccg cttctatcgc ccgtcgtgag tccgccgcag cctccgtcct    120
ggtggacgat cagcagaaac aaacgccggc tctgacgtca ttgcttaact ctcaacctcc    180
ttcctccaat ccctctagca aagggaaaca aatcatccca agagctcata catgccatcc    240
tttggaccct ttatctgctg ctgaaatctc tgtggctgtg gcgaccgtca gagctgccgg    300
tgaaacaccc gaggtcagag atggcatgcg ctttattgag gtggttcttc tggaacctga    360
taaaagtgtc gttgcactgg ctgatgccta tttcttccca ccttttccaat cttcattgat   420
gtccagaagg aaaggagggc ttcccattcc tactaagctt cctccaaggc gagctagact    480
tattgcatat aataagaaaa caaatgagac aagcatatgg attgttgagc tagctgaagt    540
acatgctgct gctcgaggtg gacatcacaa gggaaaagtg atttcatcca atgttgttcc    600
agatgttcag ccacctatag atgcacaaga gtatgctgac tgtgaagctg tagttaaaaa    660
ttatcctcct tttaggaag caatgaagag aagggggatt gatgacatgg atgttgtgat    720
ggtggacccc tggtgcgttg gttatcacag tgaggctgat gctcctagcc gcaggcttgc    780
caaaccgcta gtattctgca gaacagagag tgactgccca atggaaaatg gatatgcaag    840
accggttgaa ggaatatatg cccttgttga tgtgcaaaac atgcaggtga tagagtttga   900
agaccgcaaa cttgtacctt tacctccagc tgatccactg ggaattaca ctgctggtga     960
gacaagagga gggtcgatc gaagtgatgt aaaacccctc cagattattc agccagaggg   1020
tccaagcttt cgagtcaatg gaactatgt ggaatggcaa agtgaaact tccgagtagg     1080
tttcacccct agggagggtt tggttataca ctctgtggca tatcttgacg gtagcagggg   1140
```

-continued

```
tcggagaccc atagcccata ggttgagttt tgtggagatg gttgtcccct atggggatcc    1200
aaatgaccca cattacagaa agaacgcttg tgatgcagga gaagatgggc tcggaaagaa    1260
tgctcattca cttaagaggg gatgcgattg tttaggatac ataaagtact ttgatgccaa    1320
ttttgcaaat tttactggag gagtagaaac cactgaaaat tgtgtatgtt tgcatgaaga    1380
agatcacggg atgctctgga agcatcaaga ttggagaact ggccttgcag aagttagacg    1440
gtctagacga cttacagttt cttttatttg cactgtggcc aattatgaat atggattcta    1500
ctggcactta taccaggatg ggaaaattga agcagaagtc aaactcacag gaattctcag    1560
tttgggagca ttgcccccg gagagtctcg taaatatggc accacaatag caccaggatt    1620
gtatgcacct gttcatcaac acttctttgt tgctcgtatg aatatggcag ttgattgtaa    1680
accaggagaa gcacacaatc aggttgttga agttaatgta agagttgaag aacctgggaa    1740
agaaaatgtt cacaacaatg cgttctatgc taaggaaaca gtgcttacgt ctgaattgca    1800
agcaatgcgg gactgtgata ctttatctgc tcgtcattgg attgttagga acacaagaac    1860
atccaataga acaggacagc taacagggta caagctggta cctggcccta gctgtttgcc    1920
attagctggt cctgaggcta agtttttgag aagagctgta tttttgaagc acaatctatg    1980
ggttacacaa tatgcacccg agaagatttt tccagggggga gagttcccta atcaaaatcc    2040
acgtgttggt gagggattag cttcttgggt taagcaagat cgttctctgg aagaaagtga    2100
tgttgttctc tggtatgttt ttggaatcac acatgttcct cggttggagg actggcctgt    2160
tatgccagtt gaacatatcg gttttatgct tcagccgcat ggattcttta actgctctcc    2220
tgctgtagat gtacctcctc tcggggatg tgacttggaa atcaaagaca gtgatggttc    2280
agaaaatggt gtagcaaagc ccactcccag tagtttgatg gccaagcttt gaaaggtttg    2340
tgattcagaa aatagtcctc tcgtattatc tgcacagaca cacaacaggc aaacttccat    2400
ctttc                                                                2405

SEQ ID NO: 4           moltype = AA  length = 766
FEATURE                Location/Qualifiers
source                 1..766
                       mol_type = protein
                       organism = Nicotiana tabacum
SEQUENCE: 4
MAATLHKVTP TTASASASIA RRESAAASVL VDDQQKQTPA LTSLLNSQPP SSNPSSKGKQ     60
IMPRAHTCHP LDPLSAAEIS VAVATVRAAG ETPEVRDGMR FIEVVLLEPD KSVVALADAY    120
FFPPPFQSSLM SRRKGGLPIP TKLPPRRARL IAYNKKTNET SIWIVELAEV HAAARGGHHK   180
GKVISSNVVP DVQPPIDAQE YADCEAVVKN YPPFREAMKR RGIDDMDVVM VDPWCVGYHS    240
EADAPSRRLA KPLVFCRTES DCPMENGYAR PVEGIYALVD VQNMQVIEFE DRKLVPLPPA    300
DPLRNYTAGE TRGGVDRSDV KPLQIIQPEG PSFRVNGNYV EWQKWNFRVG FTPREGLVIH    360
SVAYLDGSRG RRPIAHRLSF VEMVVPYGDP NDPHYRKNAF DAGEDGLGKN AHSLKRGCDC    420
LGYIKYFDAN FANFTGGVET TENCVCLHEE DHGMLWKHQD WRTGLAEVRR SRRLTVSFIC    480
TVANYEYGFY WHLYQDGKIE AEVKLTGILS LGALPPGESR KYGTTIAPGL YAPVHQHFFV    540
ARMNMAVDCK PGEAHNQVVE VNVRVEEPGK ENVHNNAFYA KETVLTSELQ AMRDCDTLSA    600
RHWIVRNTRT SNRTGQLTGY KLVPGPSCLP LAGPEAKFLR RAAFLKHNLW VTQYAPGEDF    660
PGGEFPNQNP RVGEGLASWV KQDRSLEESD VVLWYVFGIT HVPRLEDWPV MPVEHIGFML    720
QPHGFFNCSP AVDVPPPRGC DLEIKDSDGS ENGVAKPTPS SLMAKL                   766

SEQ ID NO: 5           moltype = DNA  length = 2373
FEATURE                Location/Qualifiers
source                 1..2373
                       mol_type = other DNA
                       organism = Nicotiana tabacum
SEQUENCE: 5
atggccacta ctaaacagaa agtgacggca ccttctcctt ctccttcttc ttcgactgct     60
tcttgcgtc cttccacttc tatcctccgt cgtgaggcaa cagcggccat tgcagtcgtg    120
ggtgacggcc tgcagaattg gaccaacatc ccctccgtcg acgagaagca gaaaaagacg    180
gcctcatcag ctctagcgtc attgccaacc actgaacctc tttccaccaa tacctctacc    240
aaaggtatcc aaatcatgac aaagggctca acctgccatc ctttggaccc tttatctgct    300
gctgagatct cagtggctgt ggcaactgtt agagctgccg gtgaaacacc tgaggtcaga    360
gatgggatgc gatttattga ggtggttctg gtagaaccag ataaaagtgt agttgcattg    420
gcagatgcat atttcttccc acctttcag tcatcattga tgccgagaac caaggaggaa    480
tctcagattc ctactaagct tcctccaagg agagctaggc ttattgttta caataagaaa    540
acaaatgaga caagcatttg gattgttgag ctaaacgaag tacatgctgc tgctcgaggt    600
ggacatcaca ggggaaaagt catcgcatcc aatgttgtcc ctgatgttca gccacccata    660
gatgctcaag agtatgctga atgtgaagct gtggtgaaaa gttatcctcc ctttcgagac    720
gcaatgagga agggggtat tgatgacttg gatcttgtga tggttgaccc ttggtgtgtt    780
ggttatcata gtgaggctga tgctcctagc cgcaggctcg cgaaaccact tgtattctgc    840
aggacagaga gtgactgccc aatggaaaat ggatatgcaa gaccagttga aggaatatat    900
gtgcttgttg atgtacaaaa catgaagatt ataagaattg aagaccgaaa acttgtacca    960
ttacctccag ttgacccact gaggaactac actgctggtg agacaagagg aggggttgat   1020
cgaagtgatg tgaaacccct acatattatt cagcctgagg gtccaagctt tcgtatcagt   1080
ggaaactacg tagagtggca gaagtggaac tttcggattg gtttcacccc tagagaggt    1140
ttagttatac actctgtggc gtatcttgat ggtgacggag tcgtagacca aatagcacat   1200
aggttgagtt ttgtagagat ggttgtcccc tatggagatc caaatgatcc acattatagg   1260
aagaatgcat ttgatgcagg agaagatggc cttggaaaga atgctcattc actgaagagg   1320
ggatgtgatt gtttagggta cataaagtac tttgatgccc atttcacaaa ctttaccgga   1380
ggagttgaaa cgactgaaaa ttgtgtatgc tgcatgaaga agatcacgg aatgctttgg   1440
aagcatcaag attggagaac tggccttgct gaagttagag gctaggcg actaacagtg    1500
tcttttgttt gtacagtggc caattatgaa tatgcattct actggcattt ctaccaggat   1560
ggaaaattg aagcggaagt caaactcact ggaattctta gtttgggagc attgcaacct   1620
ggagaatatc gcaaatatgg taccacaatt ttaccaggtt tgtatgcacc agttcatcaa   1680
cacttctttg ttgcacgaat gaatatggca gttgattgta agccaggaga agcacacaat   1740
caggttgttg aagtaaatgt caaagttgaa gaacctggca ggaaaatgt tcataataat   1800
```

-continued

```
gcattctatg ctgaagaaac attgcttagg tctgaattgc aagcaatgcg tgattgtgat   1860
ccattctctg ctcgtcattg gattgttagg aacacaagaa cagtaaatag aacaggacag   1920
ctaacagggt acaagctggt acctggtcca aactgtttgc cactggctgg tcctgaggcg   1980
aaatttttga gaagagctgc atttctgaag cacaatctat gggttacaca atatgcacct   2040
ggagaagatt ttccaggagg agagttccct aatcaaaatc cccgtgttgc cgagggatta   2100
gcttcttggg tcaagcaaga ccggcctctg gaagaaagtg atattgttct ctggtatatt   2160
tttggaatca cacatgttcc tcggttggaa gactggcctg ttatgccagt agaacacatt   2220
ggttttgtgc tacagccaca tggatacttt aactgctctc cggctgttga tgtccctccg   2280
ccctttgcat gcgactcaga aagcagagac agtgatgtta ctgaaactag tgtagcaaag   2340
tccactgcca ctagcttgct ggccaagctt tga                                2373

SEQ ID NO: 6            moltype = DNA   length = 2301
FEATURE                 Location/Qualifiers
source                  1..2301
                        mol_type = other DNA
                        organism = Nicotiana tabacum
SEQUENCE: 6
atggccgcaa ctttgcacaa ggtgactccg actactgctt cggcctccgc ttctatcgcc   60
cgtcgtgagt ccgccgcagc ctccgtcctg gtggacgatc agcagaaaca aacgccggct   120
ctgacgtcat tgcttaactc tcaacctcct cctccaatc cctctagcaa agggaaacaa    180
atcatgccaa gagctcatac atgccatcct ttggacccct tatctgctgc tgaaatctct   240
gtggctgtgg cgaccgtcag agctgccggt gaaacaccgg aggtcagaga tggcatgcgc   300
tttattgagg tggttcttct ggaacctgat aaaagtgtcg ttgcactggc tgatgcctat   360
ttcttcccac ctttccaatc ttcattgatg tccagaagga aaggagggct tcccattcct   420
actaagcttc ctcaaggcg agctagactt attgcatata ataagaaaac aaatgagaca    480
agcatatgga ttgttgagct agctgaagta catgctgctg ctcgaggtgg acatcacaag   540
ggaaaagtga tttcatccaa tgttgttcca gatgttcagc cacctataga tgcacaagag   600
tatgctgact gtgaagctgt agttaaaaat tatcctcctt ttagggaagc aatgaagaga   660
aggggtattg atgacatgga tgttgtgatg gtggacccct ggtgcgttgg ttatcacagt   720
gaggctgatg ctcctagccg caggcttgcc aaaccgctag tattctgcag aacagagatt   780
gactgcccaa tggaaaatgg atatgcaaga ccggttgaag gaatatatgc ccttgttgat   840
gtgcaaaaca tgcaggtgat agagtttgaa gaccgcaaac ttgtaccctt tacctccagct  900
gatccactga ggaattacac tgctggtgag acaagaggag gggtcgatcg aagtgatgta   960
aaaccctcc agattattca gccagagggt ccaagcttgg gagtcaatgg gaactatgtg   1020
gaatggcaaa agtggaactt ccgagtaggt ttcacccta gggagggttt ggttatacac    1080
tctgtggcat atcttgacgg tagcaggggt cggagcccca tagcccatag gttgagtttt   1140
gtggagatgg ttgtccccta tggggatcca aatgacccac attacagaaa gaacgctttc   1200
gatgcaggag aagatgggct cggaaagaat gctcattcac ttaagagggg atgcgattgt   1260
ttaggataca taagtactt tgatgccaat tttgcaaatt tactggagg agtagaaacc    1320
actgaaaatt gtgtatgttt gcatgaagaa gatcacggga tgctctggaa gcatcaagat   1380
tggagaactg gccttgcaga agttagacgg tctagacgac ttacagtttc ttttatttgc   1440
actgtggcca attatgaata tggattctac tggcacttat accaggatgg gaaaattgaa   1500
gcagaagtca aactcacagg aattctcagt ttgggagcat tgcccccggg agagtctcgt   1560
aaatatggca ccacaatagc accaggattg tatgcacctg ttcatcaaca cttctttgtt   1620
gctcgtatga atatgcagt tgattgtaaa ccaggagaag cacacaatca ggttgttgaa    1680
gttaatgtaa gagttgaaga acctgggaaa gaaaatgttc acaacaatgc gttctatgct   1740
aaggaaacag tgcttacgtc tgaattgcaa gcaatgcggg actgtgatac tttatctgct   1800
cgtcattgga ttgttaggaa cacaagaaca tccaatagaa caggacagct aacagggtac   1860
aagctggtac ctgccctag ctgtttgcca ttagctggtc ctgaggctaa gtttttgaga    1920
agagctgcat ttttgaagca caatctatgg gttacacaat atgcacccgg agaagatttt   1980
ccagggggag agttccctaa tcaaaatcca cgtgttgctg agggattagc ttcttgggtt   2040
aagcaagatc gttctctgga agaaagtgat gttgttctct ggtatgtttt tggaatcaca   2100
catgttcctc ggttggagga ctggcctgtt atgccagttg aacatatcgg ttttatgctt   2160
cagccgcatg gattctttaa ctgctctcct gctgtagatg tacctcctcc tcggggatgt   2220
gacttggaaa tcaaagacag tgatggttca gaaaatggtg tagcaaagcc cactcccagt   2280
agtttgatgg ccaagctttg a                                             2301

SEQ ID NO: 7            moltype = DNA   length = 40
FEATURE                 Location/Qualifiers
misc_feature            1..40
                        note = Description of Artificial Sequence: Synthetic primer
source                  1..40
                        mol_type = other DNA
                        organism = synthetic construct
SEQUENCE: 7
cgatatcaat ggccactact aaacagaaag tgacggcacc                          40

SEQ ID NO: 8            moltype = DNA   length = 27
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 8
tcgccggcgt caaagcttgg ccagcaa                                        27

SEQ ID NO: 9            moltype = DNA   length = 20
FEATURE                 Location/Qualifiers
```

| | |
|---|---|
| misc_feature | 1..20 |
| | note = Description of Artificial Sequence: Synthetic primer |
| source | 1..20 |
| | mol_type = other DNA |
| | organism = synthetic construct |

SEQUENCE: 9
gggttctcat crcagctttc                                                    20

| | |
|---|---|
| SEQ ID NO: 10 | moltype = DNA  length = 21 |
| FEATURE | Location/Qualifiers |
| misc_feature | 1..21 |
| | note = Description of Artificial Sequence: Synthetic primer |
| source | 1..21 |
| | mol_type = other DNA |
| | organism = synthetic construct |

SEQUENCE: 10
ccatctctga cctcaggtgt t                                                  21

| | |
|---|---|
| SEQ ID NO: 11 | moltype = DNA  length = 27 |
| FEATURE | Location/Qualifiers |
| misc_feature | 1..27 |
| | note = Description of Artificial Sequence: Synthetic primer |
| source | 1..27 |
| | mol_type = other DNA |
| | organism = synthetic construct |

SEQUENCE: 11
gttagacgct cgaggcgact aacagtg                                            27

| | |
|---|---|
| SEQ ID NO: 12 | moltype = DNA  length = 27 |
| FEATURE | Location/Qualifiers |
| misc_feature | 1..27 |
| | note = Description of Artificial Sequence: Synthetic primer |
| source | 1..27 |
| | mol_type = other DNA |
| | organism = synthetic construct |

SEQUENCE: 12
gcatattgtg aattccatag attgtgc                                            27

| | |
|---|---|
| SEQ ID NO: 13 | moltype = DNA  length = 27 |
| FEATURE | Location/Qualifiers |
| misc_feature | 1..27 |
| | note = Description of Artificial Sequence: Synthetic primer |
| source | 1..27 |
| | mol_type = other DNA |
| | organism = synthetic construct |

SEQUENCE: 13
gttagacggt ctagacgact aacagtg                                            27

| | |
|---|---|
| SEQ ID NO: 14 | moltype = DNA  length = 27 |
| FEATURE | Location/Qualifiers |
| misc_feature | 1..27 |
| | note = Description of Artificial Sequence: Synthetic primer |
| source | 1..27 |
| | mol_type = other DNA |
| | organism = synthetic construct |

SEQUENCE: 14
gcatattgtg taagctttag attgtgc                                            27

| | |
|---|---|
| SEQ ID NO: 15 | moltype = DNA  length = 23 |
| FEATURE | Location/Qualifiers |
| misc_feature | 1..23 |
| | note = Description of Artificial Sequence: Synthetic primer |
| source | 1..23 |
| | mol_type = other DNA |
| | organism = synthetic construct |

SEQUENCE: 15
cctttggacc ctttatctgc tgc                                                23

| | |
|---|---|
| SEQ ID NO: 16 | moltype = DNA  length = 26 |
| FEATURE | Location/Qualifiers |
| misc_feature | 1..26 |
| | note = Description of Artificial Sequence: Synthetic primer |
| source | 1..26 |
| | mol_type = other DNA |
| | organism = synthetic construct |

SEQUENCE: 16
ggtcttgcat atccattttc cattgg                                             26

| | |
|---|---|
| SEQ ID NO: 17 | moltype = DNA  length = 21 |

```
FEATURE              Location/Qualifiers
misc_feature         1..21
                     note = Description of Artificial Sequence: Synthetic primer
source               1..21
                     mol_type = other DNA
                     organism = synthetic construct
SEQUENCE: 17
cagctttctt cctagctaag c                                                21

SEQ ID NO: 18        moltype = DNA  length = 23
FEATURE              Location/Qualifiers
misc_feature         1..23
                     note = Description of Artificial Sequence: Synthetic primer
source               1..23
                     mol_type = other DNA
                     organism = synthetic construct
SEQUENCE: 18
ctctctgtcc tgaatacaag tgg                                              23

SEQ ID NO: 19        moltype = DNA  length = 23
FEATURE              Location/Qualifiers
misc_feature         1..23
                     note = Description of Artificial Sequence: Synthetic primer
source               1..23
                     mol_type = other DNA
                     organism = synthetic construct
SEQUENCE: 19
tggaagtttg cctgttgtgt gtc                                              23

SEQ ID NO: 20        moltype = DNA  length = 23
FEATURE              Location/Qualifiers
misc_feature         1..23
                     note = Description of Artificial Sequence: Synthetic primer
source               1..23
                     mol_type = other DNA
                     organism = synthetic construct
SEQUENCE: 20
aagctggtac ctggtccaaa ctg                                              23
```